(12) United States Patent
Halley et al.

(10) Patent No.: US 7,935,819 B2
(45) Date of Patent: May 3, 2011

(54) CYCLIC UREA DERIVATIVES, PREPARATION THEREOF AND PHARMACEUTICAL USE THEREOF AS KINASE INHIBITORS

(75) Inventors: Frank Halley, Chaville (FR); Youssef El-Ahmad, Creteil (FR); Victor Certal, Draveil (FR); Corinne Venot, Paris (FR); Anne Dagallier, Paris (FR); Hartmut Strobel, Liederbach (DE); Kurt Ritter, Frankfurt (DE); Sven Ruf, Mainz (DE)

(73) Assignee: Aventis Pharma S.A., Antony (FR)

( * ) Notice: Subject to any disclaimer, the term of this patent is extended or adjusted under 35 U.S.C. 154(b) by 38 days.

(21) Appl. No.: 12/173,380

(22) Filed: Jul. 15, 2008

(65) Prior Publication Data

US 2009/0082379 A1    Mar. 26, 2009

Related U.S. Application Data

(63) Continuation of application No. PCT/FR2007/000079, filed on Jan. 17, 2007.

(30) Foreign Application Priority Data

Jan. 23, 2006 (FR) ...................................... 06 00567

(51) Int. Cl.
C07D 239/02 (2006.01)
(52) U.S. Cl. ...................................................... 544/316
(58) Field of Classification Search .................. 544/316
See application file for complete search history.

(56) References Cited

U.S. PATENT DOCUMENTS

| | | | |
|---|---|---|---|
| 5,411,981 A | 5/1995 | Gaillard-Kelly et al. | |
| 6,004,963 A | 12/1999 | Zimmer et al. | |
| 6,022,875 A | 2/2000 | Zimmer et al. | |
| 6,759,415 B1 | 7/2004 | Poitout et al. | |
| 7,354,933 B2 | 4/2008 | Patek et al. | |
| 2004/0248884 A1* | 12/2004 | Patek et al. | 514/218 |
| 2007/0259891 A1 | 11/2007 | Strobel et al. | |
| 2008/0004300 A1 | 1/2008 | Strobel et al. | |
| 2008/0021029 A1 | 1/2008 | Strobel et al. | |
| 2008/0108654 A1 | 5/2008 | Patek et al. | |

FOREIGN PATENT DOCUMENTS

| | | |
|---|---|---|
| EP | 0 034 536 | 8/1981 |
| EP | 0 494 819 A1 | 7/1992 |
| FR | 2 499 995 | 8/1982 |
| WO | WO 2004/022572 | 3/2004 |
| WO | WO 2004/070050 A2 | 8/2004 |
| WO | WO 2005/049580 A1 | 6/2005 |
| WO | WO 2006/010641 A2 | 2/2006 |
| WO | WO 2006/010642 | 2/2006 |
| WO | WO 2006/010643 | 2/2006 |

OTHER PUBLICATIONS

Hcaplus 1999:132856, "The insulin-like growth factor network and breast cancer", Ellis, Mathew, 1999.*

Hcaplus 1997:404533, "The Growth factors mediate flucocorticoid receptor function and dexamethasone-induced reression of osteoblastic lesions in hormone refractory prostate cancer", 1997, Koutsilieris et. al.*

Patani et. al., "Bioisosterism: A Rational Approach in Drug Design", Chem. Rev. 1996, pp. 3147-3176.*

Ali et al, An Improved Method for the Palladium-Catalyzed Amination of Aryl Iodides, J. Org. Chem., 2001 (66) pp. 2560-2565.

Baserga, The IGF-I Receptor in Cancer Research, Exp. Cell. Res., 1999 (253) pp. 1-6.

Brana et al, Synthesis of 4,7,8a,9-Tetrahydro-3H-diimidazo-[1,5-alpha:4',5'-d]pyridine Derivatives, J. Heterocyclic Chem, 2002 (39) pp. 417-420.

Bryce et al, A Highly Stereoselective Synthesis of an Azaspirolactam Related to Cephalotaxus Alkaloids, Tetrahedron Letters, 1987 (28) 5 pp. 577-580.

Bundgaard et al, A Novel Solution-Stable, Water-Soluble Prodrug Type for Drugs Containing a Hydroxyl or an NH-Acidic Group, J. Med. Chem., 1989 (32) 12, pp. 2503-2507.

Campos et al, Asymmetric Synthesis of a Prostaglandin D2 Receptor Antagonist, J. Org. Chem., 2005 (70) pp. 268-274.

Cardone et al, Regulation of Cell Death Protease Caspase-9 by Phosphorylation, Science, 1998 (282) pp. 1318-1321.

Cary et al, Stimulation of cell migration by overexpression of focal adhesion kinase and its association with Src and Fyn, Journal of Cell Science, 1996 (109), pp. 1787-1794.

Chan et. al, The Role of Protein Tyrosine Kinases and Protein Tyrosine Phosphatases in T Cell Antigen Receptor Signal Transduction, Annu. Rev. Immunol., 1994 (12) pp. 555-592.

Chen et al, Association of focal adhesion kinase with its potential substrate phosphatidylinositol 3-kinase, Proc. Natl. Acad. Sci. USA, 1994 (91), pp. 10148-10152.

(Continued)

Primary Examiner — Janet L Andres
Assistant Examiner — Heidi Reese
(74) Attorney, Agent, or Firm — Scully, Scott, Murphy & Presser, P.C.

(57) ABSTRACT

Compounds of formula (I):

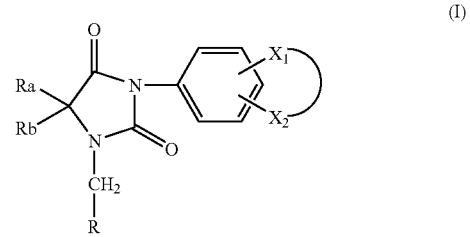

(I)

wherein Ra, Rb, R, $X_1$ and $X_2$ are as defined in the disclosure, pharmaceutical compositions comprising said compounds, processes for making and methods of using the same are provided.

12 Claims, No Drawings

OTHER PUBLICATIONS

Font et al, Development of an Efficient and Straightforward Methodology Toward the Synthesis of Molecularly Diverse 2,6-Disubstituted 3,4-Dihydropyrimidin-4(3H)-ones, Synthesis, 2002 (13) pp. 1833-1842.

Francis et al, Synthesis and Benzodiazepine Binding Activity of a Series of Novel [1,2,4]Triazolo[1,5-c] quinazolin-5(6H)-ones, J. Med. Chem., 1991 (34) 281-290.

Fukase et al, 4-Pivaloylaminobenzyl Ether, a New Temporary Protection for Hydroxyl Functions, Tetrahedron Letters, 1991 (32) 32 pp. 4019-4022.

Hanks et al, The Eukaryotic Protein Kinase Superfamily: Kinase (Catalytic) Domain Structure and Classification, FASEB, 1995 (9) pp. 576-596.

Iwashita et al, Signal Transduction System for Growth Factor Receptors Associated with Tyrosine Kinase Activity: Epidermal Growth Factor Receptor Signalling and its Regulation, Cellular Signalling, 1992 (4) 2 pp. 123-132.

Jeong et al, Stereospecific Synthesis of Novel (Z)-beta-Fluoro-beta-trifluoromethyl-alpha-phenylvinylstannane and its Cross-Coupling Reactions with Aryl Iodides, Bull. Korean Chem. Soc., 2002 (23) 12 pp. 1823-1826.

Johnson et al, Asymmetric Carbon-Carbon Bond Formations in Conjugate Additions of Lithiated N-Boc Allylic and Benzylic Amines to Nitroalkenes: Enantioselective Synthesis of Substituted Piperidines, Pyrrolidines, and Pyrimidinones, J. Am. Chem. Soc., 2002 (124) pp. 11689-11698.

Khwaja, Akt is more than just a Bad kinase, Nature, 1999 (401), pp. 33-34.

Kitada et al, Expression and Locaton of Pro-Apoptotic Bcl-2 Family Protein BAD in Normal Human Tissues and Tumor Cell Lines, American Journal of Pathology, 1998 (152) 1 pp. 51-61.

Kornberg et al, Cell Adhesion or Integrin Clustering Increases Phosphorylation of a Focal Adhesion-associated Tyrosine Kinase, J. Biol. Chem., 1992 (267) 33, pp. 23439-23442.

Kozima et al, Formation of Organotin-Nitrogen Bonds III*. N-Trialkyltin-5-Subsituted Tetrazoles, J. Organometallic Chemistry, vol. 33, 1971, pp. 337-346.

Ling et al, Malignant Astrocytoma Cell Attachment and Migration to Various Matrix Proteins Is Differentially Sensitive to Phosphoinositide 3-OH Kinase Inhibitors, J. Cell. Biochemistry, 1999 (73), pp. 533-544.

Maung et al, Requirement for focal adhesion kinase in tumor cell adhesion, Oncogene,1999 (18), pp. 6824-6828.

Mazure et al, Induction of Vascular Endothelial Growth Factor by Hypoxia Is Modulated by a Phosphatidylinositol 3-Kinase/Akt Signaling Pathway in Ha-ras-Transformed Cells Through a Hypoxia Inducible Factor-1 Transcriptional Element, Blood, 1997 (90) 9, pp. 3322-3331.

Nefzi et al, Solid-Phase Synthesis of Linear Ureas Tethered to Hydantoins and Thiohydantoins, J. Comb. Chem., 2002 (4) pp. 175-178.

Newton et.al, Protein Kinase C: Structure, Function, and Regulation, J. Biol. Chem., 1995 (270) 48 pp. 28495-28498.

Ohsawa et al, Thermal Decomposition of 2H-[1,2,4]Oxadiazolo[2,3-a]pyridine-2-thione and 2H-[1,2,4] Oxadiazolo[2,3-b]pyridazine-2-thiones: Generation of Aza-hetero-aromatic alpha-fsocyanates and Their Utilization for the Synthesis of Unsymmetrical Disubstituted Ureas, Chem. Pharm. Bull., 1980 (28) 12 pp. 3570-3575.

Oktay et al, Integrin-mediated Activation of Focal Adhesion Kinase Is Required for Signaling to Jun NH2-terminal Kinase and Progression through the G1 Phase of the Cell Cycle, J. Cell. Biol., 1999 (145) 7 pp. 1461-1469.

Owens et al, Overexpression of the Focal Adhesion Kinase (p125 FAK) in Invasive Human Tumors 1, Cancer Research, 1995 (55), pp. 2752-2755.

Pines, Cyclins and cyclin-dependent kinases: take your partners, Trends in Biochemical Sciences, 1993 (18) pp. 195-197.

Ramsay et al, A Novel, Efficient Synthesis of 3,3-Dimethylindoline, Synthetic Comm., 1995 (25) 24 pp. 4029-4033.

Richardson et al, A mechanism for regulation of the adhesion-associated protein tyrosine kinase pp125 FAK, Nature, 1996 (380), pp. 538-540.

Rousseau et al, The reaction of 2-aminopyridine 1-oxides with thiophosgene. 2H-[1,2,4]Oxadiazolo[2,3-a] pyridin-2-thiones, Can. J. Chem., 1977 (55) pp. 3736-3739.

Schaller et al, Autophosphorylation of the Focal Adhesion Kinase, pp125 FAK, Directs SH2-Dependent Binding of pp60src, Mol. Cell. Biol., 1994 (14), pp. 1680-1688.

Schlaepfer et al, Focal Adhesion Kinase Overexpression Enhances Ras-dependent Integrin Signaling to ERK2/Mitogen-activated Protein Kinase through Interactions with and Activation of c-Src, J. Biol. Chem., 1997 (272) 20, pp. 13189-13195.

Schlaepfer et al, Integrin-mediated signal transduction linked to Ras pathway by GRB2 binding to focal adhesion kinase, Nature, 1994 (372) 22, pp. 786-791.

Schlaepfer et al, Signaling through focal adhesion kinase, Prog. Biophy. Mol. Biol., 1999 (71), pp. 435-478.

Sener et al, Studies on the Reactions of Cyclic Oxalyl Compounds With Hydrazines or Hydrazones: Synthesis and Reactions of 4-Benzoyl-1-(3-Nitrophenyl)-5-Phenyl-1H-Pyrazole-3-Carboxylic Acid , J. Heterocyclic Chem., 2002 (39) pp. 869-875.

Sieg et al, Required role of focal adhesion kinase (FAK) for integrin-stimulated cell migration, J. Cell Science, 1999 (112), pp. 2677-2691.

Sollogoub et al, First synthesis of 1-deazacytidine, the C-nucleoside analogue of cytidine, Tetrahedron Letters, 2002 (43) pp. 3121-3123.

Stafford et al, Identification and Structure—Activity Studies of Novel Ultrashort-Acting Benzodiazepine Receptor Agonists, Bioorg. Med. Chem. Letters, 2002 (12) pp. 3215-3218.

Vuori et al, Induction of p130cas Signaling Complex Formation upon Integrin-Mediated Cell Adhesion: a Role for Src Family Kinases, Mol. Cell. Biol., 1996 (16) 6, pp. 2606-2613.

Wang et al, p125 focal adhesion kinase promotes malignant astrocytoma cell proliferation in vivo, J. Cell Sci., 2000 (113), pp. 4221-4230.

Weiner et al, Expression of focal adhesion kinase gene and Invasive cancer, Lancet., 1993 (342), pp. 1024-1025.

Xing et al, Direct Interaction of v-Src with the Focal Adhesion Kinase Mediated by the Src SH2 Domain, Mol. Biol. of the Cell, 1994 (5), pp. 413-421.

Xu et al, Attenuation of the Expression of the Focal Adhesion Kinase Induces Apoptosis in Tumor Cells, Cell Growth Diff., 1996 (7), pp. 413-418.

Yin et al, Pd-Catalyzed Intermolecular Amidation of Aryl Halides: The Discovery that Xantphos Can Be Trans-Chelating in a Palladium Complex, JACS, 2002 (124) pp. 6043-6048.

Zanka et al, Highly Efficient Conversion of Benzoates to Alcohols with Sodium Borohydride in DME-MeOH, Synnlett, 1999 (10) pp. 1636-1638.

Zhao et al, Indoline and Piperazine Containing Derivatives as a Novel Class of Mixed D2/D4 Receptor Antagonists. Part 2: Asymmetric Synthesis and Biological Evaluation, Bioorg. Med. Chem. Letters, 2002 (12) pp. 3111-3115.

Zhao et al, Regulation of the Cell Cycle by Focal Adhesion Kinase, J. Cell. Biol., 1998 (143) 7, pp. 1997-2008.

Zhong et al, Modulation of Hypoxia-inducible Factor 1 alpha Expression by the Epidermal Growth Factor/Phosphatidylinositol 3-Kinase/PTEN/AKT/FRAP Pathway in Human Prostate Cancer Cells: Implications for Tumor Angiogenesis and Therapeutics, Cancer Research, 2000 (60), pp. 1541-1545.

U.S. Appl. No. 12/173,191, filed Jul. 15, 2008, Halley et al.

Dyer et al, Preparation of Poly(hydrouracils) and Poly(iminoimidazolidinones), Journal of Polymer Science, Polymer Chemistry Edition, 1969, 7(3), pp. 833-849.

* cited by examiner

CYCLIC UREA DERIVATIVES, PREPARATION THEREOF AND PHARMACEUTICAL USE THEREOF AS KINASE INHIBITORS

The present invention relates to novel cyclic urea derivatives, to a process for preparing them, to their use as medicaments, to pharmaceutical compositions containing them and to the pharmaceutical use of such derivatives for preventing and treating complaints that may be modulated by inhibiting the activity of protein kinases.

The present invention relates to novel cyclic urea derivatives that have inhibitory effects on protein kinases.

The products of the present invention may thus be used especially for preventing or treating complaints capable of being modulated by inhibiting the activity of protein kinases.

The inhibition and regulation of protein kinases especially constitute a powerful new mechanism of action for treating a large number of solid or liquid tumours.

Such complaints that the products of the present patent application can treat are thus most particularly solid or liquid tumours.

Such protein kinases belong especially to the following group: EGFR, Fak, FLK-1, FGFR1, FGFR2, FGFR3, FGFR4, FGFR5, flt-1, IGF-1R, KDR, PLK, PDGFR, tie2, VEGFR, AKT, Raf.

The protein kinase IGF1-R (Insulin Growth Factor-1 Receptor) is particularly indicated.

The present invention thus relates particularly to novel inhibitors of the IGF-1R receptor that may be used for oncology treatments.

Cancer remains a disease for which the existing treatments are clearly insufficient. Certain protein kinases, especially including IGF-1R (Insulin Growth Factor 1 Receptor), play an important role in many cancers. The inhibition of such protein kinases is potentially important in the chemotherapy of cancers, especially for suppressing the growth or survival of tumours. The present invention thus relates to the identification of novel products that inhibit such protein kinases.

Protein kinases participate in signalling events that control the activation, growth and differentiation of cells in response either to extracellular mediators or to changes in the environment. In general, these kinases belong to two groups: those that preferentially phosphorylate serine and/or threonine residues and those that preferentially phosphorylate tyrosine residues [S. K. Hanks and T. Hunter, FASEB. J., 1995, 9, pages 576-596]. The serine/threonine kinases are, for example, the isoforms of the protein kinases C [A. C. Newton, J. Biol. Chem., 1995, 270, pages 28495-28498] and a group of cycline-dependent kinases, for instance cdc2 [J. Pines, Trends in Biochemical Sciences, 1995, 18, pages 195-197]. Tyrosine kinases comprise growth factor receptors, for instance the epidermal growth factor (EGF) receptor [S. Iwashita and M. Kobayashi, Cellular Signalling, 1992, 4, pages 123-132], and cytosol kinases, for instance p56tck, p59fYn and ZAP-70 and the kinases csk [C. Chan et. al., Ann. Rev. Immunol., 1994, 12, pages 555-592].

Abnormally high levels of kinase protein activity have been implicated in many diseases, resulting from abnormal cellular functions. This may arise either directly or indirectly from a dysfunction in the mechanisms for controlling the kinase activity, linked, for example, to a mutation, an overexpression or an inappropriate activation of the enzyme, or an over- or underproduction of cytokines or of growth factors, also involved in the transduction of the signals upstream or downstream of the kinases. In all these cases, a selective inhibition of the action of the kinases offers hope of a beneficial effect.

The type 1 receptor for the insulin-like growth factor (IGF-I-R) is a transmembrane receptor with tyrosine kinase activity, which binds firstly to IGFI, but also to IGFII and to insulin with lower affinity. The binding of IGF1 to its receptor results in oligomerization of the receptor, the activation of tyrosine kinase, intermolecular autophosphorylation and the phosphorylation of cell substrates (main substrates: IRS1 and Shc). The receptor activated by its ligand induces mitogenic activity in normal cells. However, IGF-I-R plays an important role in "abnormal" growth.

Several clinical reports underline the important role of the IGF-I route in the development of human cancers:

IGF-I-R is often found overexpressed in many types of tumour (breast, colon, lung, sarcoma, etc.) and its presence is often associated with a more aggressive phenotype.

High concentrations of circulating IGF1 are strongly correlated with a risk of prostate cancer, lung cancer and breast cancer.

Furthermore, it has been widely documented that IGF-I-R is necessary for establishing and maintaining the transformed phenotype in vitro as in vivo [Baserga R, Exp. Cell. Res., 1999, 253, pages 1-6]. The kinase activity of IGF-I-R is essential for the transformation activity of several oncogenes: EGFR, PDGFR, the large T antigen of the SV40 virus, activated Ras, Raf, and v-Src. The expression of IGF-I-R in normal fibroblasts induces a neoplastic phenotype, which may then result in the formation of a tumour in vivo. The expression of IGF-I-R plays an important role in substrate-independent growth. IGF-I-R has also been shown to be a protector in chemotherapy-induced and radiation-induced apoptosis, and cytokine-induced apoptosis. Furthermore, the inhibition of endogenous IGF-I-R with a negative dominant, the formation of a triple helix or the expression of an antisense sequence brings about suppression of the transforming activity in vitro and reduction of tumour growth in animal models.

Among the kinases for which a modulation of the activity is desired, FAK (Focal Adhesion Kinase) is also a preferred kinase.

FAK is a cytoplasmic tyrosine kinase that plays an important role in transducing the signal transmitted by the integrins, a family of heterodimeric receptors of cellular adhesion. FAK and the integrins are colocalized in perimembrane structures known as adhesion plaques. It has been shown in many cell types that the activation of FAK and its phosphorylation on tyrosine residues and in particular its autophosphorylation on tyrosine 397 were dependent on the binding of the integrins to their extracellular ligands and thus induced during cellular adhesion [Kornberg L, et al. J. Biol. Chem. 267(33): 23439-442 (1992)]. The autophosphorylation on tyrosine 397 of FAK represents a binding site for another tyrosine kinase, Src, via its SH2 domain [Schaller et al. Mol. Cell. Biol. 14: 1680-1688 1994; Xing et al. Mol. Cell. Biol. 5: 413-421 1994]. Src can then phosphorylate FAK on tyrosine 925, thus recruiting the adapter protein Grb2 and inducing in certain cells activation of the ras and MAP kinase pathway involved in controlling cellular proliferation [Schlaepfer et al. Nature; 372: 786-791 1994; Schlaepfer et al. Prog. Biophys. Mol. Biol. 71: 435-478 1999; Schlaepfer and Hunter, J. Biol. Chem. 272: 13189-13195 1997].

The activation of FAK can thus induce the jun NH2-terminal kinase (JNK) signalling pathway and result in the progression of the cells to the G1 phase of the cellular cycle [Oktay et al., J. Cell. Biol. 145: 1461-1469 1999]. Phosphatidylinositol-3-OH kinase (PI3-kinase) also binds to FAK on tyrosine 397 and this interaction might be necessary for the activation of PI3-kinase [Chen and Guan, Proc. Nat. Acad. Sci. USA. 91: 10148-10152 1994; Ling et al. J. Cell. Biochem. 73: 533-544 1999]. The FAK/Src complex phosphorylates various substrates, for instance paxillin and p130CAS in fibroblasts [Vuori et al. Mol. Cell. Biol. 16: 2606-2613 1996].

The results of numerous studies support the hypothesis that FAK inhibitors might be useful in treating cancer. Studies have suggested that FAK might play an important role in in vitro cell proliferation and/or survival. For example, in CHO cells, certain authors have demonstrated that the overexpression of p125FAK induces an acceleration of the G1 to S transition, suggesting that p125FAK promotes cellular proliferation [Zhao J.-H et al. J. Cell Biol. 143: 1997-2008 1998]. Other authors have shown that tumour cells treated with FAK antisense oligonucleotides lose their adhesion and go into apoptosis (Xu et al, Cell Growth Differ. 4: 413-418 1996). It has also been demonstrated that FAK promotes the migration of cells in vitro. Thus, fibroblasts that are deficient for the expression of FAK ("knockout" mice for FAK) show a rounded morphology and deficiencies in cell migration in response to chemotactic signals, and these defects are suppressed by re-expression of FAK [D J. Sieg et al., J. Cell Science. 112: 2677-91 1999]. The overexpression of the C-terminal domain of FAK (FRNK) blocks the stretching of adherent cells and reduces cellular migration in vitro [Richardson A. and Parsons J. T. Nature. 380: 538-540 1996]. The overexpression of FAK in CHO or COS cells or in human astrocytoma cells promotes migration of the cells. The involvement of FAK in promoting the proliferation and migration of cells in numerous cell types in vitro suggests the potential role of FAK in neoplastic processes. A recent study has effectively demonstrated the increase in the proliferation of tumour cells in vivo after induction of the expression of FAK in human astrocytoma cells [Cary L. A. et al. J. Cell Sci. 109: 1787-94 1996; Wang D et al. J. Cell Sci. 113: 4221-4230 2000]. Furthermore, immunohistochemical studies on human biopsies have demonstrated that FAK is overexpressed in prostate cancer, breast cancer, thyroid cancer, cancer of the colon, melanoma, brain cancer and lung cancer, the level of expression of FAK being directly correlated to the tumours having the most aggressive phenotype [Weiner T M, et al. Lancet. 342 (8878): 1024-1025 1993; Owens et al. Cancer Research. 55: 2752-2755 1995; Maung K. et al. Oncogene 18: 6824-6828 1999; Wang D et al. J. Cell Sci. 113: 4221-4230 2000].

Protein kinase AKT (also known as PKB) and phosphoinositide 3-kinase (PI3K) are involved in a cell signalling pathway that transmits signals from growth factors activating membrane receptors.

This transduction pathway is involved in numerous cellular functions: regulation of apoptosis, control of transcription and translation, glucose metabolism, angiogenesis and mitochondrial integrity. First identified as an important component of insulin-dependent signalling pathways regulating metabolic responses, serine/threonine kinase AKT was then identified as a mediator playing a key role in survival induced with growth factors. It has been shown that AKT can inhibit death by apoptosis induced by various stimuli, in a certain number of cell types and tumour cells. In accordance with these findings, it has been shown that AKT can, by phosphorylation of given serine residues, inactivate BAD, GSK3β, caspase-9, and Forkhead transcription factor, and can activate IKKalpha and e-NOS. It is interesting to note that the protein BAD is found hyper-phosphorylated in 11 human tumour cell lines out of 41 studied. Furthermore, it has been shown that hypoxia modulates the induction of VEGF in cells transformed with Ha-ras by activating the PI3K/AKT pathway and by involving the binding sequence of the HIF-1 (hypoxia inducible factor-1) transcription factor known as HRE for "hypoxy-responsive element".

AKT plays a very important role in cancer pathologies. The amplification and/or overexpression of AKT has been reported in many human tumours, for instance gastric carcinoma (amplification of AKT1), ovary carcinoma, breast carcinoma or pancreatic carcinoma (amplification and overexpression of AKT2) and breast carcinomas deficient in oestrogen receptors, and also androgen-independent prostate carcinomas (overexpression of AKT3). Furthermore, AKT is constitutively activated in all the PTEN (−/−) tumours, the PTEN phosphatase being deleted or inactivated by mutations in many types of tumours, for instance carcinomas of the ovary, of the prostate, of the endometrium, glioblastomas and melanomas. AKT is also involved in the oncogenic activation of bcr-abl (references: Khawaja A., Nature 1999, 401, 33-34; Cardone et al. Nature 1998, 282, 1318-1321; Kitada S. et al., Am J Pathol 1998 January; 152(1): 51-61; Mazure N M et al. Blood 1997, 90, 3322-3331; Zhong H. et al. Cancer Res. 2000, 60, 1541-1545).

One subject of the present invention is thus the products of general formula (I):

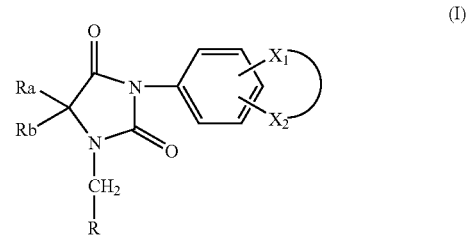

in which:
Ra and Rb represent CH3 or form, together with the carbon atom to which they are attached, a cycloalkyl radical,
X1 and X2 are such that:
either one represents hydrogen and the other represents alkyl, or one represents —OCF3 or —SCF3 and the other represents the radical NH—CO—R6,
or $X_1$ and $X_2$ form, with the phenyl radical to which they are attached, a dihydroindole radical optionally substituted with one or more alkyl radicals and on its nitrogen atom with a radical CO-alkyl-R3,
R represents a pyridyl or pyrimidinyl radical substituted with a radical NR1R2,
NR1R2 being such that:
one from among R1 and R2 represents a hydrogen atom or an alkyl radical, and the other from among R1 and R2 is chosen from a hydrogen atom and alkyl radicals optionally substituted with a radical chosen from hydroxyl, alkoxy, aziridyl, azetidinyl, pyrrolidinyl, piperidyl, morpholinyl, and piperazinyl, which is itself optionally substituted on its second nitrogen atom with an alkyl radical; optionally substituted cycloalkyl, heterocycloalkyl, aryl and heteroaryl radicals; and the radical CO—R3 with R3 chosen from NR4R5 and optionally substituted alkoxy, heterocycloalkyl, aryl, aryloxy and heteroaryl radicals;
R4 and R5, which may be identical to or different from R1 and R2, are such that:
either one from among R4 and R5 represents a hydrogen atom or an alkyl radical, and the other from among R4 and R5 is chosen from a hydrogen atom and alkyl radicals optionally substituted with a radical chosen from hydroxyl, alkoxy, aziridyl, azetidinyl, pyrrolidinyl, piperidyl, morpholinyl, and piperazinyl, which is itself optionally substituted on its second nitrogen atom with an alkyl radical; optionally substituted cycloalkyl, heterocycloalkyl, aryl and heteroaryl radicals;

or R4 and R5 form, with the nitrogen atom to which they are attached, a cyclic amine optionally containing another heteroatom chosen from N and O, which is optionally substituted, all the above aryl, phenyl, aryloxy and heteroaryl radicals, and also the cyclic amine NR4R5, being optionally substituted with one to three radicals, which may be identical or different, chosen from halogen atoms and alkyl, phenyl, NH2, NHAlk, N(Alk)2, CO—NHAlk and CO—N(Alk)2 radicals;

R6 represents alkyl optionally substituted with one or more radicals, which may be identical or different, chosen from the values of R3, the said products of formula (I) being in any possible racemic, enantiomeric or diastereoisomeric isomer form, and also the addition salts with mineral and organic acids or with mineral and organic bases of the said products of formula (I).

It may be noted that when Ra and Rb, together with the carbon atom to which they are attached, form a cycloalkyl radical, this radical is especially cyclopropyl.

A subject of the present invention is thus the products of formula (I) as defined above:

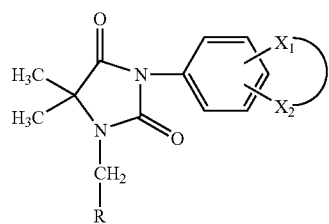

(I)

in which:
Ra and Rb represent CH3,
X1 and X2 have the meaning given in claim 1,
R represents a pyridyl or pyrimidinyl radical substituted with a radical NR1R2,
NR1R2 being such that:
one from among R1 and R2 represents a hydrogen atom or an alkyl radical, and the other from among R1 and R2 is chosen from a hydrogen atom and alkyl radicals optionally substituted with a radical chosen from hydroxyl, alkoxy, aziridyl, azetidinyl, pyrrolidinyl, piperidyl, morpholinyl, or piperazinyl, which is itself optionally substituted on its second nitrogen atom with an alkyl radical; optionally substituted cycloalkyl, heterocycloalkyl, phenyl, pyrimidinyl and pyridyl radicals; and the radical CO—R3 with R3 chosen from NR4R5 and optionally substituted alkoxy, piperidyl, phenyl and phenoxy radicals;
R4 and R5, which may be identical to or different from R1 and R2, are such that:
either one from among R4 and R5 represents a hydrogen atom or an alkyl radical, and the other from among R4 and R5 is chosen from a hydrogen atom and alkyl radicals optionally substituted with a radical chosen from hydroxyl, alkoxy, aziridyl, azetidinyl, pyrrolidinyl, piperidyl, morpholinyl, or piperazinyl, which is itself optionally substituted on its second nitrogen atom with an alkyl radical; optionally substituted cycloalkyl, heterocycloalkyl, phenyl, pyrimidinyl and pyridyl radicals;

or R4 and R5 form, with the nitrogen atom to which they are attached, a cyclic amine optionally containing another heteroatom chosen from N and O, which is optionally substituted, all the above phenyl, pyrimidinyl and pyridyl radicals being optionally substituted with one to three radicals, which may be identical or different, chosen from halogen atoms and alkyl, phenyl, NH2, NHAlk, N(Alk)2, CO—NHAlk and CO—N(Alk)2 radicals; the said products of formula (I) being in any possible racemic, enantiomeric and diastereoisomeric isomer form, and also the addition salts with mineral and organic acids or with mineral and organic bases of the said products of formula (I).

In the products of formula (I) and hereinbelow, the terms indicated have the following meanings:

the term "Hal", "Halo" or halogen denotes fluorine, chlorine, bromine or iodine atoms, and preferably fluorine and chlorine, the term "alkyl" or "alk" denotes a linear or branched radical containing not more than 12 carbon atoms, chosen from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl and dodecyl radicals, and also the linear or branched positional isomers thereof.

Mention is made more particularly of alkyl radicals containing not more than 6 carbon atoms, and especially methyl, ethyl, propyl, isopropyl, n-butyl, isobutyl, tert-butyl, linear or branched pentyl and linear or branched hexyl radicals.

the term "alkoxy radical" denotes a linear or branched radical containing not more than 12 carbon atoms and preferably 6 carbon atoms chosen, for example, from methoxy, ethoxy, propoxy, isopropoxy, linear, secondary or tertiary butoxy, pentoxy, hexoxy and heptoxy radicals, and also the linear or branched positional isomers thereof, the term "cycloalkyl radical" denotes a 3- to 10-membered monocyclic or bicyclic carbocyclic radical and especially denotes cyclopropyl, cyclobutyl, cyclopentyl and cyclohexyl radicals, the term "acyl radical" or —CO-r denotes a linear or branched radical containing not more than 12 carbon atoms, in which the radical r represents a hydrogen atom or an alkyl, cycloalkyl, cycloalkenyl, cycloalkyl, heterocycloalkyl or aryl radical, these radicals having the values indicated above and being optionally substituted as indicated: examples that are mentioned include the formyl, acetyl, propionyl, butyryl or benzoyl radical, or alternatively valeryl, hexanoyl, acryloyl, crotonoyl or carbamoyl. It is noted that the radical CO—R3 can especially take the values defined above for —CO-r, the term "aryl radical" denotes unsaturated monocyclic radicals or unsaturated radicals consisting of fused carbocyclic rings. Examples of such aryl radicals that may be mentioned include phenyl or naphthyl radicals.

Mention is made more particularly of the phenyl radical.

The aryloxy radical denotes a radical —O-aryl in which the aryl radical has the meaning indicated above.

The term "heterocycloalkyl radical" denotes a saturated carbocyclic radical which is not more than 7-membered, interrupted with one or more heteroatoms, which may be identical or different, chosen from oxygen, nitrogen and sulphur atoms: heterocycloalkyl radicals that may especially be mentioned include dioxolane, dioxane, dithiolane, thiooxolane, thiooxane, oxiranyl, oxolanyl, dioxolanyl, piperazinyl, piperidyl, pyrrolidinyl, imidazolidinyl, pyrazolidinyl, morpholinyl, or tetrahydrofuryl, tetrahydrothienyl, chromanyl, dihydrobenzofuryl, indolinyl, piperidyl, perhydropyranyl, pyrindolinyl, tetrahydroquinolyl, tetrahydroisoquinolyl and thioazolidinyl radicals, all these radicals being optionally substituted.

Among the heterocycloalkyl radicals that may especially be mentioned are optionally substituted piperazinyl, optionally substituted piperidyl, optionally substituted pyrrolidinyl, imidazolidinyl, pyrazolidinyl, morpholinyl and thioazolidinyl radicals.

The term "heteroaryl radical" denotes a partially or totally unsaturated carbocyclic radical which is not more than 7-membered, interrupted with one or more heteroatoms, which may be identical or different, chosen from oxygen, nitrogen and sulphur atoms; among the 5-membered heteroaryl radicals that may be mentioned are furyl radicals such as 2-furyl, thienyl radicals such as 2-thienyl and 3-thienyl, and pyrrolyl, diazolyl, thiazolyl, thiadiazolyl, thiatriazolyl, isothiazolyl, oxazolyl, oxadiazolyl, 3- or 4-isoxazolyl, imidazolyl, pyrazolyl and isoxazolyl radicals. Among the 6-membered heteroaryl radicals that may especially be mentioned are pyridyl radicals such as 2-pyridyl, 3-pyridyl and 4-pyridyl, and pyrimidyl, pyrimidinyl, pyridazinyl, pyrazinyl and tetrazolyl radicals.

as fused heteroaryl radicals containing at least one hetero atom chosen from sulphur, nitrogen and oxygen, examples that may be mentioned include benzothienyl such as 3-benzothienyl, benzofuryl, benzofuryl, benzopyrrolyl, benzimidazolyl, benzoxazolyl, thionaphthyl, indolyl, purinyl, quinolyl, isoquinolyl and naphthyridinyl.

Among the fused heteroaryl radicals that may be mentioned more particularly are benzothienyl, benzofuryl, indolyl, quinolyl, benzimidazolyl, benzothiazolyl, furyl, imidazolyl, indolizinyl, isoxazolyl, isoquinolyl, isothiazolyl, oxadiazolyl, pyrazinyl, pyridazinyl, pyrazolyl, pyridyl, pyrimidinyl, pyrrolyl, quinazolinyl, 1,3,4-thiadiazolyl, thiazolyl and thienyl radicals and triazolyl groups, these radicals optionally being substituted as indicated for the heteroaryl radicals.

The term "patient" denotes human beings, but also other mammals.

The term "prodrug" denotes a product that may be converted in vivo via metabolic mechanisms (such as hydrolysis) into a product of formula (I). For example, an ester of a product of formula (I) containing a hydroxyl group may be converted by hydrolysis in vivo into its parent molecule. Alternatively, an ester of a product of formula (I) containing a carboxyl group may be converted by in vivo hydrolysis into its parent molecule.

Examples of esters of the products of formula (I) containing a hydroxyl group that may be mentioned include the acetates, citrates, lactates, tartrates, malonates, oxalates, salicylates, propionates, succinates, fumarates, maleates, methylenebis-β-hydroxynaphthoates, gentisates, isethionates, di-p-tolyltartrates, methanesulphonates, ethanesulphonates, benzenesulphonates, p-toluenesulphonates, cyclohexylsulphamates and quinates.

Esters of products of formula (I) that are particularly useful, containing a hydroxyl group, may be prepared from acid residues such as those described by Bundgaard et al., J. Med. Chem., 1989, 32, pp. 2503-2507: these esters especially include substituted (aminomethyl)benzoates, dialkylaminomethylbenzoates in which the two alkyl groups may be linked together or may be interrupted with an oxygen atom or with an optionally substituted nitrogen atom, i.e. an alkylated nitrogen atom, or alternatively (morpholinomethyl)benzoates, e.g. 3- or 4-(morpholinomethyl)benzoates, and (4-alkylpiperazin-1-yl)benzoates, e.g. 3- or 4-(4-alkylpiperazin-1-yl)benzoates.

The carboxyl radical(s) of the products of formula (I) may be salified or esterified with various groups known to those skilled in the art, among which nonlimiting examples that may be mentioned include the following compounds:

among the salification compounds, mineral bases such as, for example, one equivalent of sodium, potassium, lithium, calcium, magnesium or ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine or N-methylglucamine, among the esterification compounds, alkyl radicals to form alkoxycarbonyl groups such as, for example, methoxycarbonyl, ethoxycarbonyl, tert-butoxycarbonyl or benzyloxycarbonyl, these alkyl radicals possibly being substituted with radicals chosen, for example, from halogen atoms and hydroxyl, alkoxy, acyl, acyloxy, alkylthio, amino or aryl radicals, such as, for example, in chloromethyl, hydroxypropyl, methoxymethyl, propionyloxymethyl, methylthiomethyl, dimethylaminoethyl, benzyl or phenethyl groups.

The term "esterified carboxyl" means, for example, radicals such as alkyloxycarbonyl radicals, for example methoxycarbonyl, ethoxycarbonyl, propoxycarbonyl, butyl or tert-butyloxycarbonyl, cyclobutyloxycarbonyl, cyclopentyloxycarbonyl or cyclohexyloxycarbonyl.

Mention may also be made of radicals formed with readily cleavable ester residues, such as methoxymethyl or ethoxymethyl radicals; acyloxyalkyl radicals such as pivaloyloxymethyl, pivaloyloxyethyl, acetoxymethyl or acetoxyethyl; alkyloxycarbonyloxyalkyl radicals such as methoxycarbonyloxy methyl or ethyl radicals, and isopropyloxycarbonyloxy methyl or ethyl radicals.

A list of such ester radicals may be found, for example, in European patent EP 0 034 536.

The term "amidated carboxyl" means radicals of the type —CONR4R5 in which the radicals R4 and R5 have the meanings indicated above.

The term "alkylamino radical" NHalk means linear or branched methylamino, ethylamino, propylamino or butylamino radicals. Alkyl radicals containing not more than 4 carbon atoms are preferred, the alkyl radicals possibly being chosen from the alkyl radicals mentioned above.

The term "dialkylamino radical" N(alk)2 means radicals in which alk takes the values defined above: as previously, alkyl radicals containing not more than 4 carbon atoms, chosen from the list indicated above, are preferred. Examples that may be mentioned include dimethylamino, diethylamino and methylethylamino radicals.

The term "cyclic amine" denotes a 3- to 8-membered cycloalkyl radical in which a carbon atom is replaced with a nitrogen atom, the cycloalkyl radical having the meaning indicated above and also possibly containing one or more other heteroatoms chosen from O, S, SO2, N and NR3 with R3 as defined above: examples of such cyclic amines that may be mentioned include optionally substituted aziridyl, azetidinyl, pyrrolidinyl, piperidyl, morpholinyl, piperazinyl, indolinyl, pyrindolinyl and tetrahydroquinolyl radicals: mention is made more particularly of pyrrolidinyl, piperidyl and morpholinyl radicals.

The term "salified carboxyl" means the salts formed, for example, with one equivalent of sodium, potassium, lithium, calcium, magnesium or ammonium. Mention may also be made of the salts formed with organic bases such as methylamine, propylamine, trimethylamine, diethylamine and triethylamine. The sodium salt is preferred.

When the products of formula (I) comprise an amino radical that may be salified with an acid, it is clearly understood that these acid salts also form part of the invention. Mention may be made of the salts obtained, for example, with hydrochloric acid or methanesulphonic acid.

The addition salts with mineral or organic acids of the products of formula (I) may be, for example, the salts formed with hydrochloric acid, hydrobromic acid, hydriodic acid, nitric acid, sulphuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulphonic acids such as, for example, methanesulphonic acid, ethanesulphonic acid or propanesulphonic acid, alkyldisulphonic acids such as, for example, methanedisulphonic acid or alpha,beta-ethanedisulphonic acid, arylmonosulphonic acids such as benzenesulphonic acid, and aryldisulphonic acids.

It may be recalled that stereoisomerism may be defined in its broad sense as the isomerism of compounds having the same structural formulae but whose various groups are arranged differently in space, especially such as in monosubstituted cyclohexanes whose substituent may be in an axial or equatorial position, and the various possible rotational conformations of ethane derivatives.

However, there is another type of stereoisomerism, due to the different spatial arrangements of fixed substituents, either on double bonds or on rings, which is often referred to as geometrical isomerism or cis-trans isomerism. The term "stereoisomer" is used in the present patent application in its broadest sense and thus relates to all the compounds indicated above.

A subject of the present invention is thus the products of formula (I) as defined above, in which:
X1 and X2 are such that:
either one represents hydrogen and the other represents an alkyl radical,
or one represents —OCF3 or —SCF3 and the other represents the radical NH—CO—R6,
or X1 and X2 form, with the phenyl radical to which they are attached, a dihydroindole radical optionally substituted with one or more alkyl radicals and on its nitrogen atom with a radical CO—CH2-NH-cycloalkyl,
R represents a pyridyl or pyrimidinyl radical substituted with a radical NR1R2,
NR1R2 being such that R1 represents a hydrogen atom or an alkyl radical, and R2 is chosen from a hydrogen atom and alkyl radicals optionally substituted with a hydroxyl, aziridyl, azetidinyl, pyrrolidinyl, piperidyl, morpholinyl, or piperazinyl, which is itself optionally substituted on its second nitrogen atom with an alkyl radical; 3- to 6-membered cycloalkyl radicals; an optionally substituted phenyl radical; a pyrimidinyl radical; a pyridyl radical optionally substituted with a halogen atom; and the radical CO—R3 with R3 chosen from NR4R5 and optionally substituted alkoxy, piperidyl and phenyl radicals;
R4 and R5, which may be identical to or different from R1 and R2, are such that:
either one from among R4 and R5 represents a hydrogen atom or an alkyl radical, and the other from among R4 and R5 is chosen from a hydrogen atom and alkyl radicals optionally substituted with a hydroxyl, aziridyl, azetidinyl, pyrrolidinyl, piperidyl, morpholinyl, or piperazinyl, which is itself optionally substituted on its second nitrogen atom with an alkyl radical; 3- to 6-membered cycloalkyl radicals; an optionally substituted phenyl radical; a pyrimidinyl radical; a pyridyl radical optionally substituted with a halogen atom;
or R4 and R5 form, with the nitrogen atom to which they are attached, an aziridyl, azetidinyl, pyrrolidinyl, piperidyl, morpholinyl, or piperazinyl, which is itself optionally substituted on its second nitrogen atom with an alkyl radical, all the phenyl radicals being optionally substituted with one to three radicals, which may be identical or different, chosen from halogen atoms, alkyl radicals and radicals CO—NHAlk and CO—N(Alk)2;
with R6 representing alkyl optionally substituted with one or more radicals, which may be identical or different, chosen from the values of R3
the said products of formula (I) being in any possible racemic, enantiomeric or diastereoisomeric isomer form, and also the addition salts with mineral and organic acids or with mineral and organic bases of the said products of formula (I).

A subject of the present invention is thus the products of formula (I) as defined above in which
X1 and X2 are such that:
either one represents hydrogen and the other represents a tert-butyl radical,
or one represents —OCF3 or —SCF3 and the other represents the radical —NH—CO—CH(NH2)-phenyl,
or X1 and X2 form, with the phenyl radical to which they are attached, a dihydroindole radical substituted with two methyl radicals and on its nitrogen atom with a radical CO—CH2-NH-cyclopentyl,
R represents a pyridyl or pyrimidinyl radical substituted with a radical NR1R2,
NR1R2 being such that R1 represents a hydrogen atom or an alkyl radical containing one or two carbon atoms, and R2 is chosen from alkyl radicals containing 1 to 4 carbon atoms optionally substituted with a hydroxyl radical; an optionally substituted phenyl radical; a pyrimidinyl radical; a pyridyl radical optionally substituted with a halogen atom; and the radical CO—R3 with R3 chosen from piperidyl, optionally substituted phenyl, NH-cycloalkyl, NH2, NH(alk) and N(alk)2; all the phenyl radicals being optionally substituted with one to three radicals, which may be identical or different, chosen from halogen atoms and alkyl radicals and radicals CO—NHAlk and CO—N(Alk)2;
the said products of formula (I) being in any possible racemic, enantiomeric or diastereoisomeric isomer form, and also the addition salts with mineral and organic acids or with mineral and organic bases of the said products of formula (I).

A subject of the present invention is thus the products of formula (I) as defined above in which:
X1 and X2 have the meanings given in any one of the preceding claims
R represents a pyridyl or pyrimidinyl radical substituted with a radical NR1R2 in which R1 represents a hydrogen atom and R2 represents a pyrimidinyl or pyridyl radical; or a radical CO—N(CH3)2;
the said products of formula (I) being in any possible racemic, enantiomeric or diastereoisomeric isomer form, and also the addition salts with mineral and organic acids or with mineral and organic bases of the said products of formula (I).

A subject of the present invention is especially the products of formula (I) as defined above in which X1, X2, Ra, Rb and R have any of the meanings given above, and the radicals NR1R2 or NR4R5 or alternatively NR1R2 and NR4R5 are chosen from the following radicals named ex 9 to ex 31:

ex 9
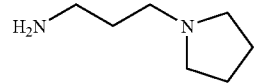

ex 10
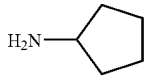

ex 11
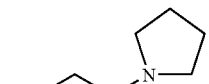

ex 12
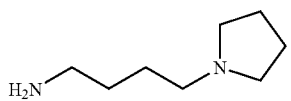

ex 13
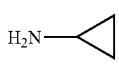

ex 14
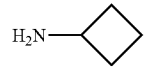

ex 15
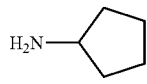

ex 16

ex 17

ex 18

ex 19

ex 20
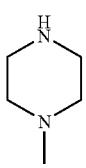

ex 21 ex 22
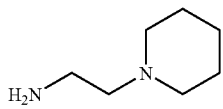

ex 23
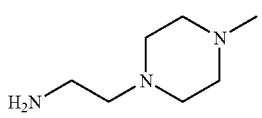

ex 24
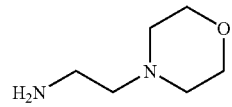

ex 25
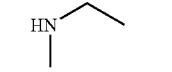

ex 26
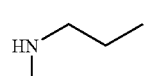

ex 27
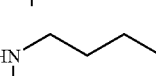

ex 28
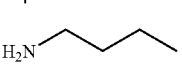

ex 29
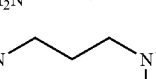

ex 30 ex 31
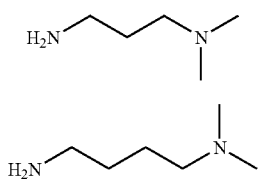

the said products of formula (I) being in any possible racemic, enantiomeric or diastereoisomeric isomer form, and also the addition salts with mineral and organic acids or with mineral and organic bases of the said products of formula (I).

A subject of the present invention is especially the products of formula (I) as defined above in which the radical NR1R2 is chosen from the values ex 9 to ex 31 as defined above.

A subject of the present invention is especially the products of formula (I) as defined above belonging to formula (Ia):

(Ia)
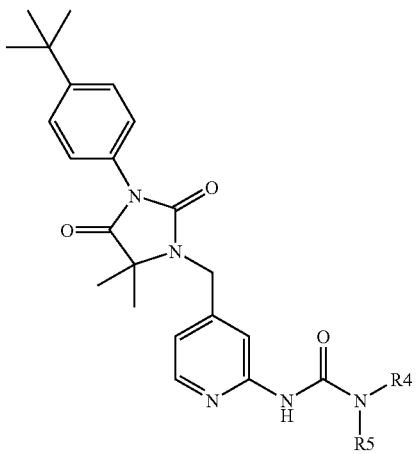

in which n and NR4R5 have any of the definitions given above and especially NR4R5 may represent the radicals ex 9 to ex 31, the said products of formula (Ia) being in any possible racemic, enantiomeric or diastereoisomeric isomer form, and also the addition salts with mineral and organic acids or with mineral and organic bases of the said products of formula (Ia).

Among the preferred products of the invention, mention may be made more specifically of the products of formula (I) as defined above, whose names are as follows:

3-(4-tert-butylphenyl)-5,5-dimethyl-1-[2-(pyridin-3-ylamino)pyrimidin-4-ylmethyl]imidazolidine-2,4-dione 3-(4-{[3-(4-tert-butylphenyl)-5,5-dimethyl-2,4-dioxoimidazolidin-1-yl]methyl}pyrimidin-2-yl)-1,1-dimethylurea 3-[4-({3-[1-(N-cyclopentylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea 3-[1-(N-cyclopentylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione (2R)-2-amino-N-[5-(4,4-dimethyl-2,5-dioxo-3-{[2-(pyridin-3-ylamino)pyridin-4-yl]methyl}imidazolidin-1-yl)-2-(trifluoromethoxy)phenyl]-2-phenylacetamide (2R)-2-amino-N-{5-(4,4-dimethyl-2,5-dioxo-3-{[2-(pyridin-3-ylamino)pyridin-4-yl]methyl}imidazolidin-1-yl)-2-[(trifluoromethyl)thio]phenyl}-2-phenylacetamide (2R)-2-amino-N-{5-[3-({2-[(dimethylcarbamoyl)amino]pyridin-4-yl}methyl)-4,4-dimethyl-2,5-dioxoimidazolidin-1-yl]-2-(trifluoromethoxy)phenyl}-2-phenylacetamide (2R)-2-amino-N-{5-[3-({2-[(dimethylcarbamoyl)amino]pyridin-4-yl}methyl)-4,4-dimethyl-2,5-dioxoimidazolidin-1-yl]-2-[(trifluoromethyl)thio]phenyl}-2-phenylacetamide 3-(4-tert-butylphenyl)-5,5-dimethyl-1-{[2-(pyrimidin-5-ylamino)pyridin-4-yl]methyl}imidazolidine-2,4-dione 3-(4-tert-butylphenyl)-5,5-dimethyl-1-{[2-(pyrimidin-5-ylamino)pyrimidin-4-yl]methyl}imidazolidine-2,4-dione the said products of formula (I) being in any possible racemic, enantiomeric or diastereoisomeric isomer form, and also the addition salts with mineral and organic acids or with mineral and organic bases of the said products of formula (I).

The products of formula (I) according to the present invention may be prepared according to the usual methods known to those skilled in the art.

The products of formula (I) according to the present invention may be prepared by application or adaptation of known methods and especially of the methods described in the literature, for instance those described by R. C. Larock in: Comprehensive Organic Transformations, VCH publishers, 1989.

The products according to the present invention may especially be prepared as indicated in the synthetic schemes described below: Scheme for preparation of intermediates and 4 General Synthetic Schemes: General Scheme 1, General Scheme 2, General Scheme 3 and General Scheme 4 below.

The preparations of the examples of the present invention give illustrations of the Schemes below.

Such synthetic schemes form part of the present invention: a subject of the present invention is thus also the processes for preparing the products of formula (I) as defined in General Scheme 1, General Scheme 2, General Scheme 3 and General Scheme 4 below.

A subject of the present invention is also the process for preparing intermediates as defined below.

Scheme for preparation of intermediates:

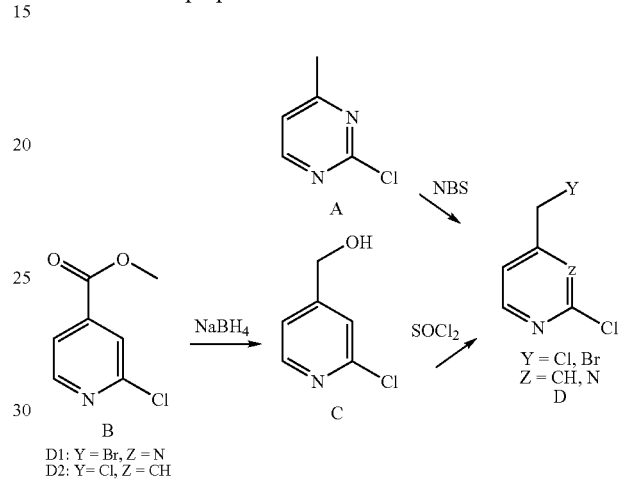

In the Scheme for preparation of intermediates:

The product D1 may be prepared by bromination of product A in the presence of N-bromosuccinimide in a solvent such as carbon tetrachloride, as described by Brown, D. J. et al. (Aust. J. Chem. (1974), 2251).

The alcohol C may be prepared by reduction of the ester B with a reducing agent such as sodium borohydride in a solvent such as ethanol at a temperature of between 20° C. and the reflux temperature of the solvent, as described by Zanka, A. et al. (Synlett (1999), (10), 1636-1638).

The product D2 is prepared by chlorination of the alcohol C as under conditions described by Fucase K. et al. (Tetrahedron Lett, 1991, 32(32), 4019-4022) by treatment with thionyl chloride in the presence of DMF in a solvent such as dichloromethane at a temperature of between 0° C. and 20° C.

General Scheme 1:

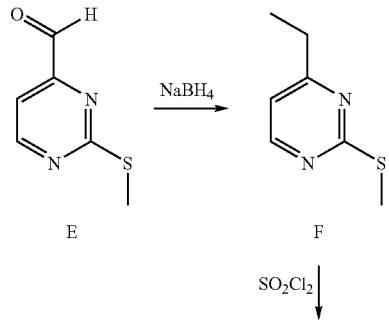

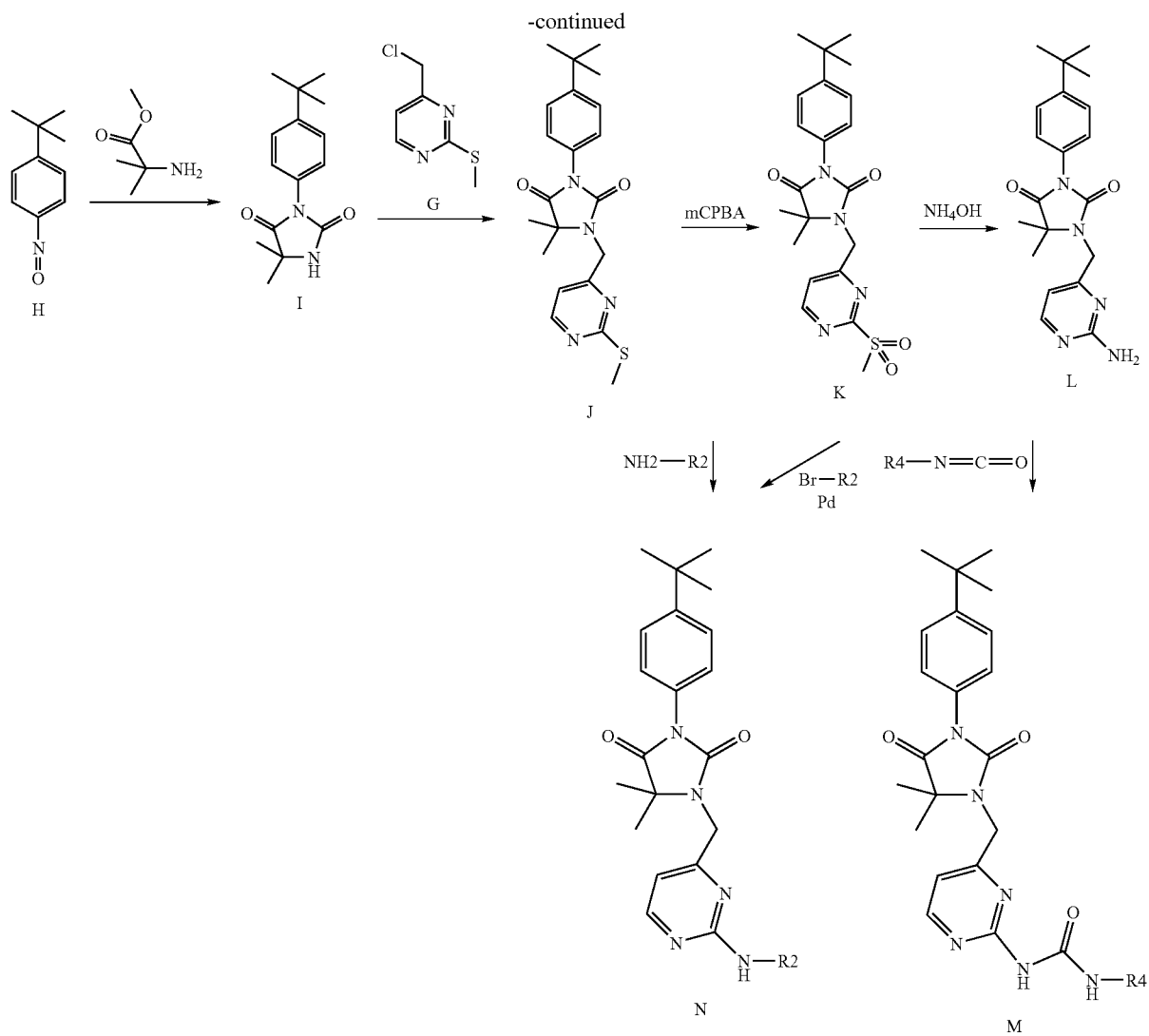

In General Scheme 1:

The alcohol F may be obtained by treating the aldehyde E with a reducing agent such as sodium borohydride, in a solvent such as methanol at a temperature of between 0° C. and 60° C., for instance under the conditions described by Wang, E. et al. (Heterocycles 2002, 57(11), 2021-2033).

The chlorinated product G may be obtained from the alcohol F, for instance under the conditions described for preparation of the product D2.

The hydantoin I may be obtained from the isocyanate H by reaction with methyl 2,2-dimethyl glycinate in a solvent such as toluene or N,N-dimethylformamide at a temperature of between 20° C. and the reflux temperature of the solvent, as described, for example, by Brana M. F. (J. Het. Chem. (2002), 39(2), 417-420.

The product J may be prepared by reacting the products I and G with sodium hydride in tetrahydrofuran or N,N-dimethylformamide at a temperature of between 0° C. and 60° C., as described by Johnson T. A. et al. (J. Am. Chem. Soc. (2002), 124, 11689-11698).

The product of general formula K may be prepared by reacting J with meta-chloroperbenzoic acid in solvents such as a dichloromethane/methanol mixture (90:10; v/v) or 1,2-dichloroethane at temperatures of between 0° C. and 60° C. as described by Jeong, I. H. et al. (Bull. Korean Chem. Soc. (2002), 23 (12), 1823-1826).

The products of general formula L may be prepared by reacting K with ammonia dissolved in water and/or dioxane in a sealed microwave tube or by heating to temperatures of between 40° C. and 150° C., as described by Font, D. et al. (Synthesis (2002), (13), 1833-1842).

The products of general formula M may be obtained by reacting L with an isocyanate (R4-N=C=O) using the usual methods known to those skilled in the art.

The products of formula N may be prepared either by reacting k with an amine (R2NH2) dissolved in dioxane in a sealed microwave tube or by heating to temperatures of between 40° C. and 150° C., as described in the preparation of compound L.

Or starting with L by reaction with an aryl or heteroaryl bromide (R2-Br) in the presence of a palladium-based catalyst such as palladium acetate and a ligand such as xantphos in a solvent such as toluene, dioxane or tert-butanol, for instance under the conditions described Buchwald, S. L. et al. (J. Org. Chem. 2001, 66 (8), 2560-2565).

General Scheme 2:

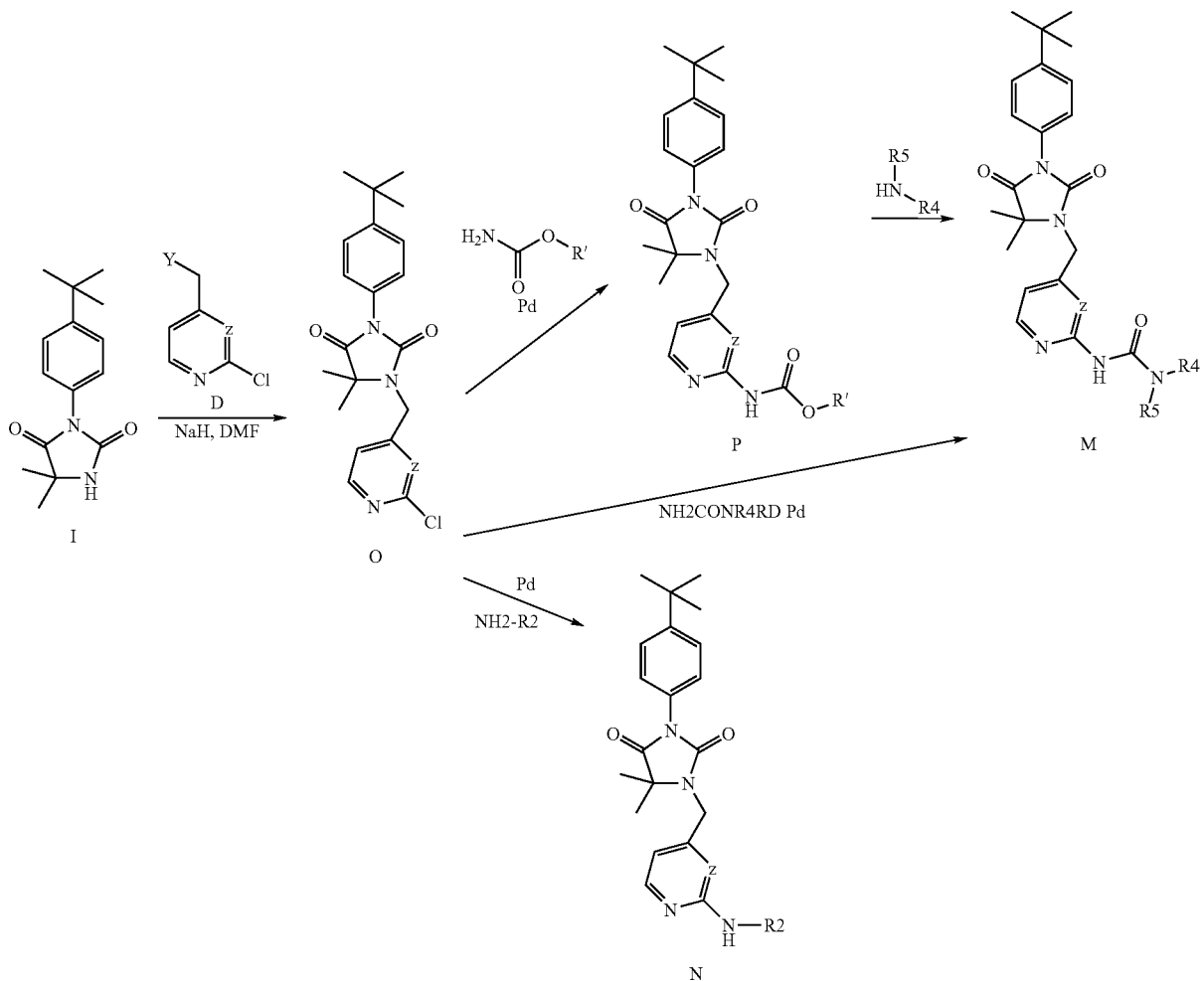

In General Scheme 2:

Products O may be prepared by reacting products I and D with sodium hydride in tetrahydrofuran or N,N-dimethylformamide at a temperature of between 0° C. and 60° C. as described in the preparation of compound J.

Product P may be prepared from 0 by reaction with a carbamate (NH2COOR') in the presence of a palladium-based catalyst such as palladium acetate and a ligand such as xantphos in a solvent such as toluene, dioxane or tert-butanol, for instance under the conditions described by Buchwald, S. L. et al. (J. Org. Chem. 2001, 66 (8), 2560-2565).

Product M may be prepared
either by reacting the carbamate P with an amine in a solvent such as N-methylpyrrolidinone or toluene at a temperature of between 50° C. and the reflux temperature of the solvent or by microwave, as described by Manov-Yuvenskii V. I et al. (Zh. Prikl. Khim. (1993), 66 (6), 1319-1327).
or starting with O by reaction with a urea (NH2CONR4R5) in the presence of a palladium-based catalyst such as palladium acetate and a ligand such as xantphos in a solvent such as toluene, dioxane or tert-butanol, for instance under the conditions described by Buchwald, S. L. et al. (J. Org. Chem. 2001, 66 (8), 2560-2565).

Product N may be prepared from 0 by reaction with an amine (R2-NH2) in the presence of a palladium-based catalyst such as palladium acetate and a ligand such as xantphos in a solvent such as toluene, dioxane or tert-butanol, for instance under the conditions described by Buchwald, S. L. et al. (J. Org. Chem. 2001, 66 (8), 2560-2565).

General Scheme 2a:

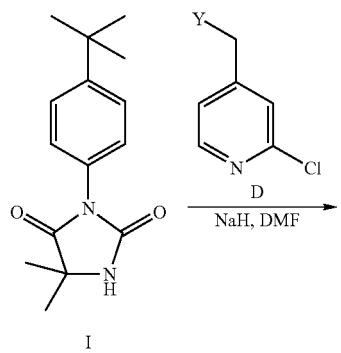

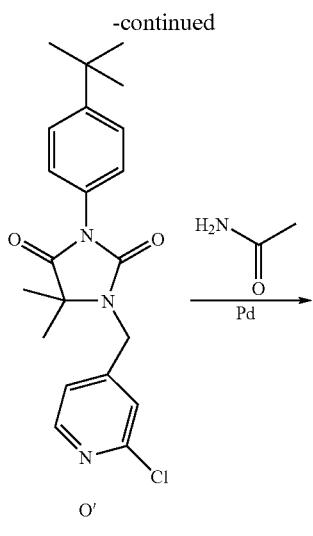

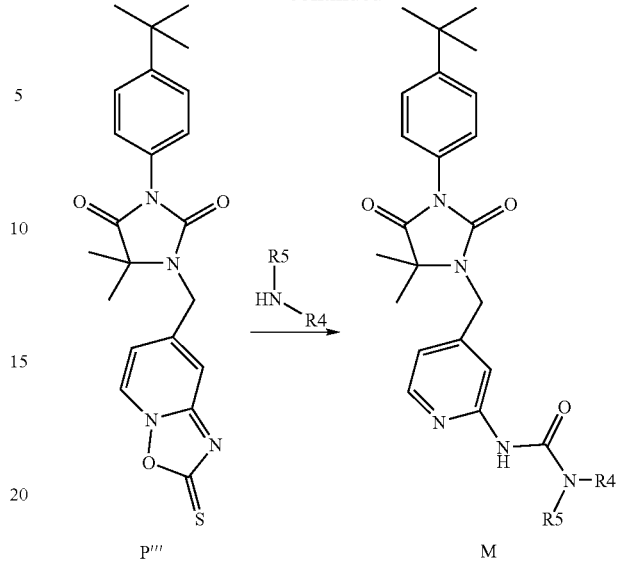

Product M may also be prepared according to the synthesis described in General Scheme 2a:

Product O' may be prepared by reacting products I and D with sodium hydride in tetrahydrofuran or N,N-dimethylformamide at a temperature of between 0° C. and 60° C. as described in General Scheme 2 product O.

Product P' may be prepared from O' by reaction with acetamide (NH2COCH3) in the presence of a palladium-based catalyst such as palladium acetate and a ligand such as xantphos in a solvent such as toluene, dioxane or tert-butanol, for instance under the conditions described by Buchwald, S. L. et al. (J. Am. Chem. Soc. 2002, 124, 6043-6048).

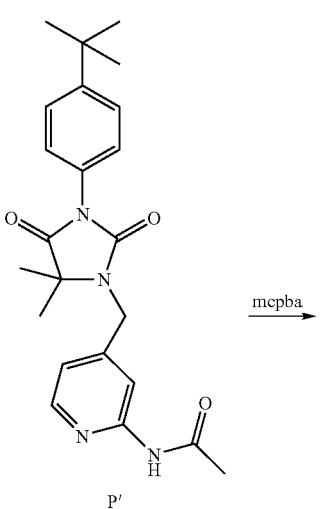

Product P'' may be prepared by oxidation of P' with an oxidizing agent such as meta-chloroperbenzoic acid in a solvent such as dichloromethane, for instance under the conditions described by Sollogoub, M. et al. (Tet. Lett. 2002, 43 (17), 3121-3123).

Product P''' may be obtained by treating product P'' with thiophosgene in the presence of a base such as sodium hydrogen carbonate in a solvent such as ethanol, for instance under the conditions described by Rousseau, D. et al. (Can. J. Chem. 1977, 55, 3736-3739).

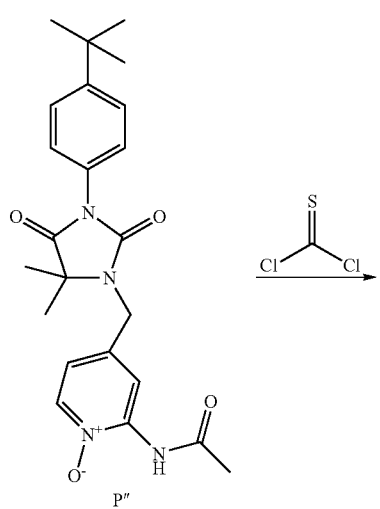

Product M may be obtained by treating product P'''' with an amine NHR4R5 in a solvent such as dioxane or dimethyl sulphoxide, for instance under the conditions described by Ohsawa, A. et al. (Chem. Pharm. Bull. 1980, 28, 3570-3575).

General Scheme 3:
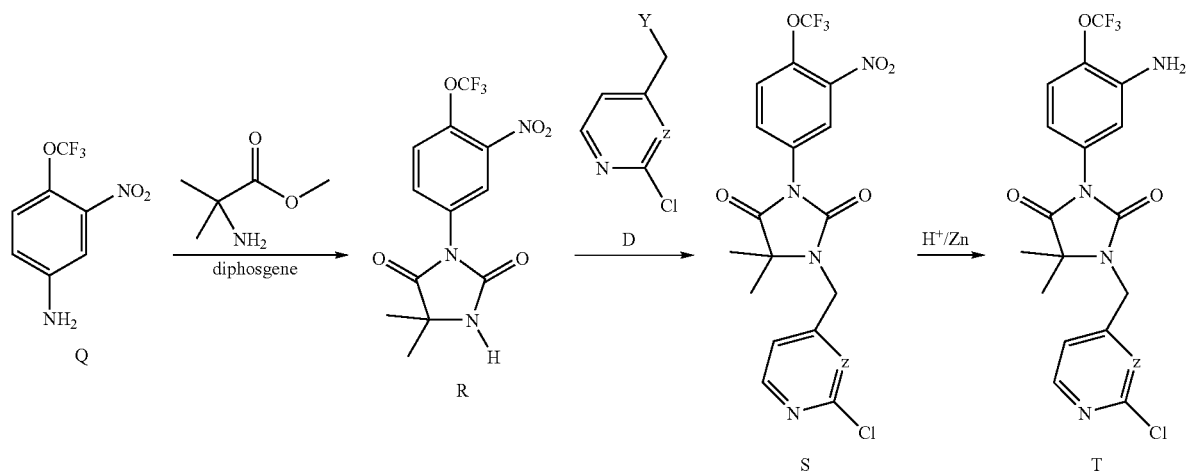
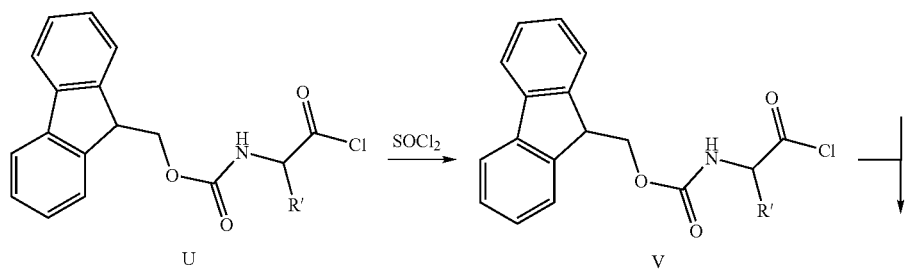
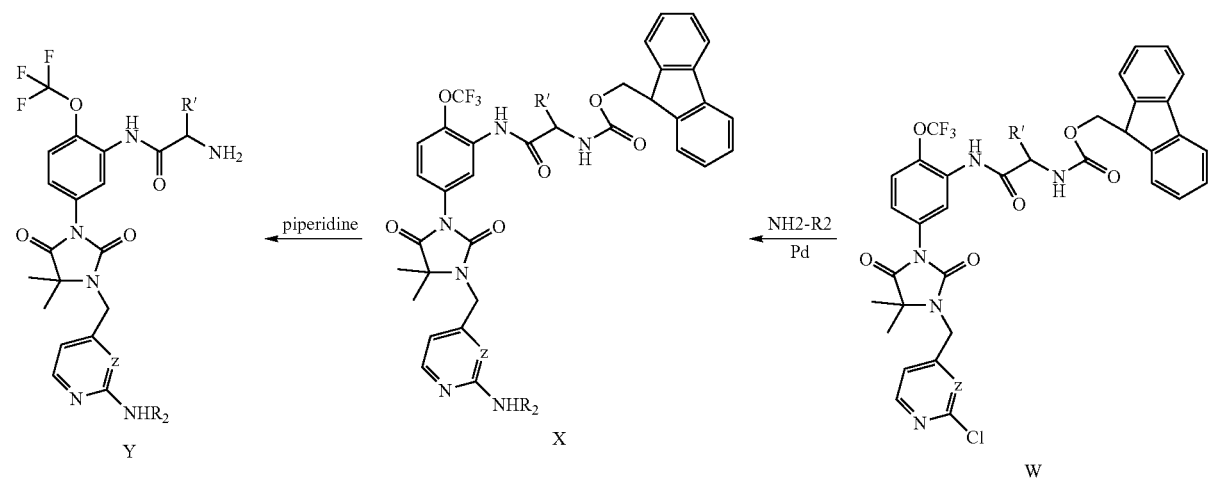

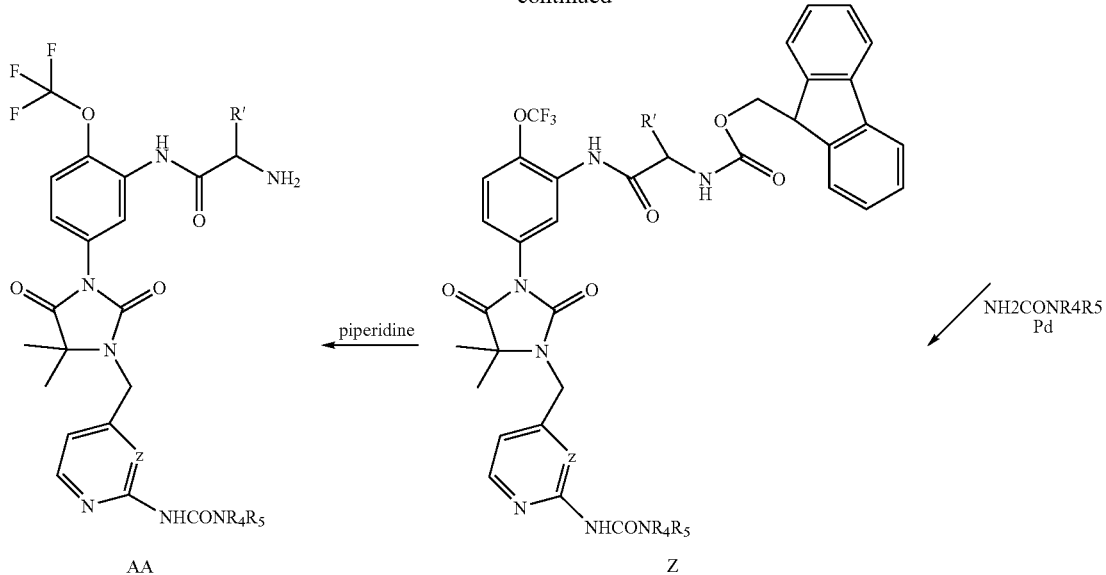

In General Scheme 3:

Hydantoin R may be obtained from the aniline Q by treatment with diphosgene in a solvent such as dioxane or toluene, for instance under the conditions described by Francis, J. E. et al. (J. Med. Chem. (1991), 34(1), 281-90), the isocyanate are obtained being used in its native form and then reacted with methyl 2,2-dimethyl glycinate in a solvent such as toluene or N,N-dimethylformamide at a temperature of between 20° C. and the reflux temperature of the solvent, as described, for example, by Brana M. F. (J. Het. Chem. (2002), 39(2), 417-420.

The product S may be prepared by reacting the products R and D with sodium hydride in tetrahydrofuran or N,N-dimethylformamide at a temperature of between 0° C. and 60° C. as described in the preparation of product J.

The product T may be prepared by reducing the nitro S in an acid such as hydrochloric acid in the presence of a metal such as zinc at a temperature of between 20° C. and 100° C., as described by Bryce M. R. et al. (Tet. Lett. (1987), 28, 577-580).

The acid chloride V may be prepared from the acid U by treatment with thionyl chloride in a solvent such as dichloromethane, as described by Sener, A. et al (J. Heterocycl. Chem. (2002), 39 (5), 869-875.

The amide W may be prepared by reacting the acid chloride V with the amine T, as described by Feldman, P. L. et al. (Bioorg. Med. Chem. Lett. (2002), 12 (21), 3215-3218).

The product of formula X may be prepared from W by reaction with an amine (R2-NH2) in the presence of a palladium-based catalyst such as palladium acetate and a ligand such as xantphos in a solvent such as toluene, dioxane or tert-butanol, for instance under the conditions described by Buchwald, S. L. et al. (J. Org. Chem. (2001), 66 (8), 2560-2565).

The product Y may be obtained by treating compound X with piperidine in N,N-dimethylformamide, as described by Greene T. W. et al. (Protective Groups in Organic Chemistry, John Wiley & Sons 1991, second edition).

The product Z may be obtained from W by reaction with a urea (NH2CONR4R5) for instance under the conditions described for product X.

The product AA may be obtained by treating product Z for instance under the conditions described for product Y General Scheme 4:

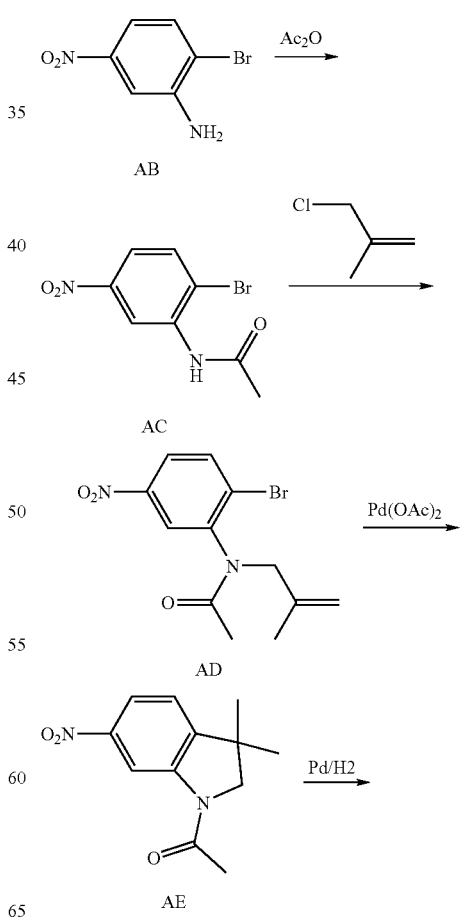

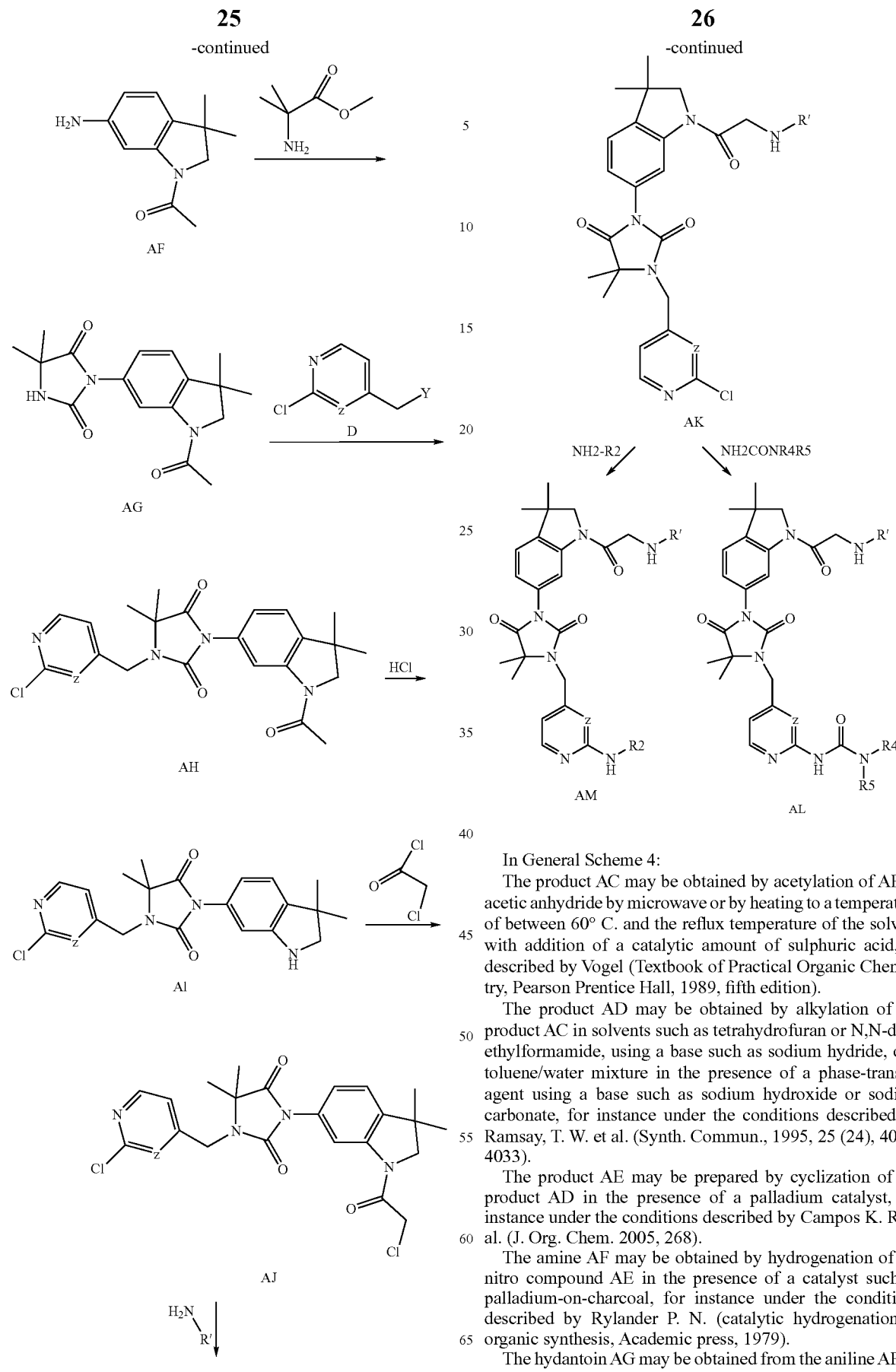

In General Scheme 4:

The product AC may be obtained by acetylation of AB in acetic anhydride by microwave or by heating to a temperature of between 60° C. and the reflux temperature of the solvent with addition of a catalytic amount of sulphuric acid, as described by Vogel (Textbook of Practical Organic Chemistry, Pearson Prentice Hall, 1989, fifth edition).

The product AD may be obtained by alkylation of the product AC in solvents such as tetrahydrofuran or N,N-dimethylformamide, using a base such as sodium hydride, or a toluene/water mixture in the presence of a phase-transfer agent using a base such as sodium hydroxide or sodium carbonate, for instance under the conditions described by Ramsay, T. W. et al. (Synth. Commun., 1995, 25 (24), 4029-4033).

The product AE may be prepared by cyclization of the product AD in the presence of a palladium catalyst, for instance under the conditions described by Campos K. R. et al. (J. Org. Chem. 2005, 268).

The amine AF may be obtained by hydrogenation of the nitro compound AE in the presence of a catalyst such as palladium-on-charcoal, for instance under the conditions described by Rylander P. N. (catalytic hydrogenation in organic synthesis, Academic press, 1979).

The hydantoin AG may be obtained from the aniline AF by treatment with carbonyldiimidazole in a solvent such as tetrahydrofuran, for instance under the conditions described by Nefzi A. et al. (J. Comb. Chem. (2002), 4(2), 175-178).

The product AH may be prepared from the product AG and the product D, for instance under the conditions described for the product J.

the product AI may be deacetylated using the product AH in a solvent such as dioxane, as described by Greene T. W. et al. (Protective Groups in Organic Chemistry, John Wiley & Sons 1991, second edition).

The product AJ may be obtained by acetylation of the product AI in the presence of a base such as triethylamine and in a solvent such as 1,2-dichloromethane, as described by Zhao, H. et al. (Bioorg. Med. Chem. Lett. (2002), 12 (21), 3111-3115).

The product AK may be prepared by reacting AJ with various amines, which may be used as solvent or as a solution in a solvent such as acetonitrile in the presence of a base such as potassium carbonate, as described by Zhao, H.; et al. (Bioorg. Med. Chem. Lett. (2002), 12 (21), 3111-3115).

The product AL may be prepared from AK by reaction with a urea (NH2CONR4R5) in the presence of a palladium-based catalyst, as described in the preparation of Z.

the product AM may be prepared from AK by reaction with an amine (R2-NH2) in the presence of a palladium-based catalyst, as described in the preparation of X.

In such preparations of the products of formula (I) according to the present invention, the starting materials, the intermediates and the products of formula (I), which may be in protected form, may be subjected, if necessary or if desired, to one or more of the following transformations, in any order:
a) a reaction for esterification of an acid function,
b) a reaction for saponification of an ester function to an acid function,
c) a reaction for oxidation of an alkylthio group to the corresponding sulphoxide or sulphone group,
d) a reaction for conversion of a ketone function to an oxime function,
e) a reaction for reducing a free or esterified carboxyl function to an alcohol function,
f) a reaction for conversion of an alkoxy function to a hydroxyl function, or alternatively of a hydroxyl function to an alkoxy function,
g) a reaction for oxidation of an alcohol function to an aldehyde, acid or ketone function,
h) a reaction for conversion of a nitrile radical to a tetrazolyl,
i) a reaction for reduction of nitro compounds to amino compounds,
j) a reaction for removal of the protecting groups that may be borne by the protected reactive functions,
k) a reaction for salification with a mineral or organic acid or with a base to obtain the corresponding salt,
l) a reaction for resolution of the racemic forms to resolved products,
said products of formula (I) thus obtained being in any possible racemic, enantiomeric or diastereoisomeric isomer form.

It may be noted that such reactions for converting substituents into other substituents may also be performed on the starting materials, and also on the intermediates as defined above before continuing the synthesis according to the reactions indicated in the process described above.

In the reactions described below, it may be necessary to protect reactive functional groups, for instance hydroxyl, acyl, free carboxyl or amino and monoalkylamino radicals, imino, thio, etc., which may thus be protected with appropriate protecting groups.

Conventional protecting groups may be used in accordance with the usual standard practice, for instance those described, for example, by T. W. Greene and P. G. M. Wuts in "Protective Groups in Organic Chemistry", John Wiley and Sons, 1991.

The following non-exhaustive list of examples of protection of reaction functions may be mentioned:
the hydroxyl groups may be protected, for example, with alkyl radicals such as tert-butyl, trimethylsilyl, tert-butyldimethylsilyl, methoxymethyl, tetrahydropyranyl, benzyl or acetyl,
the amino groups may be protected, for example, with acetyl, trityl, benzyl, tert-butoxycarbonyl, benzyloxycarbonyl, phthalimido radicals or other radicals known in peptide chemistry,
the acyl groups such as the formyl group may be protected, for example, in the form of cyclic or noncyclic ketals or thioketals such as dimethyl or diethylketal or ethylene dioxyketal, or diethylthioketal or ethylenedithioketal,
the acid functions of the products described above may be, if desired, amidated with a primary or secondary amine, for example in methylene chloride in the presence, for example, of 1-ethyl-3-(dimethylaminopropyl)carbodiimide hydrochloride at room temperature:
the acid functions may be protected, for example, in the form of esters formed with readily cleavable esters such as benzyl esters or tert-butyl esters, or esters known in peptide chemistry.

These reactions a) to k) indicated above may be performed, for example, as indicated below.
a) The products described above may, if desired, undergo, on the possible carboxyl functions, esterification reactions that may be performed according to the usual methods known to those skilled in the art.
b) The possible conversions of ester functions into an acid function of the products described above may be, if desired, performed under the usual conditions known to those skilled in the art, especially by acid or alkaline hydrolysis, for example with sodium hydroxide or potassium hydroxide in alcoholic medium such as, for example, in methanol, or alternatively with hydrochloric acid or sulphuric acid.
c) the possible alkylthio groups in the products described above, in which the alkyl radical is optionally substituted with one or more halogen atoms, especially fluorine, may, if desired, be converted into the corresponding sulphoxide or sulphone functions under the usual conditions known to those skilled in the art such as, for example, with peracids such as, for example, peracetic acid or meta-chloroperbenzoic acid, or alternatively with ozone, oxone or sodium periodate in a solvent such as, for example, methylene chloride or dioxane at room temperature.

The production of the sulphoxide function may be promoted with an equimolar mixture of the product containing an alkylthio group and the reagent such as, especially, a peracid.

The production of the sulphone function may be promoted with a mixture of the product containing an alkylthio group with an excess of the reagent such as, especially, a peracid.
d) The reaction for conversion of a ketone function into an oxime may be performed under the usual conditions known to those skilled in the art, such as, especially, a reaction in the presence of an optionally O-substituted hydroxylamine in an alcohol such as, for example, ethanol, at room temperature or with heating.
e) The possible free or esterified carboxyl functions of the products described above may be, if desired, reduced to an alcohol function by the methods known to those skilled in the art: the possible esterified carboxyl functions may be, if desired, reduced to an alcohol function by the methods known to those skilled in the art and especially with lithium aluminium hydride in a solvent such as, for example, tetrahydrofuran or dioxane or ethyl ether.

The possible free carboxyl functions of the products described above may be, if desired, reduced to an alcohol function especially with boron hydride.

f) The possible alkoxy functions such as, especially, methoxy, in the products described above, may be, if desired, converted into a hydroxyl function under the usual conditions known to those skilled in the art, for example with boron tribromide in a solvent such as, for example, methylene chloride, with pyridine hydrobromide or hydrochloride or with hydrobromic acid or hydrochloric acid in water or trifluoroacetic acid at reflux.

g) The possible alcohol functions of the products described above may be, if desired, converted into an aldehyde or acid function by oxidation under the usual conditions known to those skilled in the art, such as, for example, by the action of manganese oxide to obtain the aldehydes, or of Jones's reagent to access the acids.

h) The possible nitrile functions of the products described above may be, if desired, converted into tetrazolyl under the usual conditions known to those skilled in the art, such as, for example, by cycloaddition of a metal azide such as, for example, sodium azide or a trialkyltin azide on the nitrile function, as indicated in the method described in the article referenced as follows:

J. Organometallic Chemistry., 33, 337 (1971) KOZIMA S. et al.

It may be noted that the reaction for conversion of a carbamate into urea and especially of a sulphonylcarbamate into sulphonylurea may be performed, for example, at the reflux point of a solvent such as, for example, toluene, in the presence of the appropriate amine.

It is understood that the reactions described above may be performed as indicated or alternatively, where appropriate, according to other common methods known to those skilled in the art.

i) The removal of protecting groups such as, for example, those indicated above may be performed under the usual conditions known to those skilled in the art, especially via an acid hydrolysis performed with an acid such as hydrochloric acid, benzenesulphonic acid or para-toluenesulphonic acid, formic acid or trifluoroacetic acid, or alternatively via a catalytic hydrogenation.

The phthalimido group may be removed with hydrazine.

A list of various protecting groups that may be used will be found, for example, in patent BF 2 499 995.

j) The products described above may, if desired, be subjected to salification reactions, for example with a mineral or organic acid or with a mineral or organic base according to the usual methods known to those skilled in the art.

k) The possible optically active forms of the products described above may be prepared by resolving the racemic mixtures according to the usual methods known to those skilled in the art.

The possible reactive functions that are optionally protected are especially the hydroxyl or amino functions. Usual protecting groups are used to protect these functions. Examples that may be mentioned include the following protecting groups for the amino radical: tert-butyl, tert-amyl, trichloroacetyl, chloroacetyl, benzhydryl, trityl, formyl, benzyloxycarbonyl.

Protecting groups for the hydroxyl radical that may be mentioned include radicals such as formyl, chloroacetyl, tetrahydropyranyl, trimethylsilyl and tert-butyldimethylsilyl.

It is clearly understood that the above list is not limiting and that other protecting groups, which are known, for example, in peptide chemistry, may be used. A list of such protecting groups is found, for example, in French patent BF 2 499 995, the content of which is incorporated herein by reference.

The possible reactions for removal of the protecting groups are performed as indicated in said patent BF 2 499 995. The preferred method of removal is acid hydrolysis with acids chosen from hydrochloric acid, benzenesulphonic acid or para-toluenesulphonic acid, formic acid or trifluoroacetic acid. Hydrochloric acid is preferred.

The possible reaction for hydrolysis of the >C=NH group to a ketone group is also preferably performed using an acid such as aqueous hydrochloric acid, for example at reflux.

An example of removal of the tert-butyldimethylsilyl group using hydrochloric acid is given below in the examples.

The possible esterification of a free OH radical is performed under standard conditions. An acid or a functional derivative, for example an anhydride such as acetic anhydride in the presence of a base such as pyridine may be used, for example.

The possible esterification or salification of a COOH group is performed under the standard conditions known to those skilled in the art.

The possible amidation of a COOH radical is performed under standard conditions. A primary or secondary amine may be used on a functional derivative of the acid, for example a symmetrical or mixed anhydride.

The starting materials used for the preparation of the products of formula (I) according to the present invention may be known and commercially available or may be prepared according to methods known to those skilled in the art.

The products that are the subject of the present invention have advantageous pharmacological properties: it has been found that they especially have inhibitory properties on protein kinases.

Among these protein kinases, mention may be made especially of IGF1R.

FAK may also be mentioned. AKT may also be mentioned.

Tests given in the experimental section below illustrate the inhibitory activity of products of the present invention with respect to such protein kinases.

These properties thus make the products of general formula (I) of the present invention usable as medicaments for treating malignant tumours.

The products of formula (I) may also be used in the veterinary field.

A subject of the invention is thus the use, as medicaments, of the products of general formula (I) as defined above, the said products of formula (I) being in any possible racemic, enantiomeric or diastereoisomeric isomer form, and also the pharmaceutically acceptable addition salts with mineral and organic acids or with mineral and organic bases of the said products of formula (I).

A subject of the invention is particularly the use, as medicaments, of the products of formula (I), whose names are as follows:

3-(4-tert-butylphenyl)-5,5-dimethyl-1-[2-(pyridin-3-ylamino)pyrimidin-4-ylmethyl]imidazolidine-2,4-dione-
3-(4-{[3-(4-tert-butylphenyl)-5,5-dimethyl-2,4-dioxoimidazolidin-1-yl]methyl}pyrimidin-2-yl)-1,1-dimethylurea
3-[4-({3-[1-(N-cyclopentylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea
3-[1-(N-cyclopentylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione
(2R)-2-amino-N-[5-(4,4-dimethyl-2,5-dioxo-3-{[2-(pyridin-3-ylamino)pyridin-4-yl]methyl}imidazolidin-1-yl)-2-(trifluoromethoxy)phenyl]-2-phenylacetamide
(2R)-2-amino-N-{5-(4,4-dimethyl-2,5-dioxo-3-{[2-(pyridin-3-ylamino)pyridin-4-yl]methyl}imidazolidin-1-yl)-2-[(trifluoromethyl)thio]phenyl}-2-phenylacetamide
(2R)-2-amino-N-{5-[3-({2-[(dimethylcarbamoyl)amino]pyridin-4-yl}methyl)-4,4-dimethyl-2,5-dioxoimidazolidin-1-yl]-2-(trifluoromethoxy)phenyl}-2-phenylacetamide (2R)-2-amino-N-{5-[3-({2-[(dimethylcarbamoyl)amino]pyridin-4-yl}methyl)-4,4-dimethyl-2,5-dioxoimidazolidin-1-yl]-2-[(trifluoromethyl)thio]phenyl}-2-phenylacetamide 3-(4-tert-butylphenyl)-5,5-dimethyl-1-{[2-(pyrimidin-5-ylamino)pyridin-4-yl]methyl}imidazolidine-2,4-dione 3-(4-tert-butylphenyl)-5,5-dimethyl-1-{[2-(pyrimidin-5-ylamino)pyrimidin-4-yl]methyl}imidazolidine-2,4-dione the said products of formula (I) being in any possible racemic, enantiomeric or diastereoisomeric isomer form, and also the pharmaceutically acceptable addition salts with mineral and organic acids or with mineral and organic bases of the said products of formula (I).

The products may be administered parenterally, orally, perlingually, rectally or topically.

A subject of the invention is also pharmaceutical compositions, characterized in that they contain as active principle at least one of the medicaments of general formula (I).

These compositions may be in the form of injectable solutions or suspensions, tablets, coated tablets, capsules, syrups, suppositories, creams, ointments and lotions. These pharmaceutical forms are prepared according to the usual methods. The active principle may be incorporated into excipients usually used in these compositions, such as aqueous or nonaqueous vehicles, talc, gum arabic, lactose, starch, magnesium stearate, cocoa butter, fatty substances of animal or plant origin, paraffin derivatives, glycols, various wetting, dispersing or emulsifying agents, and preserving agents.

The usual dose, which varies according to the individual treated and the complaint under consideration, may be, for example, from 10 mg to 500 mg per day orally in man.

The present invention thus relates to the use of products of formula (I) as defined above or of pharmaceutically acceptable salts of said products of formula (I) for the preparation of medicaments for inhibiting the activity of protein kinases and especially of a protein kinase.

The present invention thus relates to the use of products of formula (I) as defined above or of pharmaceutically acceptable salts of said products of formula (I) in which the protein kinase is a protein tyrosine kinase.

The present invention thus relates to the use of products of formula (I) as defined above or of pharmaceutically acceptable salts of said products of formula (I) in which the protein kinase is chosen from the following group: EGFR, Fak, FLK-1, FGFR1, FGFR2, FGFR3, FGFR4, FGFR5, flt-1, IGF-1R, KDR, PDGFR, tie2, VEGFR, AKT, Raf.

The present invention thus relates particularly to the use of products of formula (I) as defined above or of pharmaceutically acceptable salts of said products of formula (I) in which the protein kinase is IGF1R.

The present invention also relates to the use of products of formula (I) as defined above or of pharmaceutically acceptable salts of said products of formula (I) in which the protein kinase is in a cell culture, and also to this use in a mammal.

The present invention thus relates to the use of products of formula (I) as defined above or of pharmaceutically acceptable salts of said products of formula (I) for the preparation of a medicament for preventing or treating a disease characterized by deregulation of the activity of a protein kinase and especially such a disease in a mammal.

The present invention relates to the use of products of formula (I) as defined above or of pharmaceutically acceptable salts of said products of formula (I) for the preparation of a medicament for preventing or treating a disease belonging to the following group: disorders of blood vessel proliferation, fibrotic disorders, disorders of mesangial cell proliferation, metabolic disorders, allergies, asthma, thrombosis, diseases of the nervous system, retinopathy, psoriasis, rheumatoid arthritis, diabetes, muscle degeneration, oncology diseases and cancer.

The present invention thus relates to the use of products of formula (I) as defined above or of pharmaceutically acceptable salts of said products of formula (I) for the preparation of a medicament for treating oncology diseases.

The present invention relates particularly to the use of products of formula (I) as defined above or of pharmaceutically acceptable salts of said products of formula (I) for the preparation of a medicament for treating cancers.

Among these cancers, the present invention is most particularly of interest in the treatment of solid tumours and the treatment of cancers that are resistant to cytotoxic agents.

Among these cancers, the present invention relates most particularly to the treatment of breast cancer, stomach cancer, cancer of the colon, lung cancer, cancer of the ovaries, cancer of the uterus, brain cancer, cancer of the kidney, cancer of the larynx, cancer of the lymphatic system, cancer of the thyroid, cancer of the urogenital tract, cancer of the tract including the seminal vesicle and prostate, bone cancer, cancer of the pancreas and melanomas.

The present invention is even more particularly of interest in treating breast cancer, cancer of the colon and lung cancer.

The present invention also relates to the use of products of formula (I) as defined above or of pharmaceutically acceptable salts of said products of formula (I) for the preparation of a medicament for cancer chemotherapy.

As medicaments according to the present invention for cancer chemotherapy, the products of formula (I) according to the present invention may be used alone or in combination with chemotherapy or radiotherapy or alternatively in combination with other therapeutic agents.

The present invention thus relates especially to the pharmaceutical compositions as defined above, also containing active principles of other chemotherapy medicaments for combating cancer.

Such therapeutic agents may be commonly used antitumour agents.

As examples of known inhibitors of protein kinases, mention may be made especially of butyrolactone, flavopiridol, 2-(2-hydroxyethylamino)-6-benzylamino-9-methylpurine, olomucine, Glivec and Iressa.

The products of formula (I) according to the present invention may thus also be advantageously used in combination with antiproliferative agents: as examples of such antiproliferative agents, but without, however, being limited to this list, mention may be made of aromatase inhibitors, antioestrogens, the topoisomerase I inhibitors, the topoisomerase II inhibitors, microtubule-active agents, alkylating agents, histone deacetylase inhibitors, farnesyl transferase inhibitors, COX-2 inhibitors, MMP inhibitors, mTOR inhibitors, antineoplastic antimetabolites, platinum compounds, compounds that reduce the activity of protein kinases and also anti-angiogenic compounds, gonadorelin agonists, antiandrogens, bengamides, biphosphonates and trastuzumab.

Examples that may thus be mentioned include anti-microtubule agents, for instance taxoids, vinca alkaloids, alkylating agents such as cyclophosphamide, DNA-intercalating agents, for instance cis-platinum, agents that are interactive on topoisomerase, for instance camptothecin and derivatives, anthracyclines, for instance adriamycin, antimetabolites, for instance 5-fluorouracil and derivatives, and the like.

The present invention thus relates to products of formula (I) as protein kinase inhibitors, said products of formula (I) being in any possible racemic, enantiomeric or diastereoisomeric isomer form, and also the addition salts with pharmaceutically acceptable mineral and organic acids or with pharmaceutically acceptable mineral and organic bases of said products of formula (I), and also the prodrugs thereof.

The present invention relates particularly to products of formula (I) as defined above, as IGF1R inhibitors.

The present invention relates more particularly to the products of formula (I) as defined above as IGF1R inhibitors.

The 1H NMR spectra are recorded on Brüker spectrometers at 400 MHz (AVANCE DRX-400) or at 300 MHz (BRUKER AVANCE DPX-300). The chemical shifts are given in ppm (δ in ppm)—in the solvent dimethyl sulphoxide-d6 (DMSO-d6) reference to 2.50 ppm at a temperature of 303K.

The mass spectra were acquired either by electrospray (ES) on a Q-Tof-2 (Micromass), ZQ (Micromass) or Quattro Premier (Micromass) machine, or by electron impact (EI); 70 eV; Micromass GCT of Premier machine, or by chemical ionization (CI); reactor and gas: ammonia; Micromass GCT of machine.

The LCMS is performed on a Hypersil Gold C18 column 3×50 mm in diameter; particles: 3 μm
initial conditions:

| Solvent A: water containing 0.05% TFA | 95% |
| Solvent B: acetonitrile containing 0.05% TFA | 5% |

Flow rate 0.9 mL; pressure at $t_0$: 145b; volume injected: 5 μl
GRADIENT over 7 minutes

| Time | % A | % B |
|------|-----|-----|
| 0    | 95  | 5   |
| 5    | 5   | 95  |
| 5.5  | 5   | 95  |
| 6.5  | 95  | 5   |
| 7    | 95  | 5   |

DAD UV detector: 200≦λ≦400 nm, the mass is measured by electrospray (ES+) on a Q-Tof-2 machine (Micromass).

The examples whose preparation follows illustrate the present invention without, however, limiting it.

EXAMPLE 1

3-(4-tert-butylphenyl)-5,5-dimethyl-1-[2-(pyridin-3-ylamino)pyrimidin-4-ylmethyl]imidazolidine-2,4-dione Stage g: 3-(4-tert-butylphenyl)-5,5-dimethyl-1-[2-(pyridin-3-ylamino)pyrimidin-4-ylmethyl]imidazolidine-2,4-dione

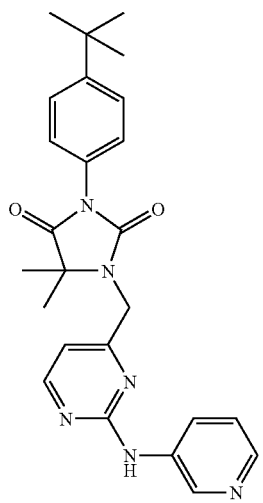

To a solution of 0.45 g of 1-[(2-aminopyrimidin-4-yl)methyl]-3-(4-tert-butylphenyl)-5,5-dimethylimidazolidine-2,4-dione obtained in stage f) in 15 mL of dioxane are successively added under argon 0.29 g of 3-bromopyridine, 1.51 g of caesium carbonate, 0.085 g of 9,9-dimethyl-4,5-bis(diphenylphosphino)xanthene and 0.027 g of palladium acetate. The reaction medium is heated at 120° C. for 5 hours. After cooling, the reaction mixture is filtered, and the filtrate is concentrated under reduced pressure. The residue obtained is purified by chromatography on a column of silica, eluting with dichloromethane, to give 76 mg of 3-(4-tert-butylphenyl)-5,5-dimethyl-1-[2-(pyridin-3-ylamino)pyrimidin-4-ylmethyl]imidazolidine-2,4-dione, the characteristics of which are as follows:

1H NMR spectrum at 300 MHz: 1.32 (s, 9H); 1.45 (s, 6H); 2.54 (s, 6H); 4.64 (s, 2H); 7.11 (d, J=5.0 Hz, 1H); 7.35 (d, J=8.5 Hz, 2H); 7.51 (d, J=8.5 Hz, 2H); 7.72 (dd, J=7.5 and 9.0 Hz, 1H); 8.40 (broad d, J=5.5 Hz, 1H); 8.57 (m, 2H); 9.06 (broad s, 1H); 10.35 (s, 1H).

Mass Spectrum (ES): m/z=445 [M+H]+ base peak

Stage f): 1-[(2-aminopyrimidin-4-yl)methyl]-3-(4-tert-butylphenyl)-5,5-dimethylimidazolidine-2,4-dione

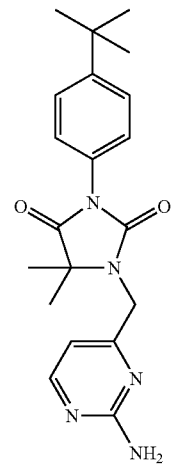

A solution of 0.45 g of 3-(4-tert-butylphenyl)-5,5-dimethyl-1-{[2-(methylsulphonyl)pyrimidin-4-yl]methyl}imidazolidine-2,4-dione obtained in stage e) in 2.1 mL of dioxane and 2.1 mL of 30% aqueous ammonia is heated in a sealed microwave tube at 120° C. for 1 hour. After evaporating off the solvents, 0.38 g of 1-[(2-aminopyrimidin-4-yl)methyl]-3-(4-tert-butylphenyl)-5,5-dimethylimidazolidine-2,4-dione is obtained, the characteristics of which are as follows:

1H NMR spectrum at 400 MHz: 1.31 (s, 9H); 1.41 (s, 6H); 4.40 (s, 2H); 6.59 (s, 2H); 6.61 (d, J=5.0 Hz, 1H); 7.33 (d, J=8.5 Hz, 2H); 7.50 (d, J=8.5 Hz, 2H); 8.18 (d, J=5.0 Hz, 1H).

Mass Spectrum (ES): m/z=368 [M+H]+ base peak

Stage e): 3-(4-tert-butylphenyl)-5,5-dimethyl-1-{[2-(methylsulphonyl)pyrimidin-4-yl]methyl}imidazolidine-2,4-dione

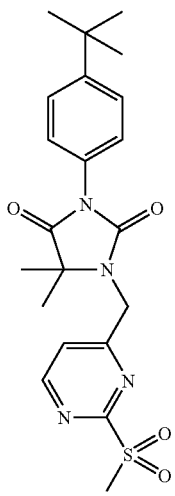

To a solution of 4.11 g of 3-(4-tert-butylphenyl)-5,5-dimethyl-1-{[2-(methylthio)pyrimidin-4-yl]methyl}imidazolidine-2,4-dione obtained in stage d) in 130 mL of 1,2-dichloroethane are added portionwise 9.8 g of 3-chloroperbenzoic acid (70-75%). The reaction mixture is stirred at room temperature for 15 hours and then washed successively with twice 100 mL of saturated sodium hydrogen carbonate solution, with water and then with saturated sodium chloride solution. The organic phase is dried over magnesium sulphate, filtered and evaporated under reduced pressure. The residue is purified by chromatography on a column of silica, eluting with dichloromethane, to give 0.8 g of 3-(4-tert-butylphenyl)-5,5-dimethyl-1-{[2-(methylsulphonyl)-pyrimidin-4-yl]methyl}imidazolidine-2,4-dione, the characteristics of which are as follows:

1H NMR spectrum at 400 MHz: 1.31 (s, 9H); 1.46 (s, 6H); 3.41 (s, 3H); 4.85 (s, 2H); 7.33 (d, J=8.5 Hz, 2H); 7.50 (d, J=8.5 Hz, 2H); 7.92 (d, J=5.5 Hz, 1H); 9.04 (d, J=5.5 Hz, 1H).

Mass Spectrum (ES): m/z=431 [M+H]$^+$ base peak

Stage d): 3-(4-tert-butylphenyl)-5,5-dimethyl-1-{[2-(methylthio)pyrimidin-4-yl]methyl}imidazolidine-2,4-dione

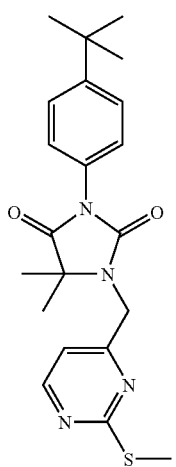

To a suspension of 1.74 g of sodium hydride (60%) in 70 mL of tetrahydrofuran are successively added, dropwise under an inert atmosphere of argon, a solution of 4.52 g of 3-(4-tert-butylphenyl)-5,5-dimethyl-imidazolidine-2,4-dione obtained in stage c) in 25 mL of tetrahydrofuran, followed by a solution of 5.14 g of 4-(chloromethyl)-2-(methylthio)pyrimidine in 50 mL of tetrahydrofuran. After addition, the reaction mixture is refluxed for 48 hours, cooled to room temperature and poured into distilled water, and the aqueous phase is washed with ethyl acetate. The organic phase is then washed successively with water and saturated sodium chloride solution, dried over magnesium sulphate, filtered and concentrated under reduced pressure. The residue is purified by chromatography on a column of silica, eluting with dichloromethane, to give 5.92 g of 3-(4-tert-butylphenyl)-5,5-dimethyl-1-{[2-(methylthio)pyrimidin-4-yl]methyl}imidazolidine-2,4-dione, the characteristics of which are as follows:

1H NMR spectrum at 300 MHz: 1.31 (s, 9H); 1.43 (s, 6H); 2.50 (masked, 3H); 4.64 (s, 2H); 7.27 (d, J=5.0 Hz, 1H); 7.32 (d, J=8.5 Hz, 2H); 7.51 (d, J=8.5 Hz, 2H); 8.58 (d, J=5.0 Hz, 1H).

Mass Spectrum (ES): m/z=399; [M+H]$^+$ base peak

Stage c): 3-(4-tert-butylphenyl)-5,5-dimethyl-imidazolidine-2,4-dione

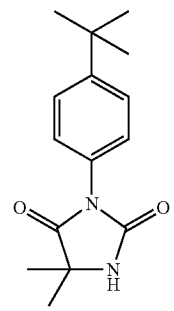

To a suspension of 15 g of 4-tert-butylphenyl-isocyanate in 200 mL of toluene are successively added 31.52 mL of triethylamine and 13.15 g of 2,2-dimethylglycine methyl ester hydrochloride. The reaction mixture is refluxed for 24 h, cooled to room temperature, poured into distilled water and extracted with ethyl acetate. The organic phase is washed successively with water and with saturated sodium chloride solution, dried over magnesium sulphate, filtered and concentrated under reduced pressure. The residue is taken up in diethyl ether and the solid formed is filtered off and dried to give 17.75 g of 3-(4-tert-butylphenyl)-5,5-dimethyl-imidazolidine-2,4-dione, the characteristics of which are as follows:

1H NMR spectrum at 300 MHz: 1.30 (s, 9H); 1.39 (s, 6H); 7.26 (d, J=8.5 Hz, 2H); 7.48 (d, J=8.5 Hz, 2H); 8.48 (broad s, 1H).

Mass Spectrum (EI): m/z=260 M$^+$

Stage b): 4-(chloromethyl)-2-(methylthio)pyrimidine

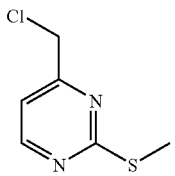

To a solution of 13.69 g of [2-(methylthio)pyrimidin-4-yl] methanol obtained in stage a) in 250 mL of dichloromethane are added dropwise 7.67 mL of thionyl chloride, followed by 3.91 mL of N,N-dimethylformamide. The reaction mixture is stirred at room temperature for 15 hours and concentrated under reduced pressure. The residue is taken up in diisopropyl ether and the solid formed is filtered off and dried to give 10.28 g of 4-(chloromethyl)-2-(methylthio)pyrimidine, the characteristics of which are as follows:

1H NMR spectrum at 400 MHz: 2.52 (s, 3H); 4.72 (s, 2H); 7.33 (d, J=5.5 Hz, 1H); 8.68 (d, J=5.5 Hz, 1H).

Mass Spectrum (IC): m/z=175 [M+H]$^+$ base peak

Stage a): [2-(methylthio)pyrimidin-4-yl]methanol

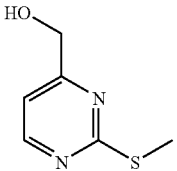

To a suspension of 20 g of 2-methylthiopyrimidine-4-carboxaldehyde in 400 mL of methanol at 0° C. are added portionwise 9.8 g of sodium borohydride. After addition, the reaction mixture is stirred at room temperature for 15 hours and concentrated under reduced pressure. The residue is taken up in dichloromethane and washed successively with water and saturated sodium chloride solution, dried over magnesium sulphate and filtered. The solvent is evaporated off under reduced pressure to give 16.69 g of [2-(methylthio) pyrimidin-4-yl]methanol, the characteristics of which are as follows:

1H NMR spectrum at 400 MHz: 2.49 (s, 3H); 4.48 (d, J=5.5 Hz, 2H); 5.61 (t, J=5.5 Hz, 1H); 7.24 (d, J=5.5 Hz, 1H); 8.60 (d, J=5.5 Hz, 1H).

Mass Spectrum (EI): m/z=156 M$^+$; m/z=138 [M−H2O]$^+$ base peak

EXAMPLE 2

3-(4-{[3-(4-tert-butylphenyl)-5,5-dimethyl-2,4-dioxoimidazolidin-1-yl]methyl}pyrimidin-2-yl)-1,1-dimethylurea

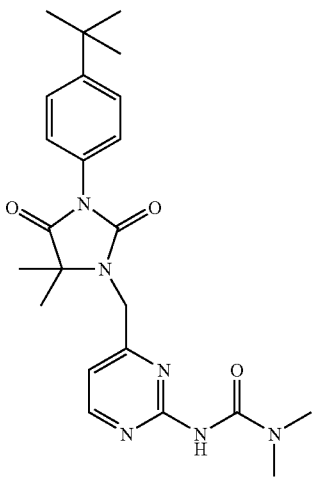

Stage b: 3-(4-{[3-(4-tert-butylphenyl)-5,5-dimethyl-2,4-dioxo-imidazolidin-1-yl]methyl}pyrimidin-2-yl)-1,1-dimethylurea To a solution of 70 mg of phenyl (4-{[3-(4-tert-butylphenyl)-5,5-dimethyl-2,4-dioxoimidazolidin-1-yl] methyl}pyrimidin-2-yl)carbamate obtained in stage a) below in 3 mL of tetrahydrofuran is introduced, under argon, 0.71 mL of a 2M solution of dimethylamine in tetrahydrofuran. After stirring for one hour at room temperature, the reaction medium is concentrated under reduced pressure and the residue is purified by chromatography on a column of silica, eluting with a dichloromethane/acetonitrile/methanol mixture (98/1/1 by volume) to give 20 mg of 3-(4-{[3-(4-tert-butylphenyl)-5,5-dimethyl-2,4-dioxoimidazolidin-1-yl]methyl}pyrimidin-2-yl)-1,1-dimethylurea in the form of a white powder, the characteristics of which are as follows:

1H NMR spectrum at 400 MHz: 1.31 (s, 9H); 1.43 (s, 6H); 2.90 (s, 6H); 4.54 (s, 2H); 7.03 (d, J=5.0 Hz, 1H); 7.33 (d, J=8.5 Hz, 2H); 7.50 (d, J=8.5 Hz, 2H); 8.46 (d, J=5.0 Hz, 1H); 9.25 (s, 1H)

Mass Spectrum (ES): m/z=439 [M+H]$^+$ (base peak)
m/z=437 [M−H]$^−$ (base peak)

Stage a: Phenyl (4-{[3-(4-tert-butylphenyl)-5,5-dimethyl-2,4-dioxoimidazolidin-1-yl]methyl}pyrimidin-2-yl)carbamate

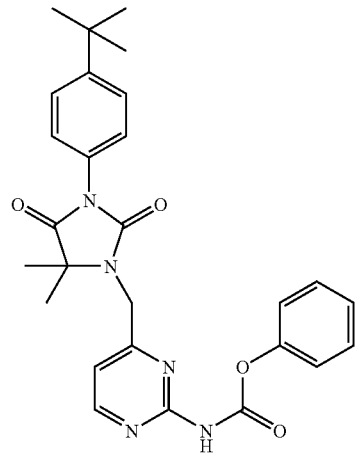

To a solution of 100 mg of 1-[(2-aminopyrimidin-4-yl) methyl]-3-(4-tert-butylphenyl)-5,5-dimethylimidazolidine-2,4-dione obtained in stage f) of Example 1, in 3 mL of tetrahydrofuran, are added, at 0° C., 0.034 mL of pyridine and 0.045 mL of phenyl chlorocarbonate. The reaction mixture is stirred for 4.5 hours at room temperature and then diluted with ethyl acetate and washed with twice 30 mL of aqueous 1N hydrochloric acid solution, then with twice 30 mL of water, with twice 30 mL of saturated aqueous sodium hydrogen carbonate solution and finally with saturated aqueous sodium chloride solution. The organic phase is dried over magnesium sulphate, filtered and concentrated under reduced pressure. The residue is purified by chromatography on a column of silica, eluting with an ethyl acetate/cyclohexane mixture (62/38 by volume) to give 70 mg of phenyl (4-{[3-(4-tert-butylphenyl)-5,5-dimethyl-2,4-dioxo-imidazolidin-1-yl]methyl}pyrimidin-2-yl)carbamate in the form of a white powder, the characteristics of which are as follows:

Mass Spectrum (ES): m/z=488 [M+H]$^+$ (base peak)

EXAMPLE 3

3-[4-({3-[1-(N-cyclopentylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea

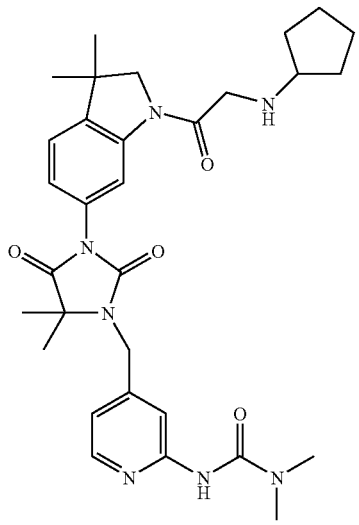

Stage m): 3-[4-({3-[1-(N-cyclopentylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea To a solution of 0.312 g of tert-butyl [2-(6-{3-[(2-chloropyridin-4-yl)methyl]-4,4-dimethyl-2,5-dioxoimidazolidin-1-yl}-3,3-dimethyl-2,3-dihydro-1H-indol-1-yl)-2-oxoethyl]cyclopentylcarbamate obtained in stage l) below in 12 mL of dioxane are successively added, under argon, 0.066 g of N,N-dimethylurea, 0.028 g of (9,9-dimethyl-9H-xanthene-3,6-diyl)bis(diphenylphosphine) (Xantphos), 0.022 g of palladium acetate and 0.65 g of caesium carbonate. The reaction mixture is refluxed for 4 hours and then filtered and concentrated under reduced pressure. The residue is taken up in 10 mL of dioxane and then 12 mL of a 4N solution of hydrogen chloride in dioxane are added and the reaction mixture is stirred at room temperature for 15 hours. After concentrating under reduced pressure, the residue is taken up in 40 mL of water, neutralized by addition of sodium hydrogen carbonate and extracted with three times 20 mL of dichloromethane. The combined organic phases are then washed with water, dried over magnesium sulphate, filtered and concentrated under reduced pressure. The residue is purified by chromatography on a column of silica, eluting with a mixture of dichloromethane and methanol (90/10 by volume) to give 0.08 g of 3-[4-({3-[1-(N-cyclopentylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea, the characteristics of which are as follows:

1H NMR spectrum at 400 MHz: from 1.28 to 1.78 (m, 8H); 1.32 (s, 6H); 1.40 (s, 6H); 2.94 (s, 6H); 3.09 (m, 1H); 3.50 (broad s, 2H); 3.91 (s, 2H); 4.58 (s, 2H); 6.99 (broad d, J=5.5 Hz, 1H); 7.08 (dd, J=2.0 and 8.0 Hz, 1H); 7.37 (d, J=8.0 Hz, 1H); 7.83 (broad s, 1H); 8.05 (broad s, 1H); 8.18 (d, J=5.5 Hz, 1H); 8.79 (s, 1H).

Mass Spectrum (ES): m/z=576 [M+H]$^+$ m/z=598 [M+Na]$^+$

Stage l): tert-butyl [2-(6-{3-[(2-chloropyridin-4-yl)methyl]-4,4-dimethyl-2,5-dioxoimidazolidin-1-yl}-3,3-dimethyl-2,3-dihydro-1H-indol-1-yl)-2-oxoethyl]cyclopentylcarbamate

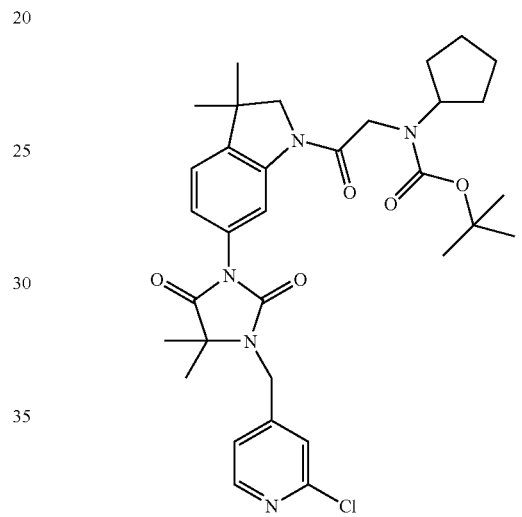

To a solution of 3.3 g of 1-[(2-chloropyridin-4-yl)methyl]-3-[1-(N-cyclopentylglycyl)-3,3-dimethyl-2,3-dihydro-1H-indol-6-yl]-5,5-dimethylimidazolidine-2,4-dione obtained in stage k) below in 60 mL of dichloromethane are added 1.79 mL of triethylamine followed by 1.5 g of di-tert-butyl dicarbonate. The reaction mixture is stirred at room temperature for 15 hours and then washed with three times 25 mL of water, dried over magnesium sulphate, filtered and concentrated under reduced pressure. The residue is purified by chromatography on a column of silica, eluting with a mixture of dichloromethane and methanol (95/5 by volume) to give 3.9 g of tert-butyl [2-(6-{3-[(2-chloropyridin-4-yl)methyl]-4,4-dimethyl-2,5-dioxo-imidazolidin-1-yl}-3,3-dimethyl-2,3-dihydro-1H-indol-1-yl)-2-oxoethyl]cyclopentylcarbamate, the characteristics of which are as follows:

1H NMR spectrum at 400 MHz: from 1.20 to 1.85 (m, 29H); 3.95 (broad s, 2H); from 3.98 to 4.45 (broad m, 3H); 4.63 (s, 2H); 7.10 (dd, J=2.0 and 8.5 Hz, 1H); 7.38 (d, J=8.5 Hz, 1H); 7.45 (broad d, J=5.5 Hz, 1H); 7.58 (broad s, 1H); 8.08 (broad s, 1H); 8.38 (d, J=5.5 Hz, 1H).

Mass Spectrum (ES): m/z=624 [M+H]$^+$ m/z=646 [M+Na]$^+$ m/z=668 [M–H]$^-$+HCOOH Stage k): 1-[(2-chloropyridin-4-yl)methyl]-3-[1-(N-cyclopentylglycyl)-3,3-dimethyl-2,3-dihydro-1H-indol-6-yl]-5,5-dimethylimidazolidine-2,4-dione

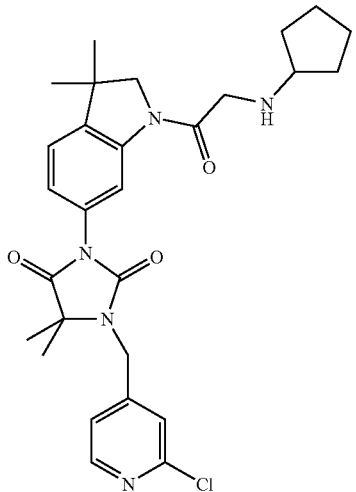

A solution of 3.423 g of 3-[1-(chloroacetyl)-3,3-dimethyl-2,3-dihydro-1H-indol-6-yl]-1-[(2-chloropyridin-4-yl)methyl]-5,5-dimethylimidazolidine-2,4-dione obtained in stage j) below in 42 mL of cyclopentylamine is heated at 70° C. for 4 hours. The reaction mixture is then concentrated under reduced pressure and the residue is taken up in 100 mL of water and extracted with three times 60 mL of ethyl acetate. The combined organic phases are then washed with water, dried over magnesium sulphate, filtered and concentrated under reduced pressure. The residue is purified by chromatography on a column of silica, eluting with a mixture of dichloromethane and methanol (95/5 by volume) to give 3.5 g of 1-[(2-chloropyridin-4-yl)methyl]-3-[1-(N-cyclopentylglycyl)-3,3-dimethyl-2,3-dihydro-1H-indol-6-yl]-5,5-dimethylimidazolidine-2,4-dione, the characteristics of which are as follows:

1H NMR spectrum at 400 MHz: from 1.25 to 1.78 (m, 8H); 1.32 (s, 6H); 1.40 (s, 6H); 2.00 (broad m, 1H); 3.05 (m, 1H); 3.48 (s, 2H); 3.91 (s, 2H); 4.63 (s, 2H); 7.09 (dd, J=1.5 and 8.5 Hz, 1H); 7.36 (d, J=8.5 Hz, 1H); 7.45 (broad d, J=5.5 Hz, 1H); 7.58 (broad s, 1H); 8.08 (broad s, 1H); 8.38 (d, J=5.5 Hz, 1H).

Mass Spectrum (ES): m/z=524 [M+H]+
m/z=568 [M−H]−+HCOOH

Stage j: 3-[1-(Chloroacetyl)-3,3-dimethyl-2,3-dihydro-1H-indol-6-yl]-1-[(2-chloropyridin-4-yl)methyl]-5,5-dimethylimidazolidine-2,4-dione

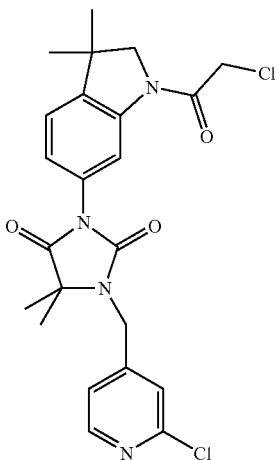

To a solution of 798 mg of 1-[(2-chloropyridin-4-yl)methyl]-3-(3,3-dimethyl-2,3-dihydro-1H-indol-6-yl)-5,5-dimethylimidazolidine-2,4-dione obtained in stage i) below in 40 mL of 1,2-dichloroethane are added 295 μl of diisopropylamine. The solution is cooled to −20° C. under argon and then 226 mg of chloroacetyl chloride are added dropwise. The reaction mixture is then stirred at 0° C. for 1.5 hours. After adding diethyl ether, the medium is concentrated under reduced pressure to give 1.2 g of a mixture mainly containing 3-[1-(chloroacetyl)-3,3-dimethyl-2,3-dihydro-1H-indol-6-yl]-1-[(2-chloropyridin-4-yl)methyl]-5,5-dimethylimidazolidine-2,4-dione in the form of a brown paste, the characteristics of which are as follows:

$R_f$: silica TLC=0.35 [dichloromethane/methanol 95/5 by volume]

Stage i: 1-[(2-chloropyridin-4-yl)methyl]-3-(3,3-dimethyl-2,3-dihydro-1H-indol-6-yl)-5,5-dimethylimidazolidine-2,4-dione

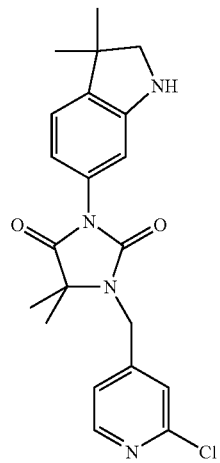

To a solution of 2.65 g of 3-(1-acetyl-3,3-dimethyl-2,3-dihydro-1H-indol-6-yl)-1-[(2-chloropyridin-4-yl)methyl]-5,5-dimethylimidazolidine-2,4-dione obtained in stage h) below in 30 mL of dioxane are added 33 mL of aqueous 1N hydrochloric acid solution. The reaction mixture is heated at 70° C. for 17 hours and concentrated under reduced pressure. The residue is diluted with 30 mL of water and poured into saturated aqueous sodium hydrogen carbonate solution, and the precipitate formed is filtered off, washed with four times 10 mL of water and dried to give 2.3 g of 1-[(2-chloropyridin-4-yl)methyl]-3-(3,3-dimethyl-2,3-dihydro-1H-indol-6-yl)-5,5-dimethylimidazolidine-2,4-dione in the form of a beige-coloured solid, the characteristics of which are as follows:

LCMS: RT=6.34 min; m/z=399 [M+H]+

Stage h: 3-(1-Acetyl-3,3-dimethyl-2,3-dihydro-1H-indol-6-yl)-1-[(2-chloropyridin-4-yl)methyl]-5,5-dimethylimidazolidine-2,4-dione

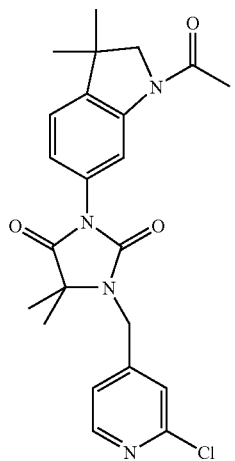

To 949 mg of sodium hydride are added dropwise, under argon, 5 mL of dimethylformamide, followed by addition of a solution of 6.8 g of 3-(1-acetyl-3,3-dimethyl-2,3-dihydro-1H-indol-6-yl)-5,5-dimethylimidazolidine-2,4-dione obtained in stage g) below in 40 mL of dimethylformamide. The solution obtained is stirred for 1.5 hours at 25° C., followed by addition of 5.24 g of 2-chloro-4-chloromethylpyridine obtained in stage b) below. The reaction mixture is stirred at room temperature for 15 hours and diluted with 300 mL of water, and the solid formed is filtered off, washed with three times 20 mL of water and with twice 20 mL of diethyl ether and dried to give 8.8 g of 3-(1-acetyl-3,3-dimethyl-2,3-dihydro-1H-indol-6-yl)-1-[(2-chloropyridin-4-yl)methyl]-5,5-dimethylimidazolidine-2,4-dione in the form of a beige-coloured solid, the characteristics of which are as follows:
Mass Spectrum (ES): m/z=441 [M+H]$^+$

Stage g: 3-(1-Acetyl-3,3-dimethyl-2,3-dihydro-1H-indol-6-yl)-5,5-dimethylimidazolidine-2,4-dione

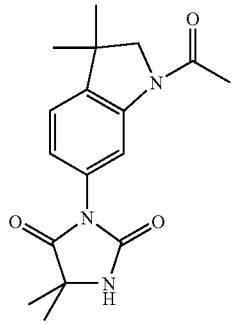

A solution of 6.6 g of 1,1'-carbonylbis(1H-imidazole) and 460 mg of 1H-imidazole in 50 mL of tetrahydrofuran is stirred under argon and cooled in an ice bath at 0° C. To this solution is added a suspension of 6.9 g of 1-acetyl-3,3-dimethylindolin-6-amine obtained in stage f) below in 50 mL of tetrahydrofuran. After stirring for one hour, 9.5 mL of triethylamine and 5.2 g of methyl 2-methylalaninate hydrochloride are added and the mixture is stirred for two hours at room temperature and then refluxed for 17 hours. After cooling to room temperature, the mixture is diluted with 800 mL of water and the precipitate formed is filtered off, washed with four times 25 mL of water and with three times 15 mL of diethyl ether and then dried to give 8 g of 3-(1-acetyl-3,3-dimethyl-2,3-dihydro-1H-indol-6-yl)-5,5-dimethylimidazolidine-2,4-dione in the form of a beige-coloured solid, the characteristics of which are as follows:
LCMS: RT=3.19 min; m/z=316 [M+H]$^+$; m/z=314 [M−H]$^-$

Stage f: 1-acetyl-3,3-dimethylindolin-6-amine

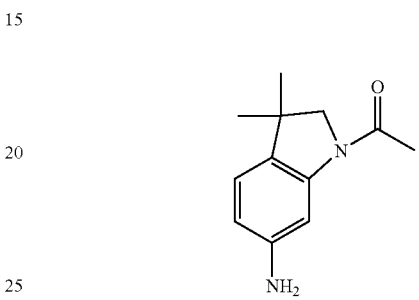

1.46 g of 10% palladium on charcoal, 8.8 g of 1-acetyl-3,3-dimethyl-6-nitroindoline obtained in stage e) below and 110 mL of ethanol are placed in a hydrogenation reactor. After reacting for one hour 10 minutes at 3 bar at a temperature of 25° C., the reaction medium is filtered through paper and concentrated under reduced pressure to give 6.9 g of 1-acetyl-3,3-dimethylindolin-6-amine in the form of a brown solid, the characteristics of which are as follows:
LCMS: RT=1.12 min; m/z=205 [M+H]$^+$

Stage e: 1-acetyl-3,3-dimethyl-6-nitroindoline

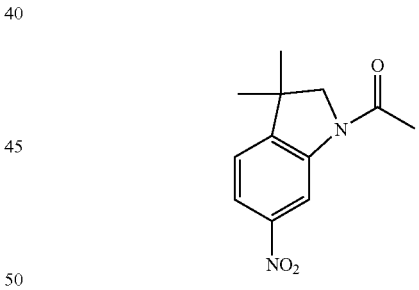

To a solution of 5.2 g of N-(2-bromo-5-nitrophenyl)-N-(2-methylprop-2-en-1-yl)acetamide obtained in stage d) below in 140 mL of dimethylformamide are added 2.12 g of N,N,N-triethylethanaminium chloride, 1.4 g of sodium formate and 3.4 g of sodium acetate. After stirring for 30 minutes under argon at room temperature, 410 mg of palladium diacetate are added and the mixture is heated at 80° C. for 5 hours. After cooling to room temperature, the reaction mixture is diluted with one litre of water, and the solid formed is filtered off and washed with four times 40 mL of water. The solid is then dissolved in 200 mL of ethyl acetate, dried over magnesium sulphate in the presence of 0.5 g of vegetable charcoal, filtered and concentrated under reduced pressure to give 3 g of 1-acetyl-3,3-dimethyl-6-nitroindoline in the form of a beige-yellow solid, the characteristics of which are as follows:
Mass Spectrum (EI): m/z=234 M$^+$ Stage d: N-(2-bromo-5-nitrophenyl)-N-(2-methyl-prop-2-en-1-yl)acetamide

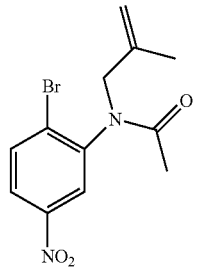

To a suspension of 1.34 g of sodium hydride in 10 mL of dimethylformamide under argon is added dropwise, at 0° C., a solution of 5.8 g of N-(2-bromo-5-nitrophenyl)acetamide obtained in stage c) below in 90 mL of dimethylformamide and the reaction medium is stirred at this temperature for 1 hour. 3.3 mL of 3-chloro-2-methylprop-1-ene are then added and the mixture is then heated at 60° C. for 2 hours. After cooling to room temperature, the mixture is diluted with one litre of water and extracted with four times 80 mL of ethyl acetate. The combined organic phases are washed with three times 50 mL of saturated aqueous sodium chloride solution, dried over magnesium sulphate, filtered and concentrated under reduced pressure. The residue is purified by chromatography on a column of silica, eluting with a mixture of heptane and ethyl acetate (80/20 by volume) to give 5.2 g of N-(2-bromo-5-nitrophenyl)-N-(2-methylprop-2-en-1-yl)acetamide in the form of a yellow solid, the characteristics of which are as follows:

Mass Spectrum (EI): m/z=312 M$^+$

Stage c: N-(2-bromo-5-nitrophenyl)acetamide

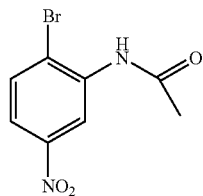

2.8 g of 2-bromo-5-nitroaniline are dissolved in 18 mL of acetic anhydride in a microwave oven reactor. After hermetically closing the reactor and reacting for one hour at 60° C. under microwave irradiation, the solid is filtered off and then washed with three times 10 mL of diethyl ether and dried to give 3 g of N-(2-bromo-5-nitrophenyl)acetamide in the form of a beige-coloured solid, the characteristics of which are as follows:

LCMS: RT=3.05 min; m/z=259; 261 [M+H]$^+$ (presence of a bromine

Stage b): 2-Chloro-4-chloromethylpyridine

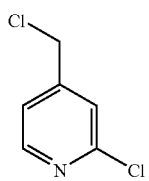

To a solution of 11.3 g of 2-chloro-4-hydroxymethylpyridine obtained in stage a) below in 200 mL of dichloromethane are added dropwise 6.896 mL of thionyl chloride, followed by 2.1 mL of dimethylformamide, the reaction mixture is stirred for 3 hours at room temperature and 50 mL of water are then added dropwise. The phases are separated and the organic phase is washed with water, dried over magnesium sulphate, filtered and concentrated under reduced pressure to give 12.8 g of 2-chloro-4-chloromethylpyridine in the form of an amber-coloured liquid, which is used without further purification.

R$_f$: silica TLC=0.44 (eluent: dichloromethane).

Stage a): 2-Chloro-4-hydroxymethylpyridine

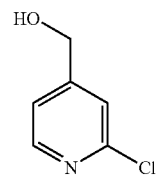

78.78 g of 2-chloroisonicotinic acid are added, under argon, portionwise, to 300 mL of a 2M solution of dimethyl sulphide-borane in tetrahydrofuran. The reaction mixture is stirred for 17 hours at room temperature and then treated successively with 20 mL of water dropwise and 20 mL of 5N hydrochloric acid. 300 mL of ethyl acetate are then added, the phases are separated and the organic phase is washed with three times 100 mL of saturated sodium chloride solution, dried over magnesium sulphate and filtered. The filtrate is then concentrated under reduced pressure to give 68.6 g of 2-chloro-4-hydroxymethylpyridine in the form of a pale yellow solid.

R$_f$: silica TLC=0.38 (eluent: dichloromethane/methanol 90/10 by volume).

EXAMPLE 4

3-[1-(N-cyclopentylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione

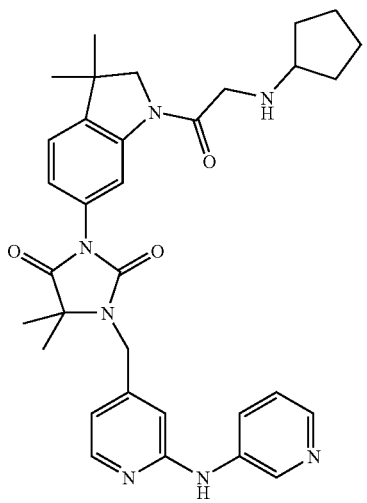

To a solution of 0.312 g of tert-butyl [2-(6-{3-[(2-chloropyridin-4-yl)methyl]-4,4-dimethyl-2,5-dioxoimidazolidin-1-yl}-3,3-dimethyl-2,3-dihydro-1H-indol-1-yl)-2-oxoethyl]cyclopentylcarbamate obtained in stage 1) of Example 3 in 12 mL of dioxane are successively added, under argon, 0.094 g of 3-aminopyridine, 0.028 g of (9,9-dimethyl-9H-xanthene-3,6-diyl)bis(diphenylphosphine) (Xantphos), 0.022 g of palladium acetate and 0.65 g of caesium carbonate. The reaction mixture is refluxed for 4 hours and then filtered, and the filtrate is concentrated under reduced pressure. The residue is taken up in 10 mL of dioxane, 12 mL of a 4N solution of hydrogen chloride in dioxane are then added and the reaction mixture is stirred at room temperature for 15 hours. After concentrating under reduced pressure, the residue is taken up in 40 mL of water, neutralized by addition of sodium hydrogen carbonate and extracted with three times 25 mL of dichloromethane. The combined organic phases are then washed with water, dried over magnesium sulphate filtered and concentrated under reduced pressure. The residue is triturated with diethyl ether and the solid obtained is filtered off and dried to give 0.12 g of 3-[1-(N-cyclopentylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione, the characteristics of which are as follows:

1H NMR spectrum at 400 MHz: from 1.28 to 1.78 (m, 8H); 1.32 (s, 6H); 1.42 (s, 6H); 2.10 (broad m, 1H); 3.06 (m, 1H); 3.48 (broad s, 2H); 3.91 (s, 2H); 4.55 (s, 2H); 6.82 (broad d, J=5.5 Hz, 1H); 6.84 (broad s, 1H); 7.08 (dd, J=2.0 and 8.0 Hz, 1H); 7.28 (dd, J=5.0 and 8.5 Hz, 1H); 7.39 (d, J=8.0 Hz, 1H); 8.08 (broad d, J=5.0 Hz, 1H); 8.13 (d, J=5.5 Hz, 1H); 8.21 (broad d, J=8.0 Hz, 1H); 8.79 (d, J=2.0 Hz, 1H); 9.21 (s, 1H).

Mass Spectrum (ES): m/z=582 [M+H]$^+$

EXAMPLE 5A (2R)-2-amino-N-[5-(4,4-dimethyl-2,5-dioxo-3-{[2-(pyridin-3-ylamino)pyridin-4-yl]methyl}imidazolidin-1-yl)-2-(trifluoromethoxy)phenyl]-2-phenylacetamide

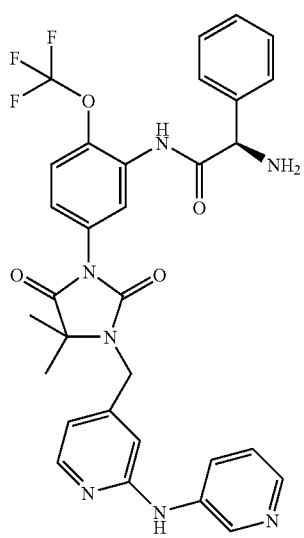

Stage e): (2R)-2-amino-N-[5-(4,4-dimethyl-2,5-dioxo-3-{[2-(pyridin-3-ylamino)pyridin-4-yl]methyl}imidazolidin-1-yl)-2-(trifluoromethoxy)phenyl]-2-phenylacetamide To a solution of 33 mg of (2R)-2-amino-N-[5-{3-[(2-chloropyridin-4-yl)methyl]-4,4-dimethyl-2,5-dioxoimidazolidin-1-yl}-2-(trifluoromethoxy)phenyl]-2-phenylacetamide obtained in stage d) below in 1 mL of dioxane are successively added, under argon, 7 mg of 3-aminopyridine, 3 mg of (9,9-dimethyl-9H-xanthene-3,6-diyl)bis(diphenylphosphine) (Xantphos), 1.1 mg of palladium acetate and 61 mg of caesium carbonate. The reaction mixture is heated at 110° C. for 1 hour, filtered and washed with twice 10 mL of dioxane, and the filtrate is then concentrated under reduced pressure. The residue is taken up in 1 mL of dioxane, 1 mL of a 4N solution of hydrogen chloride in dioxane is then added and the reaction mixture is stirred at 40° C. for 2 hours. The reaction mixture is then treated with 30 mL of saturated sodium hydrogen carbonate solution and extracted with three times 30 mL of ethyl acetate. The combined organic phases are then washed with water, dried over magnesium sulphate, filtered and concentrated under reduced pressure. The residue is purified by HPLC (gradient: water/acetonitrile containing 0.1% formic acid) to give 12 mg of (2R)-2-amino-N-[5-(4,4-dimethyl-2,5-dioxo-3-{[2-(pyridin-3-ylamino)pyridin-4-yl]methyl}imidazolidin-1-yl)-2-(trifluoromethoxy)phenyl]-2-phenylacetamide, the characteristics of which are as follows:

1H NMR spectrum at 400 MHz: 1.42 (s, 6H); 4.54 (s, 2H); 4.62 (s, 1H); 6.82 (m, 2H); from 7.22 to 7.38 (m, 5H); 7.42 (broad d, J=8.5 Hz, 2H); 7.60 (broad d, J=9.0 Hz, 1H); 8.07 (dd, J=1.5 and 5.5 Hz, 1H); 8.12 (d, J=5.5 Hz, 1H); 8.19 (ddd, J=1.5-2.5 and 8.5 Hz, 1H); 8.27 (s, 1H); 8.32 (d, J=2.5 Hz, 1H); 8.76 (d, J=2.5 Hz, 1H); 9.17 (s, 1H).

Mass Spectrum (ES): m/z=620 [M+H]$^+$; m/z=1261 [2M+Na]$^+$

Stage d): (2R)-2-amino-N-[5-{3-[(2-chloropyridin-4-yl)methyl]-4,4-dimethyl-2,5-dioxoimidazolidin-1-yl}-2-(trifluoromethoxy)phenyl]-2-phenylacetamide

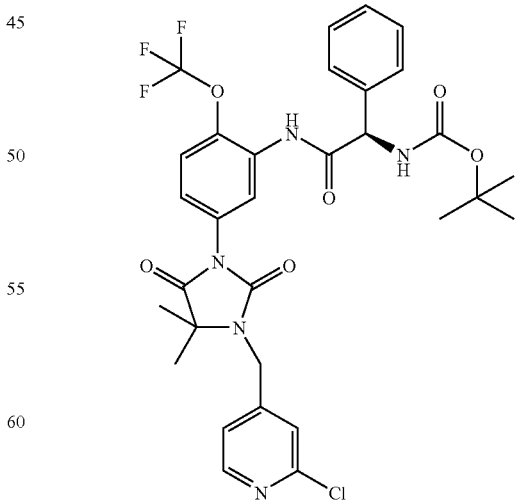

To a solution of 0.6 g of D-N-Boc-phenylglycine in 12 mL of dimethylformamide is added 0.74 g or O-(benzotriazol-1-yl)-N,N,N',N'-tetramethyluronium tetrafluoroborate (TBTU). After stirring for 5 minutes, 0.837 mL of triethylamine and 0.86 g of 3-[3-amino-4-(trifluoromethoxy)phenyl]-1-[(2-chloropyridin-4-yl)methyl]-5,5-dimethylimidazolidine-2,4-dione obtained in stage c) below are successively added. The reaction mixture is heated at 70° C. for 15 hours and then poured into 100 mL of water. The aqueous phase is extracted with three times 70 mL of ethyl acetate and the combined organic phases are washed with 50 mL of saturated sodium chloride solution, dried over magnesium sulphate, filtered and evaporated. The residue is purified by chromatography on a column of silica, eluting with a mixture of dichloromethane and ethyl acetate (70/30 by volume) to give 220 mg of (2R)-2-amino-N-[5-{3-[(2-chloropyridin-4-yl)methyl]-4,4-dimethyl-2,5-dioxoimidazolidin-1-yl}-2-(trifluoromethoxy)phenyl]-2-phenylacetamide, the characteristics of which are as follows:

1H NMR spectrum at 400 MHz: 1.40 (s, 15H); 4.62 (s, 2H); 5.53 (broad d, J=8.0 Hz, 1H); from 7.25 to 7.41 (m, 4H); 7.46 (broad d, J=5.5 Hz, 1H); from 7.48 to 7.56 (m, 4H); 7.59 (broad s, 1H); 8.00 (d, J=2.0 Hz, 1H); 8.37 (d, J=5.5 Hz, 1H); 10.0 (s, 1H).

Mass Spectrum (ES): m/z=662 [M+H]$^+$

Stage c): 3-[3-amino-4-(trifluoromethoxy)phenyl]-1-[(2-chloropyridin-4-yl)methyl]-5,5-dimethylimidazolidine-2,4-dione

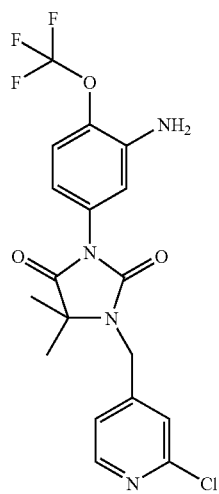

To a solution of 4.9 g of 3-[3-amino-4-(trifluoromethoxy)phenyl]-5,5-dimethylimidazolidine-2,4-dione obtained in stage b) below in 200 mL of dimethylformamide are added, under argon, 0.68 g of 60% sodium hydride and stirring is continued for 20 minutes at room temperature. To this solution are added 2.85 g of 2-chloro-4-chloromethylpyridine obtained in stage b) of Example 3 dissolved in 20 mL of dimethylformamide, and the reaction mixture is then heated at 70° C. for 3.5 hours and then poured into 500 mL of ice-water and extracted with three times 300 mL of ethyl acetate. The combined organic phases are dried over magnesium sulphate, filtered and concentrated under reduced pressure. The residue is taken up in 500 mL of diethyl ether, washed with water, dried over magnesium sulphate, filtered and concentrated under vacuum to give 6.8 g of 3-[3-amino-4-(trifluoromethoxy)phenyl]-1-[(2-chloropyridin-4-yl)methyl]-5,5-dimethylimidazolidine-2,4-dione, the characteristics of which are as follows:

1H NMR spectrum at 400 MHz: 1.39 (s, 6H); 4.62 (s, 2H); 5.59 (s, 2H); 6.62 (dd, J=2.5 and 8.5 Hz, 1H); 6.90 (d, J=2.5 Hz, 1H); 7.20 (broad d, J=8.5 Hz, 1H); 7.43 (broad d, J=5.5 Hz, 1H); 7.56 (broad s, 1H); 8.37 (d, J=5.5 Hz, 1H Mass Spectrum (ES): m/z=429 [M+H]$^+$ Stage b): 3-[3-amino-4-(trifluoromethoxy)phenyl]-5,5-dimethylimidazolidine-2,4-dione

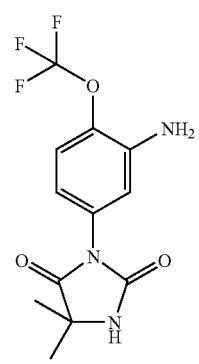

To a suspension of 6 g of 5,5-dimethyl-3-[3-nitro-4-(trifluoromethoxy)phenyl]imidazolidine-2,4-dione obtained in stage a) below in 180 mL of concentrated hydrochloric acid are added, portionwise, 33 g of zinc powder. The reaction mixture is heated at 50° C. for 5 hours and then cooled to room temperature and poured into a mixture of 500 mL of ethyl acetate and 200 mL of water. 5N sodium hydroxide solution is then added to pH 8, and the solid formed is filtered off through Celite and washed with ethyl acetate. The phases are separated, the aqueous phase is washed with ethyl acetate and the combined organic phases are dried over magnesium sulphate, filtered and concentrated under reduced pressure to give 4.96 g of 3-[3-amino-4-(trifluoromethoxy)phenyl]-5,5-dimethylimid-azolidine-2,4-dione in the form of a beige-coloured powder.

$R_f$: silica TLC=0.18 [dichloromethane/methanol (95/5 by volume)]

Stage a): 5,5-dimethyl-3-[3-nitro-4-(trifluoromethoxy)phenyl]imidazolidine-2,4-dione To a solution of 15 mL of trichloromethyl chloroformate (diphosgene) in 500 mL of toluene are added 3 g of 3S charcoal. To this suspension cooled to −20° C. are added 20 g of 3-nitro-4-trifluoromethoxyaniline dissolved in 400 mL of toluene. The reaction mixture is gradually warmed to room temperature and then refluxed for 4 hours. After cooling to room temperature, a suspension of 18 g of dimethylglycine ethyl ester hydrochloride in 150 mL of toluene is added, followed by 66 mL of triethylamine, and the reaction mixture is refluxed for 15 hours. After filtering through Celite, the filtrate is concentrated under reduced pressure and the residue is taken up in 500 mL of dichloromethane, washed with three times 100 mL of water, dried over magnesium sulphate, filtered and concentrated under reduced pressure. The residue is then triturated in diethyl ether and the solid formed is filtered off and dried to give 7.8 g of 5,5-dimethyl-3-[3-nitro-4-(trifluoromethoxy)phenyl]imidazolidine-2,4-dione, the characteristics of which are as follows:

1H NMR spectrum at 300 MHz: 1.42 (s, 6H); 7.90 (qd, J=1.0 and 9.0 Hz, 1H); 8.00 (dd, J=3.0 and 9.0 Hz, 1H); 8.37 (d, J=3.0 Hz, 1H); 8.75 (broad s, 1H).

Mass Spectrum (ES): m/z=332: [M−H]−

EXAMPLE 5B (2R)-2-amino-N-{5-(4,4-dimethyl-2,5-dioxo-3-{[2-(pyridin-3-ylamino)pyridin-4-yl]methyl}imidazolidin-1-yl)-2-[(trifluoromethyl)thio]phenyl}-2-phenylacetamide

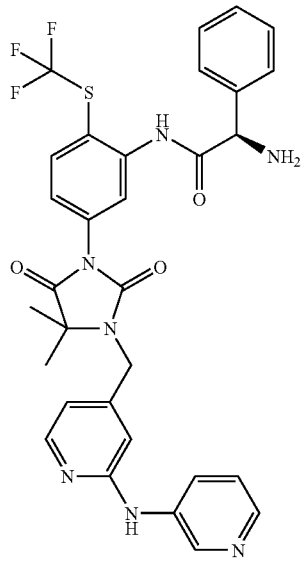

Stage f): (2R)-2-amino-N-{5-(4,4-dimethyl-2,5-dioxo-3-{[2-(pyridin-3-ylamino)pyridin-4-yl]methyl}imidazolidin-1-yl)-2-[(trifluoromethyl)thio]phenyl}-2-phenylacetamide To a solution of 33 mg of (2R)—N-(5-{3-[(2-chloropyridin-4-yl)methyl]-4,4-dimethyl-2,5-dioxoimidazolidin-1-yl}-2-[(trifluoromethyl)thio]phenyl)-2-[(9H-fluoren-9-ylacetyl)-amino]-2-phenylacetamide obtained in stage e) below in 1 mL of dioxane are successively added, under argon, 14 mg of 3-aminopyridine, 3 mg of (9,9-dimethyl-9H-xanthene-3,6-diyl)bis(diphenylphosphine) (Xantphos), 1.1 mg of palladium acetate and 61 mg of caesium carbonate. The reaction mixture is heated at 110° C. for 3 h, filtered and washed with twice 10 mL of dioxane, and the filtrate is then concentrated under reduced pressure. The residue is purified by HPLC (gradient: water/acetonitrile containing 0.1% formic acid) to give 5 mg of (2R)-2-amino-N-{5-(4,4-dimethyl-2,5-dioxo-3-{[2-(pyridin-3-ylamino)pyridin-4-yl]methyl}imidazolidin-1-yl)-2-[(trifluoromethyl)thio]phenyl}-2-phenylacetamide, the characteristics of which are as follows:

1H NMR spectrum at 400 MHz: 1.42 (s, 6H); 4.54 (s, 2H); 4.59 (s, 1H); 5.67 (very broad m, 2H); 6.82 (m, 2H); from 7.22 to 7.31 (m, 2H); 7.34 (broad t, J=7.5 Hz, 2H); 7.40 (dd, J=2.5 and 8.5 Hz, 1H); 7.43 (broad d, J=7.5 Hz, 2H); 7.89 (d, J=8.5 Hz, 1H); 8.08 (dd, J=1.5 and 5.5 Hz, 1H); 8.12 (m, 1H); 8.20 (ddd, J=1.5-2.5 and 8.5 Hz, 1H); 8.33 (broad s, 1H); 8.43 (d, J=2.5 Hz, 1H); 8.76 (d, J=2.5 Hz, 1H); 9.18 (s, 1H).

Mass Spectrum (ES): m/z=636 [M+H]+; m/z=634 [M−H]−

Stage e): (2R)—N-(5-{3-[(2-chloropyridin-4-yl)methyl]-4,4-dimethyl-2,5-dioxoimidazolidin-1-yl}-2-[(trifluoro-methyl)thio]phenyl)-2-[(9H-fluoren-9-ylacetyl)amino]-2-phenylacetamide.

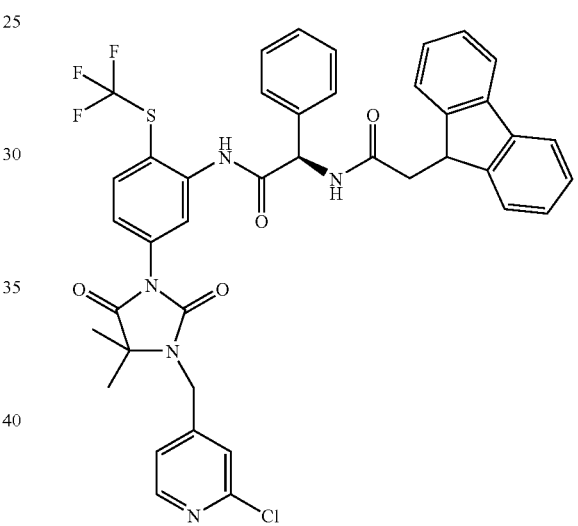

To a solution of 210 mg of 3-{3-amino-4-[(trifluoro-methyl)thio]phenyl}-1-[(2-chloropyridin-4-yl)methyl]-5,5-dimethylimidazolidine-2,4-dione obtained in stage d) below and 183 mg of D-N-FMOC-phenylglycine in 4.5 mL of 1,2-dichloroethane heated to 95° C. are added successively two drops of dimethylformamide and 72 μl of thionyl chloride. Heating is continued for 2.5 hours, the solvent is then concentrated under reduced pressure and the residue is purified by chromatography on a column of silica, eluting with a mixture of dichloromethane and methanol (98/2 by volume). The yellow residue obtained is again purified by HPLC (gradient: water/acetonitrile containing 0.1% formic acid) to give 145 mg of (2R)—N-(5-{3-[(2-chloropyridin-4-yl)methyl]-4,4-dimethyl-2,5-dioxoimidazolidin-1-yl}-2-[(trifluoromethyl)thio]phenyl)-2-[(9H-fluoren-9-ylacetyl)amino]-2-phenylacetamide, the characteristics of which are as follows:

1H NMR spectrum at 400 MHz: 1.40 (s, 6H); from 4.19 to 4.32 (m, 3H); 4.64 (s, 2H); 5.54 (d, J=8.0 Hz, 1H); from 7.22 to 7.51 (m, 10H); 7.58 (d, J=7.5 Hz, 2H); 7.60 (s, 1H); 7.78 (broad m, 2H); from 7.80 to 7.92 (m, 3H); 8.30 (broad d, J=8.0 Hz, 1H); 8.36 (d, J=5.5 Hz, 1H); 10.3 (s, 1H).

Mass Spectrum (ES): m/z=800 [M+H]+; m/z=798 [M−H]−

Stage d): 3-{3-amino-4-[(trifluoromethyl)thio]phenyl}-1-[(2-chloropyridin-4-yl)methyl]-5,5-dimethylimidazolidine-2,4-dione

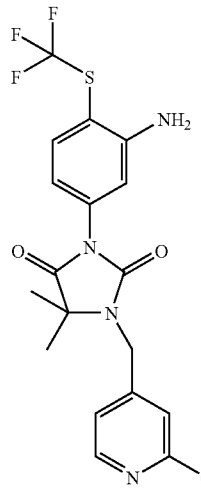

To a solution of 0.4 g of 3-{3-amino-4-[(trifluoro-methyl)thio]phenyl}-5,5-dimethylimidazolidine-2,4-dione obtained in stage c) below in 20 mL of dimethylformamide are added, under argon, 53 mg of 60% sodium hydride and stirring is continued for 20 minutes at room temperature. To this solution are added 2.85 g of 2-chloro-4chloromethylpyridine obtained in stage b) of Example 3 dissolved in 5 mL of dimethylformamide, and the reaction mixture is then heated at 70° C. for 3.5 hours and then poured into 100 mL of ice-water and extracted with three times 100 mL of ethyl acetate. The combined organic phases are dried over magnesium sulphate, filtered and concentrated under reduced pressure. The residue is taken up in 100 mL of diethyl ether, washed with water, dried over magnesium sulphate, filtered and concentrated under vacuum to give 500 mg of 3-{3-amino-4-[(trifluoromethyl)thio]phenyl}-1-[(2-chloropyridin-4-yl)methyl]-5,5-dimethylimidazolidine-2,4-dione, the characteristics of which are as follows:

1H NMR spectrum at 400 MHz: 1.40 (s, 6H); 4.63 (s, 2H); 6.01 (broad s, 2H); 6.70 (dd, J=2.5 and 8.0 Hz, 1H); 6.94 (d, J=2.5 Hz, 1H); from 7.40 to 7.50 (m, 2H); 7.58 (broad s, 1H); 8.39 (d, J=5.5 Hz, 1H).

Mass Spectrum (ES): m/z=445 [M+H]$^+$; m/z=443 [M−H]$^−$; m/z=489 [M−H]$^−$+HCOOH

Stage c): 3-{3-amino-4-[(trifluoromethyl)thio]phenyl}-5,5-dimethylimidazolidine-2,4-dione

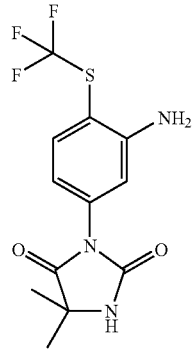

To a suspension of 1.75 g of 5,5-dimethyl-3-{3-nitro-4-[(trifluoromethyl)thio]phenyl}imidazolidine-2,4-dione obtained in stage b) below in 60 mL of concentrated hydrochloric acid are added, portionwise, 7.5 g of zinc powder. The reaction mixture is heated at 50° C. for 8 hours and then cooled to room temperature and poured into a mixture of 100 mL of ethyl acetate and 20 mL of water. 5N sodium hydroxide solution is then added to pH 8 and the solid formed is then filtered off through Celite and washed with ethyl acetate. The phases are separated, the aqueous phase is washed with ethyl acetate and the combined organic phases are dried over magnesium sulphate, filtered and concentrated under reduced pressure. The residue is purified by chromatography on a column of silica, eluting with a mixture of dichloromethane and methanol (95/5 by volume) to give 400 mg of 3-{3-amino-4-[(trifluoromethyl)thio]phenyl}-5,5-dimethylimidazolidine-2,4-dione, the characteristics of which are as follows:

1H NMR spectrum at 400 MHz: 1.39 (s, 6H); 5.98 (s, 2H); 6.62 (dd, J=2.5 and 8.0 Hz, 1H); 6.85 (d, J=2.5 Hz, 1H); 7.44 (d, J=8.0 Hz, 1H); 8.56 (broad s, 1H).

Stage b): 5,5-dimethyl-3-{3-nitro-4-[(trifluoromethyl)-thio]phenyl}imidazolidine-2,4-dione

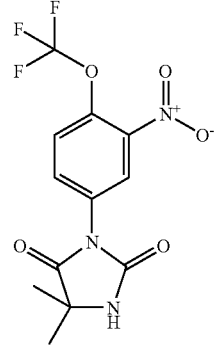

To a solution of 3.8 g of 5,5-dimethyl-3-{4-[(trifluoromethyl)thio]phenyl}imidazolidine-2,4-dione obtained in stage a) below in 7 mL of concentrated sulphuric acid is added dropwise at −5° C. a mixture of nitric acid (0.75 mL) in 3 mL of concentrated sulphuric acid. After stirring for 4 hours at 0° C. (ice bath) the mixture is poured onto 150 g of ice and the pH is raised to 10 by addition of concentrated aqueous ammonia. The aqueous phase is then extracted with twice 150 mL of ethyl acetate and the combined organic phases are dried over magnesium sulphate, filtered and concentrated under reduced pressure. The residue is purified by chromatography on a column of silica, eluting with a mixture of dichloromethane and methanol (95/5 by volume) to give 1.8 g of 5,5-dimethyl-3-{3-nitro-4-[(trifluoromethyl)thio]phenyl}imidazolidine-2, 4-dione, the characteristics of which are as follows:

1H NMR spectrum at 400 MHz: 1.41 (s, 6H); 7.80 (d, J=8.5 Hz, 2H); 8.00 (d, J=8.5 Hz, 2H); 8.71 (broad s, 1H).

Stage a): 5,5-dimethyl-3-{4-[(trifluoromethyl)thio]phenyl}-imidazolidine-2,4-dione

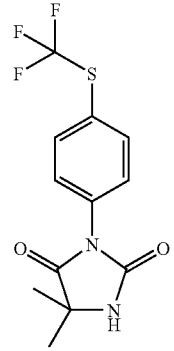

To a solution of 8.5 mL of trichloromethyl chloroformate (diphosgene) in 250 mL of toluene are added 1.8 g of 3S charcoal. To this suspension cooled to −20° C. are added 10 g of 4-trifluoromethylthioaniline dissolved in 160 mL of toluene. The reaction mixture is gradually warmed to room temperature and then refluxed for 4 hours. After cooling to room temperature, a suspension of 9.4 g of dimethylglycine ethyl ester hydrochloride in 90 mL of toluene is added, followed by 38 mL of triethylamine and the reaction mixture is refluxed for 15 hours. After filtering through Celite, the filtrate is concentrated under reduced pressure and the residue is taken up in 200 mL of dichloromethane, washed with three times 100 mL of water, dried over magnesium sulphate, filtered and concentrated under reduced pressure. The residue is then triturated in diethyl ether and the solid formed is filtered off and dried to give 12 g of 5,5-dimethyl-3-{4-[(trifluoromethyl)thio]phenyl}imidazolidine-2,4-dione, the characteristics of which are as follows:

1H NMR spectrum at 400 MHz: 1.40 (s, 6H); 7.60 (d, J=8.5 Hz, 2H); 7.82 (d, J=8.5 Hz, 2H); 8.65 (broad s, 1H).

Mass Spectrum (EI): m/z=304 [M]$^+$;
m/z=219 [M]$^+$−CONHCH(CH3)2; m/z=150 [219]$^+$−CF3

EXAMPLE 6A (2R)-2-amino-N-{5-[3-({2-[(dimethylcarbamoyl)-amino]pyridin-4-yl}methyl)-4,4-dimethyl-2,5-dioxoimidazolidin-1-yl]-2-(trifluoromethoxy)phenyl}-2-phenylacetamide

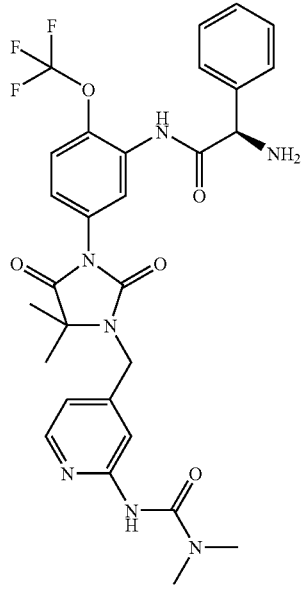

To a solution of 150 mg of (2R)-2-amino-N-[5-{3-[(2-chloropyridin-4-yl)methyl]-4,4-dimethyl-2,5-dioxoimidazolidin-1-yl}-2-(trifluoromethoxy)phenyl]-2-phenylacetamide obtained in stage d) of Example 5a in 10 mL of dioxane are successively added, under argon, 30 mg of N,N-dimethylurea, 13 mg of (9,9-dimethyl-9H-xanthene-3,6-diyl)bis(diphenylphosphine) (Xantphos), 5 mg of palladium acetate and 280 mg of caesium carbonate. The reaction mixture is refluxed for 1 hour and then filtered, and the filtrate is concentrated under reduced pressure. The residue is taken up in 10 mL of dioxane, 5 mL of a 4N solution of hydrogen chloride in dioxane are then added and the reaction mixture is stirred at 40° C. for 1 hour. After concentrating under reduced pressure, the residue is purified by HPLC (gradient: water/acetonitrile containing 0.1% formic acid) to give 45 mg of ((2R)-2-amino-N-{5-[3-({2-[(dimethylcarbamoyl)amino]pyridin-4-yl}methyl)-4,4-dimethyl-2,5-dioxoimidazolidin-1-yl]-2-(trifluoromethoxy)phenyl}-2-phenylacetamide, the characteristics of which are as follows:

1H NMR spectrum at 400 MHz: 1.39 (s, 6H); 2.92 (s, 6H); 4.56 (s, 2H); 4.62 (s, 1H); 6.98 (dd, J=1.5 and 5.5 Hz, 1H); from 7.23 to 7.38 (m, 4H); 7.42 (broad d, J=8.5 Hz, 2H); 7.58 (broad d, J=9.0 Hz, 1H); 7.82 (broad s, 1H); 8.15 (d, J=5.5 Hz, 1H); 8.19 (s, 1H); 8.29 (d, J=2.5 Hz, 1H); 8.79 (broad s, 1H).

Mass Spectrum (ES): m/z=612 [M−H]$^-$; m/z=614 [M+H]$^+$

EXAMPLE 6B (2R)-2-amino-N-{5-[3-({2-[(dimethylcarbamoyl)amino]pyridin-4-yl}methyl)-4,4-dimethyl-2,5-dioxoimidazolidin-1-yl]-2-[(trifluoromethyl)thio]phenyl}-2-phenylacetamide

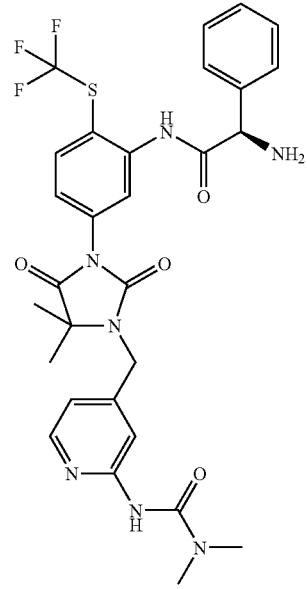

The product is prepared as in Example 5b, replacing the 3-aminopyridine with N,N-dimethylurea to give (2R)-2-amino-N-{5-[3-({2-[(dimethylcarbamoyl)amino]pyridin-4-yl}methyl)-4,4-dimethyl-2,5-dioxoimidazolidin-1-yl]-2-[(trifluoromethyl)thio]phenyl}-2-phenylacetamide, the characteristics of which are as follows:

LCMS: RT=3.09 min; m/z=609 [M+H]$^+$; m/z=607 [M−H]$^-$

EXAMPLE 7

3-(4-tert-butylphenyl)-5,5-dimethyl-1-{[2-(pyrimidin-5-ylamino)pyridin-4-yl]methyl}imidazolidine-2,4-dione Stage d: 3-(4-tert-butylphenyl)-5,5-dimethyl-1-{[2-(pyrimidin-5-ylamino)pyridin-4-yl]methyl}imidazolidine-2,4-dione

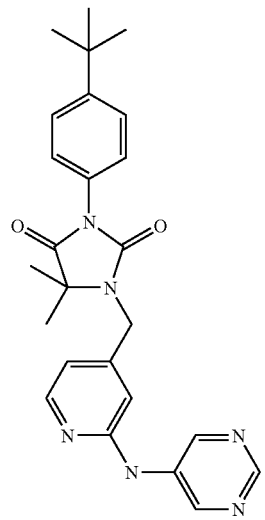

To a solution of 200 mg of 1-[(2-aminopyridin-4-yl)methyl]-3-(4-tert-butylphenyl)-5,5-dimethylimidazolidine-2,4-dione hydrochloride obtained in stage c) below in 5 mL of dioxane are successively added under argon 11.1 mg of palladium diacetate, 29 mg of (9,9-dimethyl-9H-xanthene-3,6-diyl)bis(diphenylphosphine)(Xantphos), 777 mg of caesium carbonate and 86.8 mg of 5-bromopyrimidine. The reaction mixture is heated at 100° C. for 5 hours and then filtered, and the filtrate is concentrated under reduced pressure. The residue is purified by chromatography on a column of silica, eluting with a mixture of dichloromethane, methanol and concentrated aqueous ammonia (95/4/1 by volume) to give 135 mg of 3-(4-tert-butylphenyl)-5,5-dimethyl-1-{[2-(pyrimidin-5-ylamino)pyridin-4-yl]methyl}imidazolidine-2,4-dione in the form of an off-white solid, the characteristics of which are as follows:

1H NMR spectrum at 400 MHz: 1.31 (s, 9H); 1.42 (s, 6H); 4.58 (s, 2H); 6.88 (broad s, 1H); 6.90 (broad d, J=5.5 Hz, 1H); 7.36 (broad d, J=9.0 Hz, 2H); 7.52 (broad d, J=9.0 Hz, 2H); 8.18 (d, J=5.5 Hz, 1H); 8.70 (s, 1H); 9.13 (s, 2H); 9.44 (s, 1H)

Mass Spectrum (ES): m/z=445 [M+H]$^+$ (base peak)

Stage c: 1-[(2-aminopyridin-4-yl)methyl]-3-(4-tert-butyl-phenyl)-5,5-dimethylimidazolidine-2,4-dione hydrochloride

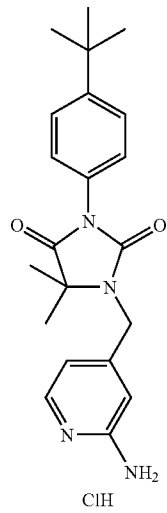

To a solution of 1.8 g of N-(4-{[3-(4-tert-butylphenyl)-5,5-dimethyl-2,4-dioxoimidazolidin-1-yl]methyl}pyridin-2-yl)acetamide obtained in stage b) below in 40 mL of dioxane are added 20.8 mL of 1N hydrochloric acid solution. The mixture is heated at 75° C. for six hours, 42 mL of 1N hydrochloric acid solution are then added and stirring is continued for 36 hours at the same temperature. The solution is then concentrated under reduced pressure to give 1.4 g of 1-[(2-aminopyridin-4-yl)methyl]-3-(4-tert-butylphenyl)-5,5-dimethylimidazolidine-2,4-dione hydrochloride in the form of a white powder, the characteristics of which are as follows:

LCMS: RT=3.25 min; m/z=367 [M+H]$^+$–HCl

Stage b: N-(4-{[3-(4-tert-butylphenyl)-5,5-dimethyl-2,4-dioxo-imidazolidin-1-yl]methyl}pyridin-2-yl)acetamide

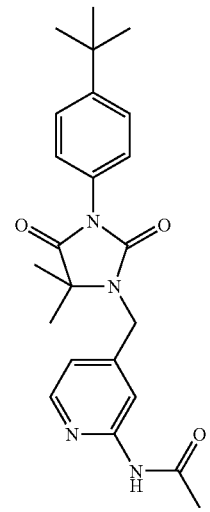

To a solution of 400 mg of 3-(4-tert-butylphenyl)-1-[(2-chloropyridin-4-yl)methyl]-5,5-dimethylimidazolidine-2,4-dione obtained in stage a) below in 12 mL of dioxane are successively added, under argon, 23.3 mg of palladium diacetate, 72 mg of (9,9-dimethyl-9H-xanthene-3,6-diyl)bis(diphenylphosphine)[Xantphos], 1.18 g of caesium carbonate and 153 mg of acetamide. After heating for one hour at a temperature in the region of 90° C. and chromatography on a column of silica, eluting with a mixture of diethyl ether/ethyl acetate (gradient up to 100% of ethyl acetate), 370 mg of N-(4-{[3-(4-tert-butylphenyl)-5,5-dimethyl-2,4-dioxoimidazolidin-1-yl]methyl}pyridin-2-yl)acetamide are obtained in the form of white crystals, the characteristics of which are as follows:

LCMS: RT=3.95 min; m/z=409 [M+H]$^+$

Stage a: 3-(4-tert-butylphenyl)-1-[(2-chloropyridin-4-yl)methyl]-5,5-dimethylimidazolidine-2,4-dione

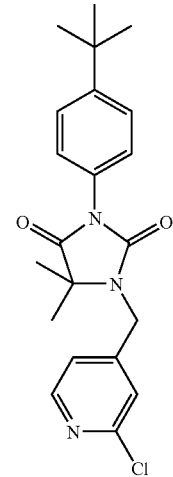

To a suspension of 1.1 g of sodium hydride in 40 mL of dimethylformamide under argon are successively added 4.9 g of 3-(4-tert-butylphenyl)-5,5-dimethylimidazolidine-2,4-dione obtained in stage c) of Example 1 and 4.55 g of 2-chloro-4-(chloromethyl)pyridine. The reaction mixture is stirred for 48 hours at room temperature and then diluted with 260 mL of water. The solid formed is filtered off, rinsed with diisopropyl ether and dried to give 4.61 g of 3-(4-tert-butylphenyl)-1-[(2-chloropyridin-4-yl)methyl]-5,5-dimethylimidazolidine-2,4-dione in the form of a beige-coloured powder, the characteristics of which are as follows:

Mass Spectrum (ES): m/z=386 [M+H]$^+$; m/z=430 [M−H+HCOOH]−

EXAMPLE 8

3-(4-tert-butylphenyl)-5,5-dimethyl-1-{[2-(pyrimidin-5-ylamino)pyrimidin-4-yl]methyl}imidazolidine-2,4-dione

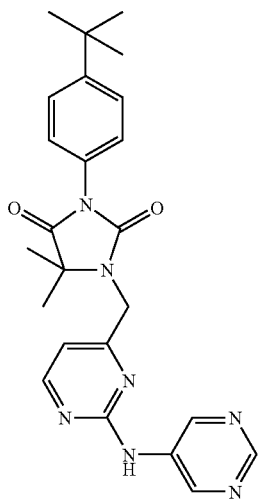

To a solution of 150 mg of 1-[(2-aminopyrimidin-4-yl)methyl]-3-(4-tert-butylphenyl)-5,5-dimethylimidazolidine-2,4-dione obtained in stage f) of Example 1 in 10 mL of dioxane are successively added, under argon, 18 mg of palladium diacetate, 56 mg of (9,9-dimethyl-9H-xanthene-3,6-diyl)bis(diphenylphosphine)(Xantphos), 505 mg of caesium carbonate and 129 mg of 5-bromopyridine. The reaction mixture is heated at 90° C. for 8 hours and then filtered, and the filtrate is concentrated under reduced pressure. The residue is purified by chromatography on a column of silica, eluting with a mixture of dichloromethane, acetonitrile and methanol (96/2/2 by volume) to give 45 mg of 3-(4-tert-butylphenyl)-5,5-dimethyl-1-{[2-(pyrimidin-5-ylamino)pyrimidin-4-yl]methyl}imidazolidine-2,4-dione in the form of white crystals, the characteristics of which are as follows:

1H NMR spectrum at 400 MHz: 1.31 (s, 9H); 1.43 (s, 6H); 4.63 (s, 2H); 7.04 (d, J=5.0 Hz, 1H); 7.39 (broad d, J=8.5 Hz, 2H); 7.51 (broad d, J=8.5 Hz, 2H); 8.52 (d, J=5.0 Hz, 1H); 8.78 (s, 1H); 9.19 (s, 2H); 10.0 (s, 1H)

Mass Spectrum (ES): m/z=446 [M+H]$^+$ (base peak);

m/z=444 [M−H]$^−$ (base peak)

Examples 2 to 8, the names and structures of which are described below, are prepared as indicated in the general schemes above in Example 1.

| Structure | Name |
|---|---|
|  | 3-(4-tert-butylphenyl)-5,5-dimethyl-1-[2-(pyridin-3-ylamino)pyrimidin-4-ylmethyl]imidazolidine-2,4-dione | ex 1

-continued
| Structure | Name |
|---|---|
| 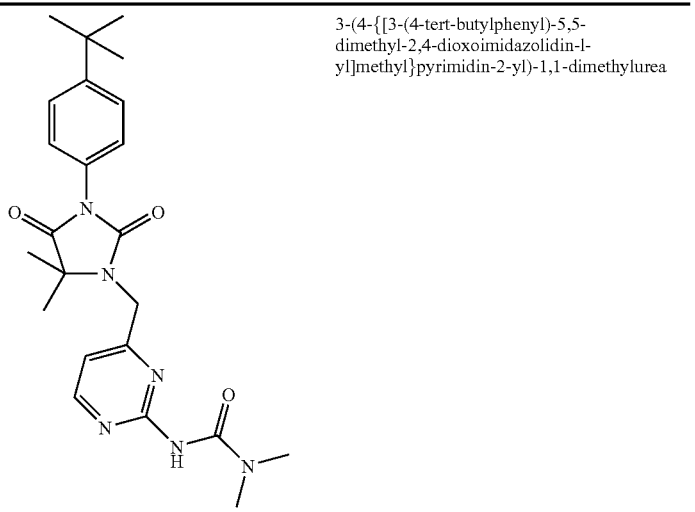 ex 2 | 3-(4-{[3-(4-tert-butylphenyl)-5,5-dimethyl-2,4-dioxoimidazolidin-l-yl]methyl}pyrimidin-2-yl)-1,1-dimethylurea |
| 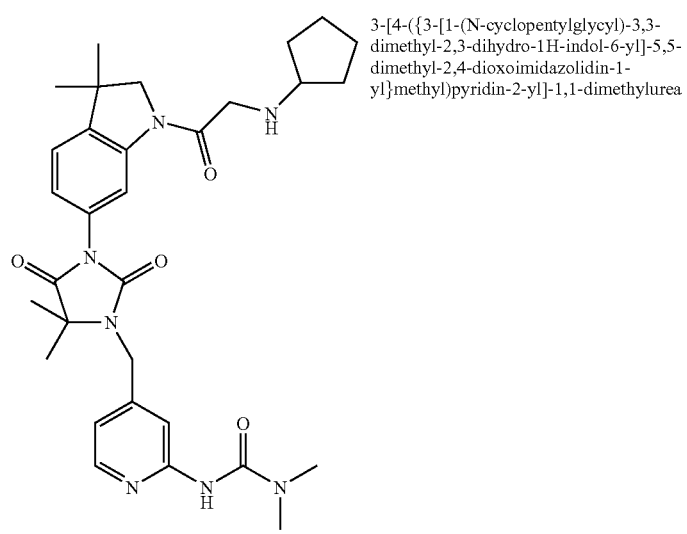 ex 3 | 3-[4-({3-[1-(N-cyclopentylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea |
| 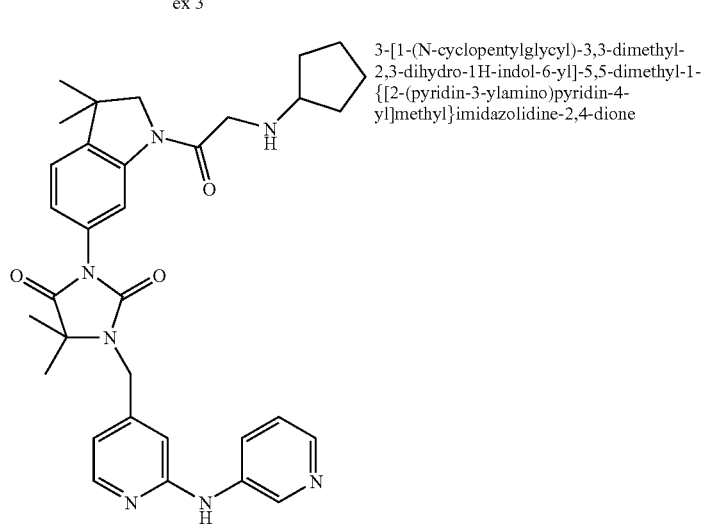 ex 4 | 3-[1-(N-cyclopentylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione |

-continued

| Structure | Name |
|---|---|
| ex 5 | Ex 5a X = O<br>(2R)-2-amino-N-[5-(4,4-dimethyl-2,5-dioxo-3-{[2-(pyridin-3-ylamino)pyridin-4-yl]methyl}imidazolidin-1-yl)-2-(trifluoromethoxy)phenyl]-2-phenylacetamide<br>Ex 5b X = S<br>(2R)-2-amino-N-{5-(4,4-dimethyl-2,5-dioxo-3-{[2-(pyridin-3-ylamino)pyridin-4-yl]methyl}imidazolidin-1-yl)-2-[(trifluoromethyl)thio]phenyl}-2-phenylacetamide |
| ex 6 | Ex 6a X = O<br>(2R)-2-amino-N-{5-[3-({2-[(dimethylcarbamoyl)amino]pyridin-4-yl}methyl)-4,4-dimethyl-2,5-dioxo-imidazolidin-1-yl]-2-(trifluoromethoxy)phenyl}-2-phenylacetamide<br>Ex 6b X = S<br>(2R)-2-amino-N-{5-[3-({2-[(dimethylcarbamoyl)amino]pyridin-4-yl}methyl)-4,4-dimethyl-2,5-dioxo-imidazalidin-1-yl]-2-[(trifluoromethyl)thio]phenyl}-2-phenylacetamide |
| ex 7 | 3-(4-tert-butylphenyl)-5,5-dimethyl-1-{[2-(pyrimidin-5-ylamino)pyridin-4-yl]methyl}imidazolidine-2,4-dione |

-continued

| Structure | Name |
|---|---|
| 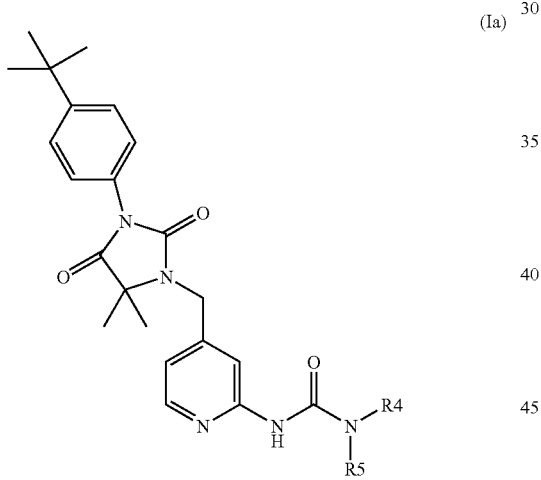 ex 8 | 3-(4-tert-butylphenyl)-5,5-dimethyl-1-{[2-(pyrimidin-5-ylamino)pyrimidin-4-yl]methyl}imidazolidine-2,4-dione |

The present invention especially comprises the products of formula (I) belonging to formula (Ia) below:

(Ia)

in which NR4R5 has the meaning given above.

The products of formula (Ia) may especially be prepared as indicated in the General Scheme 2 (compounds P and M).

Examples of products containing different radicals NR4R5 according to the present invention are given below: these products form part of the present invention.

ex 9

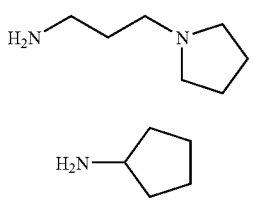

ex 10

-continued

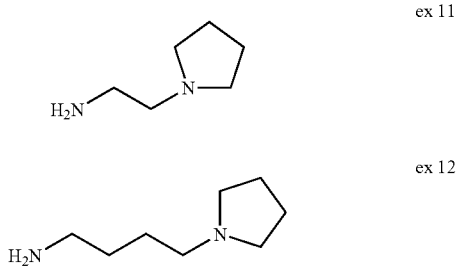

ex 11 ex 12

EXAMPLE 9

1-(4-{[3-(4-tert-butylphenyl)-5,5-dimethyl-2,4-dioxoimidazolidin-1-yl]methyl}pyridin-2-yl)-3-(3-pyrrolidin-1-ylpropyl)urea

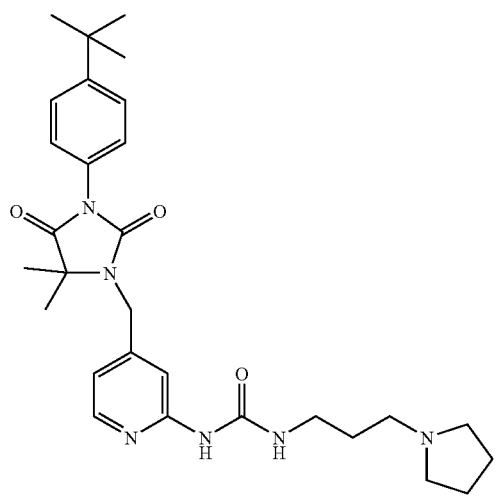

Stage c: 1-(4-{[3-(4-tert-butylphenyl)-5,5-dimethyl-2,4-dioxo-imidazolidin-1-yl]methyl}pyridin-2-yl)-3-(3-pyrrolidin-1-ylpropyl)urea To a solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) below in 2 mL of dimethyl sulphoxide are added 120 mg of 3-pyrrolidin-1-ylpropan-1-amine. The solution is stirred at a temperature of 100° C. for 1 hour 40 minutes. After cooling to a temperature in the region of 20° C., the reaction medium is diluted with water, the suspension is filtered and the precipitate is purified by chromatography on a column of silica, eluting with a dichloromethane/methanol/28% aqueous ammonia mixture (gradient from 100/0 to 75/20/5 by volume). 18.5 mg of 1-(4-{[3-(4-tert-butylphenyl)-5,5-dimethyl-2,4-dioxoimidazolidin-1-yl]methyl}pyridin-2-yl)-3-(3-pyrrolidin-1-ylpropyl)urea are obtained in the form of a pale yellow powder, the characteristics of which are as follows:

1H NMR spectrum at 400 MHz: 1.31 (s, 9H); 1.40 (s, 6H); from 1.57 to 1.70 (m, 6H); 2.41 (m, 6H); 3.21 (q, J=6.5 Hz, 2H) 4.56 (s, 2H); 6.92 (broad d, J=5.5 Hz, 1H); 7.31 (broad s, 1H); 7.34 (broad d, J=8.5 Hz, 2H); 7.51 (broad d, J=8.5 Hz, 2H); 8.11 (d, J=5.5 Hz, 1H); 8.27 (broad m, 1H); 9.13 (s, 1H)
Mass Spectrum (ES): m/z=521 [M+H]$^+$ (base peak); m/z=519 [M−H]$^-$ (base peak)

Stage b: 3-(4-tert-butylphenyl)-5,5-dimethyl-1-[(2-thioxo-2H-[1,2,4]oxadiazolo[2,3-a]pyridin-7-yl)methyl]imidazolidine-2,4-dione

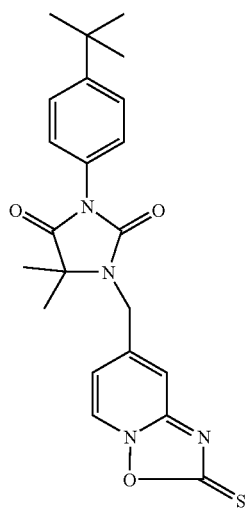

To a solution of 240 mg of N-(4-{[3-(4-tert-butylphenyl)-5,5-dimethyl-2,4-dioxoimidazolidin-1-yl]methyl}-1-oxidopyridin-2-yl)acetamide obtained in stage a) below in 6 mL of ethanol are added 109 mg of sodium hydrogen carbonate and 75 mg of thiocarbonyl dichloride. After stirring for 2 hours 30 minutes, the solid in suspension is filtered off, washed with ethanol and dried. 220 mg of 3-(4-tert-butylphenyl)-5,5-dimethyl-1-[(2-thioxo-2H-[1,2,4]oxadiazolo[2,3-a]pyridin-7-yl)methyl]imidazol-idine-2,4-dione are obtained in the form of a beige-coloured powder, the characteristics of which are as follows:
Mass Spectrum (ES): m/z=425 [M+H]$^+$; m/z=423 [M−H]$^-$

Stage a: N-(4-{[3-(4-tert-butylphenyl)-5,5-dimethyl-2,4-dioxoimidazolidin-1-yl]methyl}-1-oxidopyridin-2-yl)acetamide

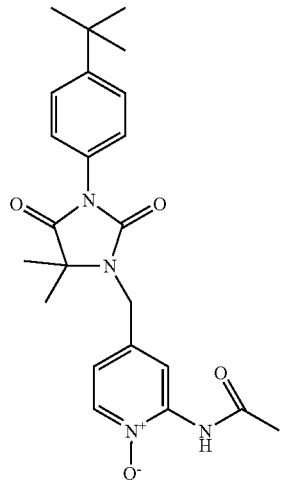

To a solution of 370 mg of N-(4-{[3-(4-tert-butylphenyl)-5,5-dimethyl-2,4-dioxoimidazolidin-1-yl]methyl}pyridin-2-yl)acetamide obtained in stage b) of Example 7 in 20 mL of dichloromethane are added, under argon, and with stirring, 704 mg of 3-chloroperbenzoic acid. After stirring for 1 hour 30 minutes at a temperature in the region of 20° C., 156 mg of 3-chloroperbenzoic acid are added. The solution is stirred overnight and then diluted with dichloromethane and washed three times with saturated aqueous sodium hydrogen carbonate solution. The organic phase is dried over magnesium sulphate, filtered and concentrated under reduced pressure. After chromatography on a column of silica, eluting with a dichloromethane/methanol/28% aqueous ammonia mixture (gradient from 100/0 to 90/9/1 by volume), 280 mg of N-(4-{[3-(4-tert-butylphenyl)-5,5-dimethyl-2,4-dioxoimidazolidin-1-yl]methyl}-1-oxidopyridin-2-yl)acetamide are obtained in the form of a yellow wax, the characteristics of which are as follows:
Mass Spectrum (ES): m/z=425 [M+H]$^+$; m/z=423 [M−H]$^-$

EXAMPLE 10

1-(4-{[3-(4-tert-butylphenyl)-5,5-dimethyl-2,4-dioxoimidazolidin-1-yl]methyl}pyridin-2-yl)-3-cyclopentylurea

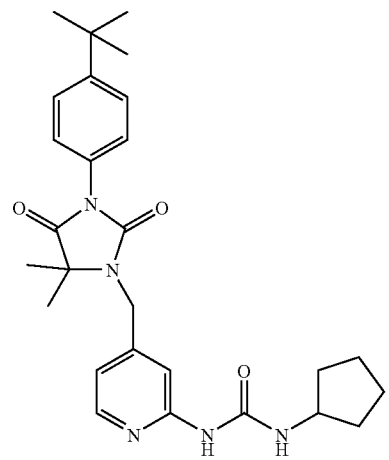

This compound may be prepared as obtained in stage c) of Example 9, but starting with 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 2 mL of dimethyl sulphoxide and 60 mg of cyclopentanamine. After chromatography on a column of silica, eluting with a mixture of diethyl ether/ethyl acetate (gradient from 100/0 to 0/100 by volume), 33 mg of 1-(4-{[3-(4-tert-butylphenyl)-5,5-dimethyl-2,4-dioxoimidazolidin-1-yl]methyl}pyridin-2-yl)-3-cyclopentylurea are obtained in the form of a white powder, the characteristics of which are as follows:

1H NMR spectrum at 400 MHz: 1.31 (s, 9H); 1.40 (s, 6H); 1.40 (masked m, 2H); 1.56 (m, 2H); 1.65 (m, 2H); 1.86 (m, 2H); 4.00 (m, 1H); 4.56 (s, 2H); 6.91 (dd, J=1.5 and 5.5 Hz, 1H); 7.34 (broad d, J=8.5 Hz, 2H); 7.36 (broad s, 1H); 7.51 (broad d, J=8.5 Hz, 2H); 8.11 (d, J=5.5 Hz, 1H); 8.18 (broad m, 1H); 9.09 (s, 1H)

Mass Spectrum (ES): m/z=478 [M+H]$^+$ (base peak); m/z=476 [M−H]$^-$

EXAMPLE 11

1-(4-{[3-(4-tert-butylphenyl)-5,5-dimethyl-2,4-dioxoimidazolidin-1-yl]methyl}pyridin-2-yl)-3-(2-pyrrolidin-1-ylethyl)urea This compound may be prepared as obtained in stage c) of Example 9, but starting with 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 2 mL of dioxane and 32.3 mg of 2-pyrrolidin-1-ylethanamine. After chromatography on a column of silica, eluting with a mixture of dichloromethane/methanol/28% aqueous ammonia (95/4/1 by volume), 42.4 mg of 1-(4-{[3-(4-tert-butylphenyl)-5,5-dimethyl-2,4-dioxoimidazolidin-1-yl]-methyl}pyridin-2-yl)-3-(2-pyrrolidin-1-ylethyl)urea are obtained in the form of a white powder, the characteristics of which are as follows:

1H NMR spectrum at 400 MHz: 1.32 (s, 9H); 1.40 (s, 6H); 1.69 (m, 4H); 2.47 (partially masked m, 4H); 2.52 (partially masked t, J=J=6.5 Hz, 2H); 3.27 (partially masked q, J=6.5 Hz, 2H); 4.56 (s, 2H); 6.91 (dd, J=1.5 and 5.5 Hz, 1H); 7.34 (broad d, J=9.0 Hz, 2H); 7.35 (broad s, 1H); 7.51 (broad d, J=9.0 Hz, 2H); 8.10 (d, J=5.5 Hz, 1H); 8.24 (broad m, 1H); 9.17 (broad s, 1H)

Mass Spectrum (ES): m/z=507 [M+H]$^+$

EXAMPLE 12

1-(4-{[3-(4-tert-butylphenyl)-5,5-dimethyl-2,4-dioxoimidazolidin-1-yl]methyl}pyridin-2-yl)-3-(4-pyrrolidin-1-ylbutyl)urea This compound may be prepared as obtained in stage c) of Example 9, but starting with 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 2 mL of dioxane and 40.2 mg of 4-pyrrolidin-1-ylbutan-1-amine. After chromatography on a column of silica, eluting with a mixture of dichloromethane/methanol/28% aqueous ammonia (95/4/1 by volume), 60.2 mg of 1-(4-{[3-(4-tert-butylphenyl)-5,5-dimethyl-2,4-dioxoimidazolidin-1-yl]-methyl}pyridin-2-yl)-3-(4-pyrrolidin-1-ylbutyl)urea are obtained in the form of a white powder, the characteristics of which are as follows:

1H NMR spectrum at 400 MHz: 1.32 (s, 9H); 1.40 (s, 6H); 1.48 (m, 4H); 1.65 (m, 4H); 2.38 (m, 6H); 3.17 (q, J=6.5 Hz, 2H); 4.56 (s, 2H); 6.92 (broad d, J=5.5 Hz, 1H); 7.31 (broad s, 1H); 7.34 (broad d, J=8.5 Hz, 2H); 7.51 (broad d, J=8.5 Hz, 2H); 8.11 (d, J=5.5 Hz, 1H); 8.25 (broad m, 1H); 9.12 (broad S, 1H)

Mass Spectrum (ES): m/z=535 [M+H]$^+$ (base peak); m/z=533 [M−H]$^-$

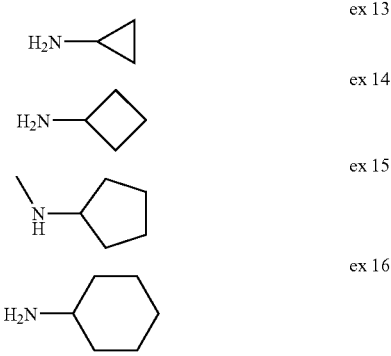

EXAMPLE 13

1-(4-{[3-(4-tert-butylphenyl)-5,5-dimethyl-2,4-dioxoimidazolidin-1-yl]methyl}pyridin-2-yl)-3-cyclopropylurea This compound may be prepared as obtained in stage c) of Example 9, but starting with 200 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 4 mL of ethanol and 32.3 mg of cyclopropanamine. After heating for one hour at a temperature of 50° C., and chromatography on a column of silica, eluting with a mixture of heptane/ethyl acetate (gradient from 100/0 to 0/100 by volume), 76.1 mg of 1-(4-{[3-(4-tert-butylphenyl)-5,5-dimethyl-2,4-dioxoimidazolidin-1-yl]methyl}pyridin-2-yl)-3-cyclopropylurea are obtained in the form of a white powder, the characteristics of which are as follows:

1H NMR spectrum at 400 MHz: 0.44 (m, 2H); 0.66 (m, 2H); 1.31 (s, 9H); 1.40 (s, 6H); 2.60 (m, 1H); 4.56 (s, 2H); 6.92 (dd, J=1.5 and 5.5 Hz, 1H); 7.34 (broad d, J=8.5 Hz, 2H); 7.36 (broad s, 1H); 7.52 (broad d, J=8.5 Hz, 2H); 8.11 (d, J=5.5 Hz, 1H); 8.24 (broad m, 1H); 9.09 (broad s, 1H)

Mass Spectrum (ES): m/z=450 [M+H]$^+$ (base peak)

EXAMPLE 14

1-(4-{[3-(4-tert-butylphenyl)-5,5-dimethyl-2,4-dioxoimidazolidin-1-yl]methyl}pyridin-2-yl)-3-cyclobutylurea This compound may be prepared as obtained in stage c) of Example 9, but starting with 200 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 4 mL of dioxane and 40.2 mg of cyclobutanamine. After chromatography on a column of silica, eluting with a mixture of heptane/ethyl acetate (gradient from 100/0 to 0/100 by volume), 112.6 mg of 1-(4-{[3-(4-tert-butylphenyl)-5,5-dimethyl-2,4-dioxoimidazolidin-1- yl]methyl}pyridin-2-yl)-3-cyclobutylurea are obtained in the form of a white powder, the characteristics of which are as follows:

1H NMR spectrum at 400 MHz: 1.31 (s, 9H); 1.40 (s, 6H); 1.65 (m, 2H); 1.88 (m, 2H); 2.24 (m, 2H); 4.18 (m, 1H); 4.56 (s, 2H); 6.92 (dd, J=1.5 and 5.5 Hz, 1H); 7.34 (broad d, J=8.5 Hz, 2H); 7.35 (broad s, 1H); 7.52 (broad d, J=8.5 Hz, 2H); 8.13 (d, J=5.5 Hz, 1H); 8.37 (broad d, J=8.0 Hz, 1H); 9.07 (broad s, 1H)

Mass Spectrum (ES): m/z=464 [M+H]$^+$ (base peak); m/z=462 [M−H]$^-$ (base peak)

EXAMPLE 15

3-(4-{[3-(4-tert-butylphenyl)-5,5-dimethyl-2,4-dioxoimidazolidin-1-yl]methyl}pyridin-2-yl)-1-cyclopentyl-1-methylurea

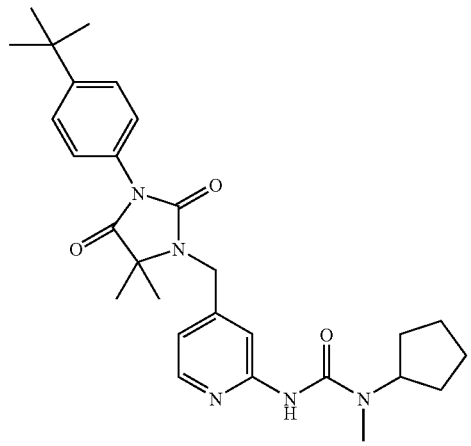

Stage b): 3-(4-{[3-(4-tert-butylphenyl)-5,5-dimethyl-2,4-dioxo-imidazolidin-1-yl]methyl}pyridin-2-yl)-1-cyclopentyl-1-methylurea To a solution of 0.16 g of ethyl (4-{[3-(4-tert-butylphenyl)-5,5-dimethyl-2,4-dioxoimidazolidin-1-yl]methyl}pyridin-2-yl)-carbamate obtained in stage a) below in 2 mL of tetrahydrofuran are added successively 0.368 mL of N-methylcyclopentylamine and 0.512 mL of triethylamine. The reaction mixture is heated by microwave at 130° C. for 3 hours and then concentrated under reduced pressure. The residue is purified by chromatography on a column of silica, eluting with a mixture of ethyl acetate and cyclohexane (60/40 by volume) to give 0.048 g of 3-(4-{[3-(4-tert-butylphenyl)-5,5-dimethyl-2,4-dioxoimidazolidin-1-yl]methyl}pyridin-2-yl)-1-cyclopentyl-1-methylurea, the characteristics of which are as follows:

1H NMR spectrum at 400 MHz: 1.31 (s, 9H); 1.39 (s, 6H); from 1.42 to 1.79 (m, 8H); 2.82 (s, 3H); 4.58 (s, 2H); 4.60 (m, 1H); 6.98 (dd, J=1.5 and 5.5 Hz, 1H); 7.33 (d, J=8.5 Hz, 2H); 7.51 (d, J=8.5 Hz, 2H); 7.85 (broad s, 1H); 8.17 (d, J=5.5 Hz, 1H); 8.72 (s, 1H).

Mass Spectrum (ES): m/z=492 [M+H]$^+$

Stage a): ethyl (4-{[3-(4-tert-butylphenyl)-5,5-dimethyl-2,4-dioxoimidazolidin-1-yl]methyl}pyridin-2-yl)carbamate

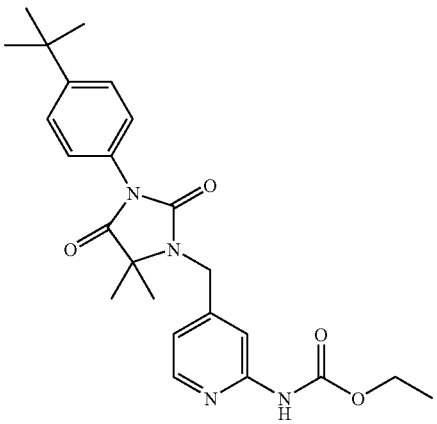

To a solution of 3.5 g of 3-(4-tert-butylphenyl)-1-[(2-chloropyridin-4-yl)methyl]-5,5-dimethylimidazolidine-2,4-dione obtained in stage a) of Example 7 in 90 mL of dioxane are successively added, under argon, 406 mg of palladium diacetate, 1.1 g of (9,9-dimethyl-9H-xanthene-3,6-diyl)bis(diphenylphosphine)[xantphos], 12.9 g of caesium carbonate and 1.86 g of ethyl carbamate. The reaction mixture is heated at 105° C. for 7 hours, filtered and concentrated under reduced pressure. The residue is purified by chromatography on a column of silica, eluting with a mixture of cyclohexane and ethyl acetate (60/40 by volume) to give 1.8 g of ethyl (4-{[3-(4-tert-butylphenyl)-5,5-dimethyl-2,4-dioxo-imidazolidin-1-yl]methyl}pyridin-2-yl)carbamate, the characteristics of which are as follows:

1H NMR spectrum at 300 MHz: 1.23 (t, J=7.5 Hz, 3H); 1.31 (s, 9H); 1.40 (s, 6H); 4.14 (q, J=7.5 Hz, 2H); 4.60 (broad s, 2H); 7.07 (broad d, J=5.5 Hz, 1H); 7.32 (d, J=8.5 Hz, 2H); 7.52 (d, J=8.5 Hz, 2H); 7.86 (broad s, 1H); 8.20 (d, J=5.5 Hz, 1H); 10.05 (broad s, 1H).

Mass Spectrum (ES): m/z=439 [M+H]$^+$; m/z=437 [M+H]$^+$

EXAMPLE 16

1-(4-{[3-(4-tert-butylphenyl)-5,5-dimethyl-2,4-dioxoimidazolidin-1-yl]methyl}pyridin-2-yl)-3-cyclohexylurea This compound may be prepared as obtained in stage c) of Example 9, but starting with 200 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 4 mL of ethanol and 56 mg of cyclohexanamine. After chromatography on a column of silica, eluting with a mixture of heptane/ethyl acetate (gradient from 100/0 to 0/100 by volume), 92 mg of 1-(4-{[3-(4-tert-butylphenyl)-5,5-dimethyl-2,4-dioxo-imidazolidin-1-yl]methyl}pyridin-2-yl)-3-cyclohexylurea are obtained in the form of a pale yellow powder, the characteristics of which are as follows:

1H NMR spectrum at 400 MHz: from 1.14 to 1.44 (m, 5H); 1.31 (s, 9H); 1.40 (s, 6H); 1.53 (m, 1H); 1.66 (m, 2H); 1.82 (m, 2H); 3.56 (m, 1H); 4.56 (s, 2H); 6.91 (dd, J=1.5 and 5.5

Hz, 1H); 7.33 (broad s, 1H); 7.34 (broad d, J=8.5 Hz, 2H); 7.51 (broad d, J=8.5 Hz, 2H); 8.11 (d, J=5.5 Hz, 1H); 8.20 (broad m, 1H); 9.06 (s, 1H)

Mass Spectrum (ES): m/z=492 [M+H]⁺ (base peak)
m/z=490 [M−H]⁻ (base peak)

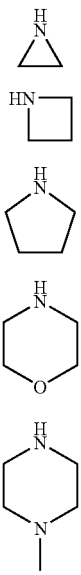

ex 17
ex 18
ex 19
ex 20
ex 21

EXAMPLE 17

N-(4-{[3-(4-tert-butylphenyl)-5,5-dimethyl-2,4-dioxoimidazolidin-1-yl]methyl}pyridin-2-yl)aziridine-1-carboxamide

EXAMPLE 18

N-(4-{[3-(4-tert-butylphenyl)-5,5-dimethyl-2,4-dioxoimidazolidin-1-yl]methyl}pyridin-2-yl)azetidine-1-carboxamide This compound may be prepared as obtained in stage c) of Example 9, but starting with 200 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 4 mL of dioxane and 32.3 mg of azetidine. After heating for 45 minutes at a temperature of 80° C. and purification par HPLC (gradient: water/acetonitrile containing 0.1% formic acid), 29 mg of N-(4-{[3-(4-tert-butylphenyl)-5,5-dimethyl-2,4-dioxoimidazolidin-1-yl]methyl}pyridin-2-yl)azetidine-1-carboxamide are obtained in the form of a white powder, the characteristics of which are as follows:

1H NMR spectrum at 400 MHz: 1.32 (s, 9H); 1.40 (s, 6H); 2.15 (m, 2H); 3.98 (m, 4H); 4.57 (s, 2H); 6.97 (dd, J=1.5 and 5.5 Hz, 1H); 7.33 (broad d, J=8.5 Hz, 2H); 7.51 (broad d, J=8.5 Hz, 2H); 7.94 (broad s, 1H); 8.16 (d, J=5.5 Hz, 1H); 8.95 (s, 1H)

Mass Spectrum (ES): m/z=450 [M+H]⁺ (base peak)

EXAMPLE 19

N-(4-{[3-(4-tert-butylphenyl)-5,5-dimethyl-2,4-dioxoimidazolidin-1-yl]methyl}pyridin-2-yl)pyrrolidine-1-carboxamide This compound may be prepared as obtained in stage c) of Example 9, but starting with 200 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 4 mL of dioxane and 40.2 mg of pyrrolidine. After chromatography on a column of silica, eluting with a mixture of heptane/ethyl acetate (gradient from 100/0 to 0/100 by volume), 64.3 mg of N-(4-{[3-(4-tert-butylphenyl)-5,5-dimethyl-2,4-dioxoimidazolidin-1-yl]methyl}pyridin-2-yl)pyrrolidine-1-carboxamide are obtained in the form of a beige-coloured powder, the characteristics of which are as follows:

1H NMR spectrum at 400 MHz: 1.31 (s, 9H); 1.40 (s, 6H); 1.84 (m, 4H); 3.40 (m, 4H); 4.58 (s, 2H); 6.98 (dd, J=1.5 and 5.5 Hz, 1H); 7.33 (d, J=9.0 Hz, 2H); 7.51 (d, J=9.0 Hz, 2H); 7.93 (broad s, 1H); 8.16 (d, J=5.5 Hz, 1H); 8.59 (s, 1H)

Mass Spectrum (ES): m/z=464 [M+H]⁺ (base peak)

EXAMPLE 20

N-(4-{[3-(4-tert-butylphenyl)-5,5-dimethyl-2,4-dioxoimidazolidin-1-yl]methyl}pyridin-2-yl)morpholine-4-carboxamide This compound may be prepared as obtained in stage c) of Example 9, but starting with 150 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 3 mL of dioxane and 36.9 mg of morpholine. After chromatography on a column of silica, eluting with a mixture of heptane/ethyl acetate (gradient from 100/0 to 0/100 by volume), 74 mg of N-(4-{[3-(4-tert-butylphenyl)-5,5-dimethyl-2,4-dioxo-imidazolidin-1-yl]methyl}pyridin-2-yl)morpholine-4-carboxamide are obtained in the form of a yellow wax, the characteristics of which are as follows:

1H NMR spectrum at 400 MHz: 1.32 (s, 9H); 1.39 (s, 6H); 3.45 (m, 4H); 3.59 (m, 4H); 4.58 (s, 2H); 7.00 (dd, J=1.5 and 5.5 Hz, 1H); 7.33 (broad d, J=8.5 Hz, 2H); 7.51 (broad d, J=8.5 Hz, 2H); 7.84 (broad s, 1H); 8.18 (d, J=5.5 Hz, 1H); 9.17 (s, 1H)

Mass Spectrum (ES): m/z=480 [M+H]⁺ (base peak)

EXAMPLE 21

N-(4-{[3-(4-tert-butylphenyl)-5,5-dimethyl-2,4-dioxoimidazolidin-1-yl]methyl}pyridin-2-yl)-4-methylpiperazine-1-carboxamide A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 31 µl of N-methylpiperazine is heated by microwave at 130° C. for 15 minutes. The reaction mixture is concentrated under reduced pressure and the residue is purified by HPLC (gradient: water/acetonitrile containing 0.1% formic acid) to give 94 mg of N-(4-{[3-(4-tert-butylphenyl)-5,5-dimethyl-2,4-dioxoimidazolidin-1-yl]methyl}pyridin-2-yl)-4-methylpiperazine-1-carboxamide, the characteristics of which are as follows:

1H NMR spectrum at 400 MHz: 1.30 (s, 9H); 1.40 (s, 6H); 2.19 (s, 3H); 2.29 (m, 4H); 3.46 (m, 4H); 4.58 (s, 2H); 6.99 (broad d, J=5.5 Hz, 1H); 7.33 (d, J=8.5 Hz, 2H); 7.51 (d, J=8.5 Hz, 2H); 7.81 (broad s, 1H); 8.18 (d, J=5.5 Hz, 1H); 9.13 (broad s, 1H).

Mass Spectrum (ES): m/z=493 [M+H]$^+$
m/z=267.6 [M+CH$_3$CN+H]$^{2+}$/2 base peak
m/z=247 [M+2H]$^{2+}$/2

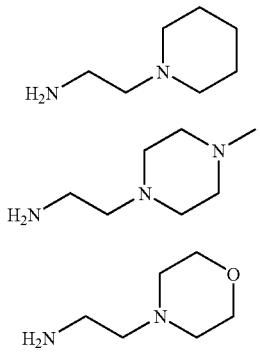

ex 22 ex 23 ex 24

EXAMPLE 22

1-(4-{[3-(4-tert-butylphenyl)-5,5-dimethyl-2,4-dioxoimidazolidin-1-yl]methyl}pyridin-2-yl)-3-(2-piperidin-1-ylethyl)urea A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 36 μl of 1-(2-aminoethyl)piperidine is heated by microwave at 130° C. for 15 minutes. The reaction mixture is concentrated under reduced pressure and the residue is purified by HPLC (gradient: water/acetonitrile containing 0.1% formic acid) to give 75 mg of 1-(4-{[3-(4-tert-butylphenyl)-5,5-dimethyl-2,4-dioxo-imidazolidin-1-yl]methyl}pyridin-2-yl)-3-(2-piperidin-1-ylethyl)urea, the characteristics of which are as follows:

1H NMR spectrum at 400 MHz: 1.31 (s, 9H); 1.40 (m, 8H); 1.52 (m, 4H); 2.44 (m, 6H); 3.27 (q, J=6.0 Hz, 2H); 4.56 (s, 2H); 6.91 (broad d, J=5.5 Hz, 1H); 7.29 (broad s, 1H); 7.33 (d, J=8.5 Hz, 2H); 7.51 (d, J=8.5 Hz, 2H); 8.11 (d, J=5.5 Hz, 1H); 8.43 (broad m, 1H); 9.23 (broad s, 1H).

Mass Spectrum (ES): m/z=521 [M+H]$^+$; m/z=281 [M+CH$_3$CN+H]$^{2+}$/2; m/z=261 [M+2H]$^{2+}$/2 base peak

EXAMPLE 23

1-(4-{[3-(4-tert-butylphenyl)-5,5-dimethyl-2,4-dioxoimidazolidin-1-yl]methyl}pyridin-2-yl)-3-[2-(4-methylpiperazin-1-yl)ethyl]urea A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 48 μl of 1-(2-aminoethyl)-4-methylpiperazine is heated by microwave at 130° C. for 15 minutes. The reaction mixture is concentrated under reduced pressure and the residue is purified by chromatography on a column of silica, eluting with a gradient (100/0 to 75/25 by volume) of dichloromethane and methanol/aqueous ammonia (6/1 by volume) to give 75 mg of 1-(4-{[3-(4-tert-butylphenyl)-5,5-dimethyl-2,4-dioxoimidazolidin-1-yl]methyl}pyridin-2-yl)-3-[2-(4-methylpiperazin-1-yl)ethyl]urea, the characteristics of which are as follows:

1H NMR spectrum at 400 MHz: 1.31 (s, 9H); 1.40 (s, 6H); 2.15 (s, 3H); from 2.25 to 2.45 (m, 10H); from 3.35 to 3.45 (masked m, 2H); 4.55 (s, 2H); 6.92 (broad d, J=5.5 Hz, 1H); 7.28 (broad s, 1H); 7.34 (d, J=8.5 Hz, 2H); 7.52 (d, J=8.5 Hz, 2H); 8.11 (d, J=5.5 Hz, 1H); 8.47 (broad t, J=6.0 Hz, 1H); 9.22 (broad s, 1H).

Mass Spectrum (ES): m/z=536 [M+H]$^+$; m/z=480 [M−tBu+2H]$^+$ base peak

EXAMPLE 24

1-(4-{[3-(4-tert-butylphenyl)-5,5-dimethyl-2,4-dioxoimidazolidin-1-yl]methyl}pyridin-2-yl)-3-(2-morpholin-4-ylethyl)urea A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 37 μl of 1-(2-aminoethyl)morpholine is heated by microwave at 130° C. for 15 minutes. The reaction mixture is concentrated under reduced pressure and the residue is purified by chromatography on a column of silica, eluting with a gradient (100/0 to 75/25 by volume) of dichloromethane and methanol/aqueous ammonia (6/1 by volume) to give 77 mg of 1-(4-{[3-(4-tert-butylphenyl)-5,5-dimethyl-2,4-dioxoimidazolidin-1-yl]methyl}pyridin-2-yl)-3-(2-morpholin-4-ylethyl)urea, the characteristics of which are as follows:

1H NMR spectrum at 400 MHz: 1.31 (s, 9H); 1.40 (s, 6H); 2.40 (m, 6H); from 3.35 to 3.45 (masked m, 2H); 3.60 (m, 4H); 4.56 (s, 2H); 6.93 (broad d, J=5.5 Hz, 1H); 7.29 (broad s, 1H); 7.34 (d, J=8.5 Hz, 2H); 7.52 (d, J=8.5 Hz, 2H); 8.12 (d, J=5.5 Hz, 1H); 8.48 (broad m, 1H); 9.22 (broad s, 1H).

Mass Spectrum (ES): m/z=523 [M+H]$^+$
m/z=282.6 [M+CH$_3$CN+H]$^{2+}$/2 base peak
m/z=262 [M+2H]$^{2+}$/2

ex 25

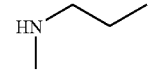

ex 26

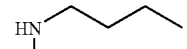

ex 27

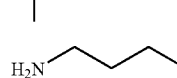

ex 28

EXAMPLE 25

3-(4-{[3-(4-tert-butylphenyl)-5,5-dimethyl-2,4-dioxoimidazolidin-1-yl]methyl}pyridin-2-yl)-1-ethyl-1-methylurea A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 24 μl of N-ethyl-N-methylamine is heated by microwave at 130° C. for 15 minutes. The reaction mixture is concentrated under reduced pressure and the residue is purified by chromatography on a column of silica, eluting with a mixture of petroleum ether and ethyl acetate (gradient 40/60 to 0/100 by volume) followed by HPLC (gradient: water/acetonitrile containing 0.1% formic acid) to give 12 mg of 3-(4-{[3-(4-tert-butylphenyl)-5,5-dimethyl-2,4-dioxo-imidazolidin-1-yl]methyl}pyridin-2-yl)-1-ethyl-1-methylurea, the characteristics of which are as follows:

1H NMR spectrum at 400 MHz: 1.07 (t, J=7.0 Hz, 3H); 1.31 (s, 9H); 1.40 (s, 6H); 2.93 (s, 3H); from 3.35 to 3.45 (masked m, 2H); 4.59 (s, 2H); 6.99 (broad d, J=5.5 Hz, 1H); 7.33 (d, J=8.5 Hz, 2H); 7.51 (d, J=8.5 Hz, 2H); 7.86 (broad s, 1H); 8.18 (d, J=5.5 Hz, 1H); 8.71 (broad s, 1H).

Mass Spectrum (ES): m/z=452 [M+H]+ base peak

EXAMPLE 26

3-(4-{[3-(4-tert-butylphenyl)-5,5-dimethyl-2,4-dioxoimidazolidin-1-yl]methyl}pyridin-2-yl)-1-methyl-1-propylurea A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 29 µl of N-methyl-N-propylamine is heated by microwave at 130° C. for 15 minutes. The reaction mixture is concentrated under reduced pressure and the residue is purified by chromatography on a column of silica, eluting with a mixture of petroleum ether and ethyl acetate (40/60 by volume) to give 61 mg of 3-(4-{[3-(4-tert-butylphenyl)-5,5-dimethyl-2,4-dioxoimidazolidin-1-yl]methyl}pyridin-2-yl)-1-methyl-1-propylurea in the form of a white powder, the characteristics of which are as follows:

1H NMR spectrum at 400 MHz:
0.85 (t, J=7.5 Hz, 3H); 1.31 (s, 9H); 1.39 (s, 6H); 1.52 (m, 2H); 2.94 (s, 3H); from 3.25 to 3.35 (masked m, 2H); 4.58 (s, 2H); 6.98 (dd, J=1.5 and 5.5 Hz, 1H); 7.33 (d, J=8.5 Hz, 2H); 7.50 (d, J=8.5 Hz, 2H); 7.85 (broad s, 1H); 8.18 (d, J=5.5 Hz, 1H); 8.72 (broad s, 1H). ES m/z=466 [M+H]+base peak

EXAMPLE 27

1-butyl-3-(4-{[3-(4-tert-butylphenyl)-5,5-dimethyl-2,4-dioxoimidazolidin-1-yl]methyl}pyridin-2-yl)-1-methylurea This compound may be prepared as obtained in stage c) of Example 9, but starting with 150 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 3 mL of dioxane and 36.9 mg of N-methylbutan-1-amine. After chromatography on a column of silica, eluting with a mixture of heptane/ethyl acetate (gradient from 100/0 to 0/100 by volume), 77.8 mg of 1-butyl-3-(4-{[3-(4-tert-butyl-phenyl)-5,5-dimethyl-2,4-dioxoimidazolidin-1-yl]methyl}pyridin-2-yl)-1-methylurea are obtained in the form of a white powder, the characteristics of which are as follows:

1H NMR spectrum at 400 MHz: 0.90 (t, J=7.5 Hz, 3H); 1.26 (m, 2H); 1.31 (s, 9H); 1.39 (s, 6H); 1.48 (m, 2H); 2.95 (s, 3H); 3.32 (partially masked t, J=7.5 Hz, 2H); 4.58 (s, 2H); 6.98 (dd, J=1.5 and 5.5 Hz, 1H); 7.34 (broad d, J=8.5 Hz, 2H); 7.51 (broad d, J=8.5 Hz, 2H); 7.85 (broad s, 1H); 8.17 (d, J=5.5 Hz, 1H); 8.70 (s, 1H)

Mass Spectrum (ES): m/z=480 [M+H]+ (base peak)

EXAMPLE 28

1-butyl-3-(4-{[3-(4-tert-butylphenyl)-5,5-dimethyl-2,4-dioxoimidazolidin-1-yl]methyl}pyridin-2-yl)urea This compound may be prepared as obtained in stage c) of Example 9, but starting with 200 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9, 4 mL of dioxane and 41.3 mg of butan-1-amine. After chromatography on a column of silica, eluting with a mixture of heptane/ethyl acetate (gradient from 100/0 to 0/100 by volume), 150.7 mg of 1-butyl-3-(4-{[3-(4-tert-butylphenyl)-5,5-dimethyl-2,4-dioxoimidazolidin-1-yl]methyl}pyridin-2-yl)urea are obtained in the form of a white powder, the characteristics of which are as follows:

1H NMR spectrum at 400 MHz: 0.90 (t, J=7.5 Hz, 3H); 1.31 (s, 9H); 1.33 (m, 2H); 1.40 (s, 6H); 1.45 (m, 2H); 3.17 (q, J=7.0 Hz, 2H); 4.56 (s, 2H); 6.91 (dd, J=1.5 and 5.5 Hz, 1H); 7.31 (broad s, 1H); 7.34 (broad d, J=8.5 Hz, 2H); 7.52 (broad d, J=8.5 Hz, 2H); 8.11 (d, J=5.5 Hz, 1H); 8.24 (broad m, 1H); 9.12 (s, 1H)

Mass Spectrum (ES): m/z=466 [M+H]+ (base peak)

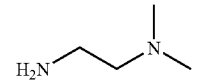 ex 29

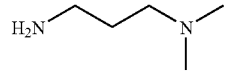 ex 30

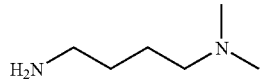 ex 31

EXAMPLE 29

1-(4-{[3-(4-tert-butylphenyl)-5,5-dimethyl-2,4-dioxoimidazolidin-1-yl]methyl}pyridin-2-yl)-3-[2-(dimethylamino)ethyl]urea A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 35 µl of N,N-dimethyl-1,3-ethylenediamine is heated by microwave at 130° C. for 15 minutes. The reaction mixture is concentrated under reduced pressure and the residue is purified by chromatography on a column of silica, eluting with a gradient (100/0 to 75/25 by volume) of dichloromethane and methanol/aqueous ammonia (6/1 by volume) to give 72 mg of 1-(4-{[3-(4-tert-butylphenyl)-5,5-dimethyl-2,4-dioxoimidazolidin-1-yl]methyl}pyridin-2-yl)-3-[2-(dimethylamino)ethyl]urea, the characteristics of which are as follows:

1H NMR spectrum at 400 MHz: 1.31 (s, 9H); 1.40 (s, 6H); 2.19 (s, 6H); 2.38 (m, 2H); 3.35 (q, J=6.0 Hz, 2H); 4.56 (s, 2H); 6.91 (dd, J=1.5 and 5.5 Hz, 1H); 7.34 (m, 3H); 7.51 (d, J=8.5 Hz, 2H); 8.11 (d, J=5.5 Hz, 1H); 8.19 (broad m, 1H); 9.19 (broad s, 1H).

Mass Spectrum (ES): m/z=481 [M+H]+ base peak

EXAMPLE 30

1-(4-{[3-(4-tert-butylphenyl)-5,5-dimethyl-2,4-dioxoimidazolidin-1-yl]methyl}pyridin-2-yl)-3-[3-(dimethylamino)propyl]urea A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 35 µl of N,N-dimethyl-1,3-propanediamine is heated by microwave at 130° C. for 15 minutes. The reaction mixture is concentrated under reduced pressure and the residue is purified by chromatography on a column of silica, eluting with a mixture of dichloromethane/methanol/aqueous ammonia (75/23/2 by volume) to give 72 mg of 1-(4-{[3-(4-tert-butylphenyl)-5,5-dimethyl-2,4-dioxoimidazolidin-1-yl]methyl}pyridin-2-yl)-3-[3-(dimethylamino)propyl]urea, the characteristics of which are as follows:

1H NMR spectrum at 400 MHz: 1.31 (s, 9H); 1.40 (s, 6H); 1.60 (m, 2H); 2.16 (s, 6H); 2.29 (m, 2H); 3.19 (q, J=6.0 Hz, 2H); 4.57 (s, 2H); 6.91 (broad d, J=5.5 Hz, 1H); 7.29 (broad s, 1H); 7.33 (d, J=8.5 Hz, 2H); 7.51 (d, J=8.5 Hz, 2H); 8.11 (d, J=5.5 Hz, 1H); 8.33 (broad m, 1H); 9.17 (broad s, 1H).

Mass Spectrum (ES): m/z=495 [M+H]$^+$ base peak

EXAMPLE 31

1-(4-{[3-(4-tert-butylphenyl)-5,5-dimethyl-2,4-dioxoimidazolidin-1-yl]methyl}pyridin-2-yl)-3-[4-(dimethylamino)butyl]urea A solution of 100 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 2 mL of dioxane and 35 µl of N,N-dimethyl-1, 3-propanediamine is heated by microwave at 130° C. for 15 minutes. The reaction mixture is concentrated under reduced pressure and the residue is purified by chromatography on a column of silica, eluting with a mixture of dichloromethane/methanol/aqueous ammonia (75/23/2 by volume) to give 77 mg of 1-(4-{[3-(4-tert-butylphenyl)-5,5-dimethyl-2,4-dioxoimidazolidin-1-yl]methyl}pyridin-2-yl)-3-[4-(dimethylamino)butyl]urea, the characteristics of which are as follows:

1H NMR spectrum at 400 MHz: 1.31 (s, 9H); 1.40 (s, 6H); 1.45 (m, 4H); 2.13 (s, 6H); 2.25 (m, 2H); 3.17 (q, J=6.0 Hz, 2H); 4.56 (s, 2H); 6.91 (dd, J=1.5 and 5.5 Hz, 1H); 7.30 (broad s, 1H); 7.34 (d, J=8.5 Hz, 2H); 7.52 (d, J=8.5 Hz, 2H); 8.11 (d, J=5.5 Hz, 1H); 8.28 (broad t, J=6.0 Hz, 1H); 9.14 (broad s, 1H).

Mass Spectrum (ES): m/z=509 [M+H]$^+$ base peak

EXAMPLE 31A 3-(4-tert-butylphenyl)-1-({2-[(5-fluoropyridin-3-yl)amino]pyridin-4-yl}methyl)-5,5-dimethylimidazolidine-2,4-dione

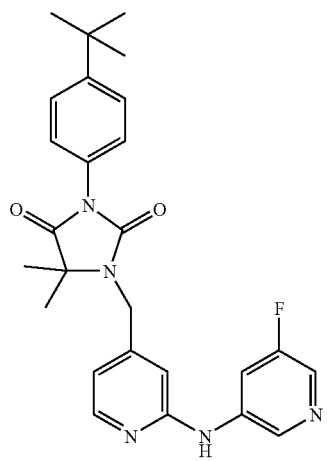

To a solution of 200 mg of 1-[(2-aminopyridin-4-yl)methyl]-3-(4-tert-butylphenyl)-5,5-dimethylimidazolidine-2,4-dione hydrochloride obtained in stage c) of Example 7 in 5 mL of dioxane are successively added under argon 11.1 mg of palladium diacetate, 29 mg of (9,9-dimethyl-9H-xanthene-3, 6-diyl)bis(diphenylphosphine) (xantphos), 777 mg of caesium carbonate and 96 mg of 5-bromo-3-fluoropyrimidine.

The reaction mixture is refluxed for 1 hour then filtered, and the filtrate is concentrated under reduced pressure. The residue is purified by chromatography on a column of silica, eluting with a mixture of dichloromethane and acetone (70/30 by volume) to give 210 mg of 3-(4-tert-butylphenyl)-1-({2-[(5-fluoropyridin-3-yl)amino]pyridin-4-yl}methyl)-5,5-dimethylimidazolidine-2,4-dione, the characteristics of which are as follows:

1H NMR spectrum at 400 MHz: 1.31 (s, 9H); 1.42 (s, 6H); 4.59 (s, 2H); 6.90 (m, 2H); 7.36 (d, J=8.5 Hz, 2H); 7.52 (d, J=8.5 Hz, 2H); 8.04 (d, J=2.5 Hz, 1H); 8.20 (d, J=5.5 Hz, 1H); 8.40 (td, J=2.5 and 12.0 Hz, 1H); 8.50 (t, J=2.5 Hz, 1H); 9.60 (s, 1H).

Mass Spectrum (ES): m/z=462 [M+H]$^+$

EXAMPLE 31B

3-[1-(N,N-dimethylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione

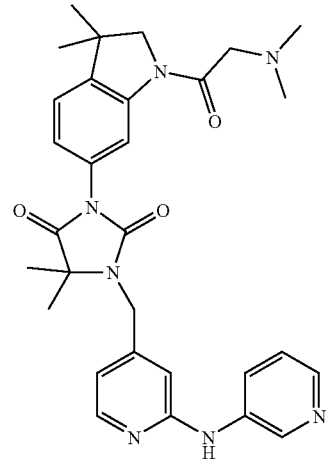

Stage b): 3-[1-(N,N-dimethylglycyl)-3,3-dimethyl-2, 3-dihydro-1H-indol-6-yl]-5,5-dimethyl-1-{[2-(pyridin-3-ylamino)pyridin-4-yl]methyl}imidazolidine-2, 4-dione To a solution of 242 mg of 1-[(2-chloropyridin-4-yl)methyl]-3-[1-(N,N-dimethylglycyl)-3,3-dimethyl-2,3-dihydro-1H-indol-6-yl]-5,5-dimethylimidazolidine-2,4-dione obtained in stage a) below in 2 mL of N-methylpyrrolidinone are successively added, under argon, 70 mg of 3-aminopyridine, 29 mg of (9,9-dimethyl-9H-xanthene-3,6-diyl)bis (diphenylphosphine) (Xantphos), 11 mg of palladium acetate and 652 mg of caesium carbonate. The reaction mixture is heated at 140° C. for 1 hour by microwave, cooled to room temperature, diluted with 10 mL of dichloromethane and filtered, and the filtrate is concentrated under reduced pressure. The residue is taken up in 30 mL of water and the precipitate formed is filtered off and purified by chromatography on a column of silica, eluting with a mixture of dichloromethane and methanol (93/7 by volume) to give 75 mg of 3-[1-(N,N-dimethylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione, the characteristics of which are as follows:

1H NMR spectrum at 400 MHz: 1.31 (s, 6H); 1.42 (s, 6H); 2.28 (s, 6H); 3.23 (s, 2H); 3.99 (s, 2H); 4.55 (s, 2H); 6.82 (m, 2H); 7.08 (dd, J=2.0 and 8.0 Hz, 1H); 7.27 (dd, J=5.0 and 8.5 Hz, 1H); 7.37 (d, J=8.0 Hz, 1H); 8.06 (broad s, 1H); 8.08 (dd, J=1.5 and 5.0 Hz, 1H); 8.13 (d, J=5.5 Hz, 1H); 8.21 (broad d, J=8.5 Hz, 1H); 8.78 (d, J=3.0 Hz, 1H); 9.21 (s, 1H).

Mass Spectrum (ES) m/z=542 [M+H]+; m/z=457 [M+H]+−Tbu (base peak); m/z=540 [M−H]−

Stage a): 1-[(2-chloropyridin-4-yl)methyl]-3-[1-(N,N-dimethylglycyl)-3,3-dimethyl-2,3-dihydro-1H-indol-6-yl]-5,5-dimethylimidazolidine-2,4-dione

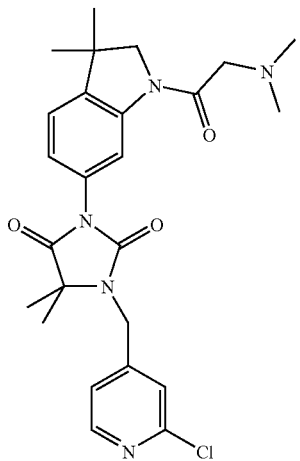

A solution of 0.951 g of 3-[1-(chloroacetyl)-3,3-dimethyl-2,3-dihydro-1H-indol-6-yl]-1-[(2-chloropyridin-4-yl)methyl]-5,5-dimethylimidazolidine-2,4-dione obtained in stage j) of Example 3 in 80 mL of a 2M solution of dimethylamine in tetrahydrofuran is heated at 60° C. for 4 hours. The reaction mixture is then concentrated under reduced pressure and is triturated in 30 mL of water. A solid forms, which is filtered off, washed with twice 5 mL of diisopropyl ether and dried to give 3.5 g of 1-[(2-chloropyridin-4-yl)methyl]-3-[1-(N,N-dimethylglycyl)-3,3-dimethyl-2,3-dihydro-1H-indol-6-yl]-5,5-dimethylimidazolidine-2,4-dione, the characteristics of which are as follows:

1H NMR spectrum at 400 MHz: 1.31 (s, 6H); 1.40 (s, 6H); 2.28 (s, 6H); 3.23 (s, 2H); 3.99 (s, 2H); 4.63 (s, 2H); 7.09 (broad d, J=8.0 Hz, 1H); 7.35 (d, J=8.0 Hz, 1H); 7.44 (broad d, J=5.5 Hz, 1H); 7.58 (broad s, 1H); 8.08 (broad s, 1H); 8.38 (d, J=5.5 Hz, 1H).

Mass Spectrum (ES): m/z=484 [M+H]+

EXAMPLE 31C

3-[4-({3-[1-(N,N-dimethylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea

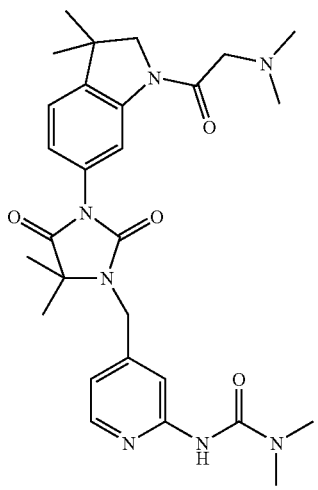

To a solution of 242 mg of 1-(2-chloropyridin-4-ylmethyl)-3-[1-(2-dimethylamino-acetyl)-3,3-dimethyl-2,3-dihydro-1H-indol-6-yl]-5,5-dimethyl-imidazolidine-2,4-dione obtained in stage a) of Example 31B in 10 mL of dioxane are successively added, under argon, 33 mg of N,N-dimethylurea, 29 mg of (9,9-dimethyl-9H-xanthene-3,6-diyl)bis(diphenylphosphine) (Xantphos), 22 mg of palladium acetate and 652 mg of caesium carbonate. The reaction mixture is refluxed for 6 hours, cooled to room temperature, filtered and washed with three times 10 mL of dichloromethane, and the filtrate is concentrated under reduced pressure. The residue is triturated in 20 mL of water and the precipitate formed is filtered off and purified twice by chromatography on a column of silica, eluting with a mixture of dichloromethane and methanol (93/7 by volume) to give 40 mg of 3-[4-({3-[1-(N,N-dimethylglycyl)-3,3-dimethyl-2,3-dihydro-1H-indol-6-yl]-5,5-dimethyl-2,4-dioxoimidazolidin-1-yl}methyl)-pyridin-2-yl]-1,1-dimethylurea, the characteristics of which are as follows:

1H NMR spectrum at 400 MHz: 1.37 (s, 6H); 1.49 (s, 6H); 2.89 (s, 6H); 3.07 (s, 6H); 4.39 (broad s, 2H); 4.76 (s, 2H); 7.30 (dd, J=1.5 and 8.0 Hz, 1H); 7.37 (broad d, J=5.5 Hz, 1H); 7.43 (d, J=8.0 Hz, 1H); 8.08 (d, J=1.5 Hz, 1H); 8.17 (broad s, 1H); 8.29 (d, J=5.5 Hz, 1H); 10.1 (broad m, 1H).

Mass Spectrum (ES): m/z=536 [M+H]+; m/z=406 [M+H]+—COCH2N(CH3)2−N(CH3)2 (base peak)

EXAMPLE 31D

3-[1-(N-ISOPROPYLGLYCYL)-3,3-DIMETHYL-2,3-DIHYDRO-1H-indol-6-yl]-5,5-dimethyl-1-{[2-(pyridin-3-ylamino)pyridin-4-yl]methyl}imidazolidine-2,4-dione

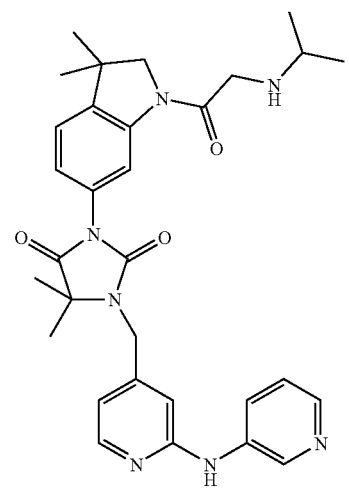

Stage b): 3-[1-(N-isopropylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione To a solution of 249 mg of 1-[(2-chloropyridin-4-yl)methyl]-3-[1-(N-isopropylglycyl)-3,3-dimethyl-2,3-dihydro- 1H-indol-6-yl]-5,5-dimethylimidazolidine-2,4-dione obtained in stage a) below in 3 mL of N-methylpyrrolidinone are successively added, under argon, 94 mg of 3-aminopyridine, 29 mg of (9,9-dimethyl-9H-xanthene-3,6-diyl)bis(diphenylphosphine) (Xantphos), 22 mg of palladium acetate and 652 mg of caesium carbonate. The reaction mixture is heated at 140° C. for 1 hour by microwave, cooled to room temperature, diluted with 20 mL of dichloromethane and filtered, and the filtrate is concentrated under reduced pressure. The residue is triturated in 40 mL of water and the precipitate formed is filtered off and purified by chromatography on a column of silica, eluting with a mixture of dichloromethane and methanol (93/7 by volume) to give 35 mg of 3-[1-(N-isopropylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione, the characteristics of which are as follows:

1H NMR spectrum at 400 MHz: 1.00 (d, J=6.5 Hz, 6H); 1.33 (s, 6H); 1.43 (s, 6H); 2.00 (very broad m, 1H); 2.75 (m, 1H); 3.49 (broad s, 2H); 3.91 (s, 2H); 4.54 (s, 2H); 6.82 (m, 2H); 7.09 (dd, J=1.5 and 8.0 Hz, 1H); 7.27 (dd, J=5.0 and 8.0 Hz, 1H); 7.38 (d, J=8.0 Hz, 1H); 8.08 (m, 2H); 8.12 (d, J=5.5 Hz, 1H); 8.21 (broad d, J=8.0 Hz, 1H); 8.78 (d, J=2.5 Hz, 1H); 9.21 (s, 1H).

Mass Spectrum (ES): m/z=55 [M+H]$^+$; m/z=279 [M+2H]$^+$+

Stage a): 1-[(2-chloropyridin-4-yl)methyl]-3-[1-(N-isopropylglycyl)-3,3-dimethyl-2,3-dihydro-1H-indol-6-yl]-5,5-dimethylimidazolidine-2,4-dione

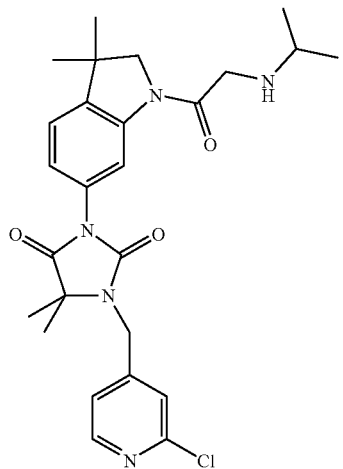

A solution of 1.426 g of 3-[1-(chloroacetyl)-3,3-dimethyl-2,3-dihydro-1H-indol-6-yl]-1-[(2-chloropyridin-4-yl)methyl]-5,5-dimethylimidazolidine-2,4-dione obtained in stage j) of Example 3 in 25 mL of isopropylamine is refluxed for 4 hours. The reaction mixture is then concentrated under reduced pressure and the residue is taken up in 30 mL of water and triturated in 2 mL of diethyl ether. A solid forms, which is filtered off, washed with twice 5 mL of diisopropyl ether and dried to give 1.2 g of 1-[(2-chloropyridin-4-yl)methyl]-3-[1-(N-isopropylglycyl)-3,3-dimethyl-2,3-dihydro-1H-indol-6-yl]-5,5-dimethylimidazolidine-2,4-dione, the characteristics of which are as follows:

1H NMR spectrum at 400 MHz: 1.00 (d, J=6.5 Hz, 6H); 1.32 (s, 6H); 1.40 (s, 6H); 1.95 (broad m, 1H); 2.75 (m, 1H); 3.48 (broad s, 2H); 3.91 (s, 2H); 4.63 (s, 2H); 7.10 (dd, J=2.0 and 8.0 Hz, 1H); 7.36 (d, J=8.0 Hz, 1H); 7.45 (broad d, J=5.5 Hz, 1H); 7.57 (broad s, 1H); 8.09 (broad s, 1H); 8.38 (d, J=5.5 Hz, 1H).

Mass Spectrum (ES): m/z=498 [M+H]$^+$

EXAMPLE 31E

3-[4-({3-[1-(N-ISOPROPYLGLYCYL)-3,3-DIMETHYL-2,3-dihydro-1H-indol-6-yl]-5,5-dimethyl-2,4-dioxoimidazolidin-1-yl}methyl)pyridin-2-yl]-1,1-dimethylurea

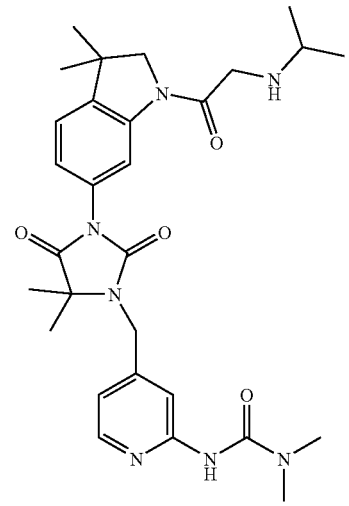

Stage b): 3-[4-({3-[1-(N-isopropylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea To a solution of 400 mg of tert-butyl [2-(6-{3-[(2-chloropyridin-4-yl)methyl]-4,4-dimethyl-2,5-dioxoimidazolidin-1-yl}-3,3-dimethyl-2,3-dihydro-1H-indol-1-yl)-2-oxoethyl]isopropylcarbamate obtained in stage a) below in 15 mL of dioxane are successively added, under argon, 88 mg of N,N-dimethylurea, 39 mg of (9,9-dimethyl-9H-xanthene-3,6-diyl)bis(diphenylphosphine) (Xantphos), 30 mg of palladium acetate and 872 mg of caesium carbonate. The reaction mixture is refluxed for 4 hours and filtered, and the filtrate is concentrated under reduced pressure. The residue is taken up in 30 mL of ethyl acetate, washed with three times 15 mL of water, dried over magnesium sulphate, filtered and concentrated under reduced pressure. The residue is purified by chromatography on a column of silica, eluting with a mixture of dichloromethane and methanol (90/10 by volume) to give 280 mg of a yellow lacquer, which is taken up in 10 mL of a 4N solution of hydrogen chloride in dioxane and stirred for 17 hours at room temperature. The reaction mixture is then concentrated under reduced pressure and is triturated in 20 mL of ethyl ether and the solid formed is filtered off and dried to give 200 mg of 3-[4-({3-[1-(N-isopropylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea in hydrochloride form, the characteristics of which are as follows:

1H NMR spectrum at 400 MHz: 1.29 (d, J=6.5 Hz, 6H); 1.38 (s, 6H); 1.47 (s, 6H); 3.04 (s, 6H); from 3.30 to 3.60 (masked m, 1H); 4.00 (s, 2H); 4.16 (t, J=6.0 Hz, 2H); 4.72 (s, 2H); 7.27 (dd, J=2.0 and 8.0 Hz, 1H); 7.30 (broad d, J=5.5 Hz, 1H); 7.43 (d, J=8.0 Hz, 1H); 8.05 (broad s, 1H); 8.09 (d, J=2.0 Hz, 1H); 8.28 (d, J=5.5 Hz, 1H); 8.96 (broad m, 2H); 10.6 (broad m, 1H).

Mass Spectrum (ES): m/z=550 [M+H]$^+$; m/z=406 [M+H]$^+$–COCH2N(CH3)2–N(CH3)2 (base peak)

Stage a): tert-butyl [2-(6-{3-[(2-chloropyridin-4-yl)methyl]-4,4-dimethyl-2,5-dioxoimidazolidin-1-yl}-3,3-dimethyl-2,3-dihydro-1H-indol-1-yl)-2-oxoethyl]isopropylcarbamate

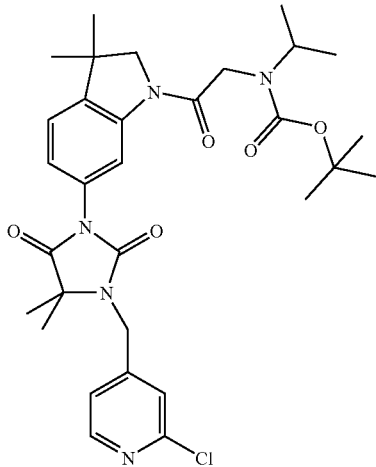

To a solution of 498 mg of 3-[1-(chloroacetyl)-3,3-dimethyl-2,3-dihydro-1H-indol-6-yl]-1-[(2-chloropyridin-4-yl)methyl]-5,5-dimethylimidazolidine-2,4-dione obtained in stage a) of Example 31D in 10 mL of dichloromethane are added successively 0.28 mL of triethylamine and 0.24 g of di-tert-butyl dicarbonate dropwise dissolved in 4 mL of dichloromethane. The reaction mixture is stirred at room temperature for 15 hours and then washed with three times 20 mL of water, dried over magnesium sulphate, filtered and concentrated under reduced pressure. The residue is purified by chromatography on a column of silica, eluting with a mixture of dichloromethane and methanol (95/5 by volume) and then crystallized from 10 mL of diethyl ether, filtered and dried to give 0.41 g of tert-butyl [2-(6-{3-[(2-chloropyridin-4-yl)methyl]-4,4-dimethyl-2,5-dioxo-imidazolidin-1-yl}-3,3-dimethyl-2,3-dihydro-1H-indol-1-yl)-2-oxoethyl]isopropylcarbamate, the characteristics of which are as follows:

1H NMR spectrum at 400 MHz: from 1.02 to 1.47 (m, 27H); from 3.91 to 4.32 (m, 5H); 4.63 (s, 2H); 7.09 (broad d, J=8.0 Hz, 1H); 7.38 (d, J=8.0 Hz, 1H); 7.45 (broad d, J=5.5 Hz, 1H); 7.57 (broad s, 1H); 8.08 (broad s, 1H); 8.38 (d, J=5.5 Hz, 1H).

Mass Spectrum (ES): m/z=598 [M+H]$^+$; m/z=498 [M+H]$^+$–COOtBu; m/z=642 [M–H]$^-$+HCOOH

EXAMPLE 31F 3-(4-tert-butylphenyl)-5,5-dimethyl-1-[(2-{[4-(pyrrolidin-1-ylmethyl)phenyl]amino}pyridin-4-yl)-methyl]imidazolidine-2,4-dione

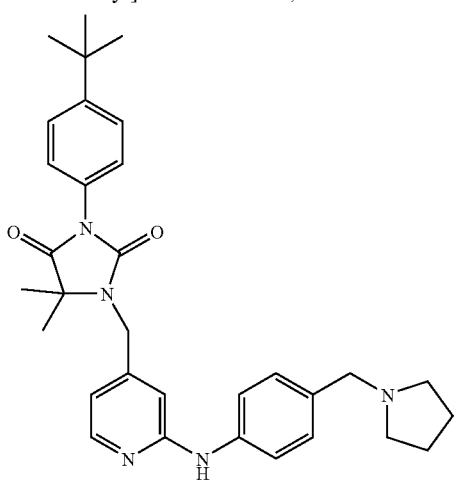

Stage d: 3-(4-tert-butylphenyl)-5,5-dimethyl-1-[(2-{[4-(pyrrolidin-1-ylmethyl)phenyl]amino}pyridin-4-yl)methyl]-imidazolidine-2,4-dione To a solution of 1.15 g of 3-(4-tert-butylphenyl)-1-[(2-chloropyridin-4-yl)methyl]-5,5-dimethylimidazolidine-2,4-dione obtained in stage a) of Example 7 in 50 mL of dioxane are successively added, under argon, 520 mg of 4-(pyrrolidin-1-ylmethyl)aniline obtained in stage c) below, 3.4 g of caesium carbonate, 207 mg of (9,9-dimethyl-9H-xanthene-3,6-diyl)bis(diphenylphosphine) [xantphos] and 67 mg of palladium diacetate. The reaction mixture is heated at 90° C. for 6 hours, filtered and concentrated under reduced pressure. The residue is purified by chromatography on a column of silica, eluting with a mixture of dichloromethane and methanol (90/10 by volume) to give 88 mg of 3-(4-tert-butylphenyl)-5,5-dimethyl-1-[(2-{[4-(pyrrolidin-1-ylmethyl)phenyl]amino}pyridin-4-yl)methyl]imidazolidine-2,4-dione, the characteristics of which are as follows:

1H NMR spectrum at 400 MHz: 1.31 (s, 9H); 1.41 (s, 6H); 1.78 (m, 4H); 2.40 (m, 4H); 3.49 (s, 2H); 4.51 (s, 2H); 6.73 (broad d, J=5.5 Hz, 1H); 6.79 (broad s, 1H); 7.18 (d, J=8.5 Hz, 2H); 7.34 (d, J=2H); 7.52 (d, J=8.5 Hz, 2H); 7.58 (d, J=8.5 Hz, 2H); 8.09 (d, J=5.5 Hz, 1H); 8.92 (s, 1H).

Mass Spectrum (ES): m/z=526 [M+H]$^+$; m/z=455 [M+H]$^+$–NH(CH2)4

Stage c: 4-(pyrrolidin-1-ylmethyl)aniline

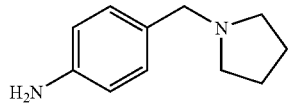

To a solution of 1.28 g of 4-(pyrrolidin-1-ylcarbonyl)aniline obtained in stage b) below in 100 mL of tetrahydrofuran are added, under argon, 1.28 g of lithium aluminium hydride. The reaction mixture is stirred for one hour at room temperature and then cooled to 0° C. and treated successively with 1.28 mL of water, 1.28 mL of 15% (by weight) sodium hydroxide solution and 3.85 mL of water. The solid formed is filtered off and washed with ethyl acetate, and the filtrate is concentrated under reduced pressure to give 1.1 g of 4-(pyrrolidin-1-ylmethyl)aniline in the form of a dark yellow oil, the characteristics of which are as follows:

1H NMR spectrum at 400 MHz: 1.64 (m, 4H); 2.34 (m, 4H); 3.37 (s, 2H); 4.88 (broad s, 2H); 6.49 (d, J=8.5 Hz, 2H); 6.91 (d, J=8.5 Hz, 2H).

Mass Spectrum (EI): m/z=176: [M]$^+$
m/z=106: [M]$^+$–N(CH2)4

Stage b: 4-(pyrrolidin-1-ylcarbonyl)aniline

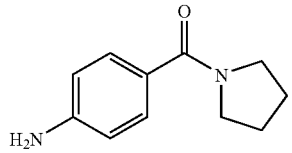

To a solution of 1.28 g of 1-(4-nitrobenzoyl)pyrrolidine obtained in stage a) below in 50 mL of methanol are added, under argon, 4.26 g of ammonium formate and 9 mg of 10% palladium-on-charcoal. The reaction mixture is stirred at room temperature for 5 hours and then filtered through Celite and concentrated under reduced pressure. The residue is taken up in water and extracted with ethyl acetate. The organic phase is then washed with saturated sodium chloride solution, dried over magnesium sulphate, filtered and concentrated under reduced pressure to give 1.28 g of 4-(pyrrolidin-1-ylcarbonyl)aniline, the characteristics of which are as follows:

1H NMR spectrum at 400 MHz: 1.80 (m, 4H); 3.43 (m, 4H); 5.45 (s, 2H); 6.52 (d, J=8.5 Hz, 2H); 7.28 (d, J=8.5 Hz, 2H).

Mass Spectrum (EI): m/z=190 [M]$^+$
m/z=120 [M]$^+$–N(CH2)4
m/z=92 [120]$^+$–CO

Stage a: 1-(4-nitrobenzoyl)pyrrolidine

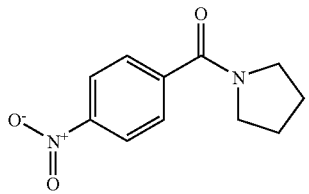

To a solution of 1.98 g of para-nitrobenzoic acid in 50 mL of dichloromethane are successively added under argon, at 0° C., 0.781 mL of pyrrolidine, 0.13 g of hydroxybenzotriazole, 2.3 g of 1,3-dimethylaminopropyl-3-ethyl carbodiimide and 3.43 mL of diisopropylamine. The reaction mixture is then stirred at room temperature for 15 hours and then washed with water. The organic phase is then washed with saturated sodium chloride solution, dried over magnesium sulphate, filtered and concentrated under reduced pressure. The residue is purified by chromatography on a column of silica, eluting with a mixture of ethyl acetate and cyclohexane (60/40 by volume) to give 1.9 g of (4-nitrophenyl)pyrrolidin-1-yl-methanone, the characteristics of which are as follows:

1H NMR spectrum at 400 MHz: from 1.78 to 1.93 (m, 4H); 3.33 (t, J=4.5 Hz, 2H); 3.50 (t, J=4.5 Hz, 2H); 7.78 (d, J=8.5 Hz, 2H); 8.28 (d, J=8.5 Hz, 2H).

Mass Spectrum (ES): m/z=221 [M+H]$^+$

EXAMPLE 31G 3-(4-tert-butylphenyl)-5,5-dimethyl-1-[(2-{[3-(pyrrolidin-1-ylmethyl)phenyl]amino}pyridin-4-yl)-methyl]imidazolidine-2,4-dione

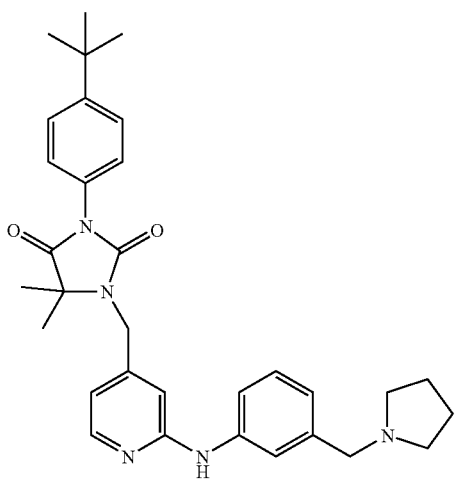

Stage d: 3-(4-tert-butylphenyl)-5,5-dimethyl-1-[(2-{[3-(pyrrolidin-1-ylmethyl)phenyl]amino}pyridin-4-yl)methyl]-imidazolidine-2,4-dione To a solution of 1.15 g of 3-(4-tert-butylphenyl)-1-[(2-chloropyridin-4-yl)methyl]-5,5-dimethylimidazolidine-2,4-dione obtained in stage a) of Example 7 in 50 mL of dioxane are successively added, under argon, 520 mg of 3-(pyrrolidin-1-ylmethyl)aniline obtained in stage c) below, 3.4 g of caesium carbonate, 207 mg of (9,9-dimethyl-9H-xanthene-3,6-diyl)bis(diphenylphosphine) [xantphos] and 67 mg of palladium diacetate. The reaction mixture is heated at 90° C. for 6 hours, filtered and concentrated under reduced pressure. The residue is purified by chromatography on a column of silica, eluting with a mixture of dichloromethane and methanol (90/10 by volume) to give 59 mg of 3-(4-tert-butylphenyl)-5,5-dimethyl-1-[(2-{[3-(pyrrolidin-1-ylmethyl)phenyl]amino}pyridin-4-yl)methyl]imidazolidine-2,4-dione, the characteristics of which are as follows:

1H NMR spectrum at 400 MHz: 1.31 (s, 9H); 1.41 (s, 6H); 1.69 (m, 4H); 2.41 (m, 4H); 3.51 (s, 2H); 4.52 (s, 2H); 6.73 (broad d, J=5.5 Hz, 1H); 6.80 (m, 2H); 7.18 (t, J=7.5 Hz, 1H); 7.34 (d, J=8.5 Hz, 2H); 7.49 (broad s, 1H); 7.52 (d, J=8.5 Hz, 2H); 7.66 (broad d, J=7.5 Hz, 1H); 8.10 (d, J=5.5 Hz, 1H); 8.94 (s, 1H).

Mass Spectrum (ES): m/z=526 [M+H]$^+$
m/z=570 [M–H]$^-$+HCOOH

Stage c: 3-(pyrrolidin-1-ylmethyl)aniline

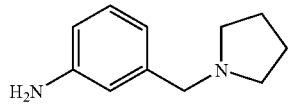

To a solution of 1.12 g of 3-(pyrrolidin-1-ylcarbonyl)aniline obtained in stage b) below in 100 mL of tetrahydrofuran are added, under argon, 0.89 g of lithium aluminium hydride. The reaction mixture is stirred for one hour at room temperature and then cooled to 0° C. and treated successively with 0.89 mL of water, 0.89 mL of 15% (by weight) sodium hydroxide solution and 2.67 mL of water. The solid formed is filtered off and washed with ethyl acetate, and the filtrate is concentrated under reduced pressure to give 1.02 g of 3-(pyrrolidin-1-ylmethyl)aniline, the characteristics of which are as follows:

1H NMR spectrum at 400 MHz: 1.78 (m, 4H); 2.39 (m, 4H); 3.39 (s, 2H); 4.92 (broad s, 2H); 6.41 (m, 2H); 6.52 (broad s, 1H); 6.91 (t, J=7.5 Hz, 1H).

Mass Spectrum (EI): m/z=176 [M]$^+$
m/z=106 [M]$^+$–N(CH2)4

Stage b: 3-(pyrrolidin-1-ylcarbonyl)aniline

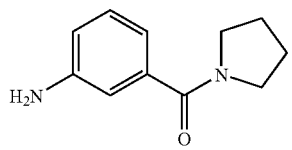

To a solution of 1.91 g of 1-(3-nitrobenzoyl)pyrrolidine obtained in stage a) below in 50 mL of methanol are added, under argon, 4.38 g of ammonium formate and 9 mg of 10% palladium-on-charcoal. The reaction mixture is stirred at room temperature for 1 hour and then filtered through Celite and concentrated under reduced pressure. The residue is taken up in water and extracted with ethyl acetate. The organic phase is then washed with saturated sodium chloride solution, dried over magnesium sulphate, filtered and concentrated under reduced pressure to give 1.12 g of 3-(pyrrolidin-1-ylcarbonyl)aniline, the characteristics of which are as follows:

1H NMR spectrum at 400 MHz: from 1.71 to 1.91 (m, 4H); from 3.25 to 3.48 (m, 4H); 5.15 (broad s, 2H); 6.59 (m, 2H); 6.64 (broad s, 1H); 7.02 (t, J=7.5 Hz, 1H).
Mass Spectrum (EI): m/z=190 [M]$^+$
m/z=120 [M]$^+$–N(CH2)4
m/z=92 [120]$^+$–CO Stage a: 1-(3-nitrobenzoyl)pyrrolidine

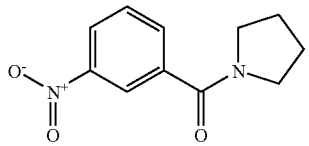

To a solution of 1.98 g of meta-nitrobenzoic acid in 50 mL of dichloromethane are successively added under argon, at 0° C., 0.81 mL of pyrrolidine, 0.13 g of hydroxybenzotriazole, 2.3 g of 1,3-dimethylaminopropyl-3-ethyl carbodiimide and 3.43 mL of diisopropylamine. The reaction mixture is then stirred at room temperature for 15 hours and then washed with water. The organic phase is then washed with saturated sodium chloride solution, dried over magnesium sulphate, filtered and concentrated under reduced pressure. The residue is purified by chromatography on a column of silica, eluting with a mixture of ethyl acetate and cyclohexane (60/40 by volume) to give 1.92 g of 1-(3-nitrobenzoyl)pyrrolidine, the characteristics of which are as follows:

1H NMR spectrum at 400 MHz: from 1.77 to 1.94 (m, 4H); 3.39 (t, J=5.0 Hz, 2H); 3.50 (t, J=5.0 Hz, 2H); 7.73 (t, J=7.5 Hz, 1H); 7.98 (broad d, J=7.5 Hz, 1H); from 8.24 to 8.33 (m, 2H).
Mass Spectrum (ES): m/z=221 [M+H]$^+$
m/z=265 [M–H]$^-$+HCOOH

EXAMPLE 31H 3-(4-tert-butylphenyl)-5,5-dimethyl-1-[(2-{[3-(2-pyrrolidin-1-ylethyl)phenyl]amino}pyridin-4-yl)-methyl]imidazolidine-2,4-dione

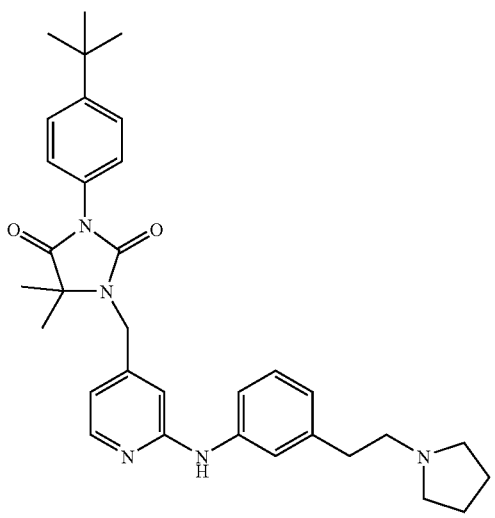

Stage d: 3-(4-tert-butylphenyl)-5,5-dimethyl-1-[(2-{[3-(2-pyrrolidin-1-ylethyl)phenyl]amino}pyridin-4-yl)-methyl]imidazolidine-2,4-dione To a solution of 1.15 g of 3-(4-tert-butylphenyl)-1-[(2-chloropyridin-4-yl)methyl]-5,5-dimethylimidazolidine-2,4-dione obtained in stage a) of Example 7 in 50 mL of dioxane are successively added, under argon, 567 mg of 3-(2-pyrrolidin-1-ylethyl)aniline obtained in stage c) below, 3.4 g of caesium carbonate, 207 mg of (9,9-dimethyl-9H-xanthene-3,6-diyl)bis(diphenylphosphine) [xantphos] and 67 mg of palladium diacetate. The reaction mixture is heated at 90° C. for 3 hours, filtered and concentrated under reduced pressure. The residue is purified by chromatography on a column of silica, eluting with a mixture of dichloromethane and methanol (90/10 by volume) to give 65 mg of 3-(4-tert-butylphenyl)-5,5-dimethyl-1-[(2-{[3-(2-pyrrolidin-1-ylethyl)phenyl]amino}pyridin-4-yl)methyl]imidazolidine-2,4-dione, the characteristics of which are as follows:

1H NMR spectrum at 400 MHz: 1.31 (s, 9H); 1.41 (s, 6H); 1.68 (m, 4H); 2.46 (m, 4H); from 2.55 to 2.71 (m, 4H); 4.52 (s, 2H); 6.74 (m, 2H); 6.80 (broad s, 1H); 7.13 (t, J=7.5 Hz, 1H); 7.33 (d, J=8.5 Hz, 2H); 7.41 (broad s, 1H); 7.51 (d, J=8.5 Hz, 2H); 7.54 (broad d, J=7.5 Hz, 1H); 8.10 (d, J=5.5 Hz, 1H); 8.90 (s, 1H).
Mass Spectrum (ES): m/z=540 [M+H]$^+$
m/z=442 [M+H]$^+$–(CH2)2N(CH2)4

Stage c: 3-(2-pyrrolidin-1-ylethyl)aniline

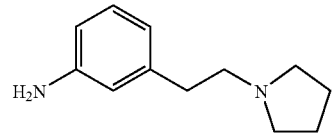

To a solution of 1.46 g of 3-(2-oxo-2-pyrrolidin-1-ylethyl)aniline obtained in stage b) below in 100 mL of tetrahydrofuran are added, under argon, 1.08 g of lithium aluminium hydride. The reaction mixture is stirred for one hour at room temperature and then cooled to 0° C. and treated successively with 1.08 mL of water, 1.08 mL of 15% (by weight) sodium hydroxide solution and 3.24 mL of water. The solid formed is filtered off and washed with ethyl acetate, and the filtrate is concentrated under reduced pressure to give 0.568 g of 3-(2-pyrrolidin-1-ylethyl)aniline, the characteristics of which are as follows:

1H NMR spectrum at 400: 1.65 (m, 4H); 2.42 (m, 4H); 2.54 (m, 4H); 4.89 (broad s, 2H); from 6.30 to 6.42 (m, 3H); 6.89 (t, J=7.5 Hz, 1H).
Mass Spectrum (ES): m/z=191 [M+H]$^+$ Stage b: 3-(2-oxo-2-pyrrolidin-1-ylethyl)aniline

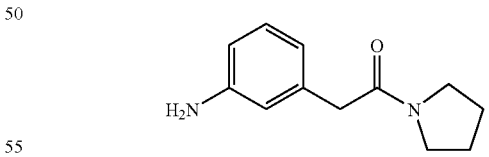

To a solution of 2.12 g of 1-[(3-nitrophenyl)acetyl]pyrrolidine obtained in stage a) below in 50 mL of methanol are added, under argon, 4.56 g of ammonium formate and 96 mg of 10% palladium-on-charcoal. The reaction mixture is stirred at room temperature for 1 hour and then filtered through Celite and concentrated under reduced pressure. The residue is taken up in water and extracted with dichloromethane. The organic phase is then washed with water and with saturated sodium chloride solution, dried over magnesium sulphate, filtered and concentrated under reduced pressure to give 1.46 g of 3-(2-oxo-2-pyrrolidin-1-ylethyl)aniline, the characteristics of which are as follows:

1H NMR spectrum at 400 MHz: from 1.69 to 1.90 (m, 4H); 3.39 (partially masked m, 2H); from 3.35 to 3.45 (m, 4H); 4.95 (broad s, 2H); 6.36 (broad d, J=7.5 Hz, 1H); 6.40 (broad d, J=7.5 Hz, 1H); 6.44 (broad s, 1H); 6.91 (t, J=7.5 Hz, 1H).

Mass Spectrum (ES): m/z=205 [M+H]$^+$

Stage a: 1-[(3-nitrophenyl)acetyl]pyrrolidine

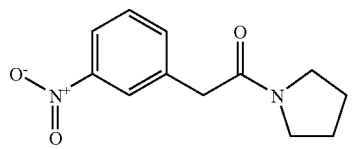

To a solution of 1.98 g of meta-nitrobenzoic acid in 50 mL of dichloromethane are successively added under argon, at 0° C., 0.81 mL of pyrrolidine, 0.13 g of hydroxybenzotriazole, 2.3 g of 1,3-dimethylaminopropyl-3-ethyl carbodiimide and 3.43 mL of diisopropylamine. The reaction mixture is then stirred at room temperature for 15 hours and washed with water. The organic phase is then washed with saturated sodium chloride solution, dried over magnesium sulphate, filtered and concentrated under reduced pressure. The residue is purified by chromatography on a column of silica, eluting with a mixture of ethyl acetate and cyclohexane (60/40 by volume) to give 1.92 g of 1-[(3-nitrophenyl)acetyl]pyrrolidine, the characteristics of which are as follows:

1H NMR spectrum at 400 MHz: 1.79 (m, 2H); 1.90 (m, 2H); 3.41 (partially masked t, J=5.0 Hz, 2H); 3.52 (t, J=5.0 Hz, 2H); 3.82 (s, 2H); 7.60 (t, J=7.5 Hz, 1H); 7.70 (broad d, J=7.5 Hz, 1H); 8.10 (broad d, J=7.5 Hz, 1H); 8.12 (broad s, 1H).

Mass Spectrum (ES): m/z=235 [M+H]$^+$

EXAMPLE 31I 3-(4-tert-butylphenyl)-1-({2-[(3-fluorophenyl)-amino]pyridin-4-yl}methyl)-5,5-dimethylimidazolidine-2,4-dione

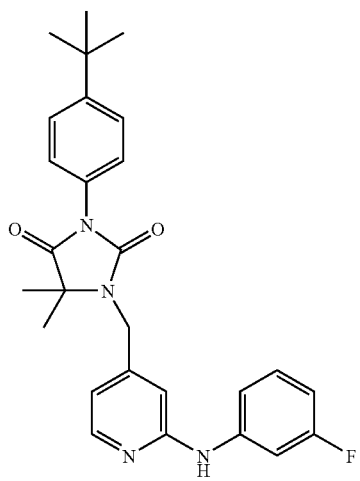

To a solution of 0.5 g of 3-(4-tert-butylphenyl)-1-[(2-chloropyridin-4-yl)methyl]-5,5-dimethylimidazolidine-2,4-dione obtained in stage a) of Example 7 in 15 mL of dioxane are successively added, under argon, 250 µl of 3-fluoroaniline, 1.6 g of caesium carbonate, 90 mg of (9,9-dimethyl-9H-xanthene-3,6-diyl)bis(diphenylphosphine) [xantphos] and 29 mg of palladium diacetate. The reaction mixture is heated at 95° C. for 2 hours, filtered and concentrated under reduced pressure. The residue is purified by chromatography on a column of silica, eluting with a mixture of cyclohexane and ethyl acetate (60/40 by volume) to give 451 mg of 3-(4-tert-butylphenyl)-1-({2-[(3-fluorophenyl)amino]pyridin-4-yl}methyl)-5,5-dimethyl-imidazolidine-2,4-dione, the characteristics of which are as follows:

1H NMR spectrum at 400 MHz: 1.31 (s, 9H); 1.41 (s, 6H); 4.54 (s, 2H); 6.66 (tt, J=2.0 and 8.5 Hz, 1H); 6.82 (m, 2H); from 7.20 to 7.32 (m, 2H); 7.37 (d, J=8.5 Hz, 2H); 7.52 (d, J=8.5 Hz, 2H); 7.83 (td, J=2.0 and 8.5 Hz, 1H); 8.16 (d, J=5.5 Hz, 1H); 9.28 (s, 1H).

Mass Spectrum (ES): m/z=461 [M+H]$^+$ m/z=459 [M−H]$^-$

EXAMPLE 31J 3-(4-tert-butylphenyl)-1-{[2-(cyclopropyl-amino)pyridin-4-yl]methyl}-5,5-dimethylimidazolidine-2,4-dione

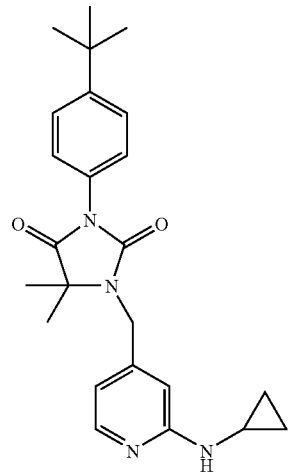

A suspension of 0.6 g of 3-(4-tert-butylphenyl)-1-[(2-chloropyridin-4-yl)methyl]-5,5-dimethylimidazolidine-2,4-dione obtained in stage a) of Example 7 in 1.1 mL of cyclopropylamine is heated by microwave at 150° C. for 6 hours and then concentrated under reduced pressure. The residue is purified by chromatography on a column of silica, eluting with a mixture of petroleum ether and ethyl acetate (50/50 by volume) to give 48 mg of 3-(4-tert-butylphenyl)-1-{[2-(cyclopropylamino)pyridin-4-yl]methyl}-5,5-dimethylimidazolidine-2,4-dione, the characteristics of which are as follows:

1H NMR spectrum at 400: 0.40 (m, 2H); 0.67 (m, 2H); 1.31 (s, 9H); 1.40 (s, 6H); 2.50 (masked m, 1H); 4.48 (s, 2H); 6.55 (m, 2H); 6.71 (broad m, 1H); 7.32 (d, J=8.5 Hz, 2H); 7.51 (d, J=8.5 Hz, 2H); 7.93 (d, J=5.5 Hz, 1H).

Mass Spectrum (ES): m/z=407: [M+H]$^+$

EXAMPLE 31K 3-(4-tert-butylphenyl)-1-({2-[(2-chloropyridin-3-yl)amino]pyridin-4-yl}methyl)-5,5-dimethylimidazolidine-2,4-dione

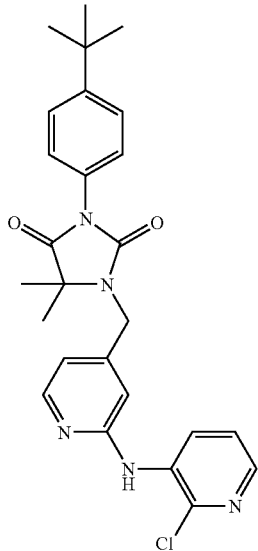

To a solution of 0.8 g of 1-[(2-aminopyridin-4-yl)methyl]-3-(4-tert-butylphenyl)-5,5-dimethylimidazolidine-2,4-dione hydrochloride obtained in stage c) of Example 7 in 50 mL of dioxane are successively added under argon 0.628 g of 2-chloro-3-iodopyridine, 2.8 g of caesium carbonate, 150 mg of (9,9-dimethyl-9H-xanthene-3,6-diyl)bis(diphenylphosphine) (xantphos) and 49 mg of palladium diacetate. The reaction mixture is heated at 90° C. for 3 hours and then filtered, and the filtrate is concentrated under reduced pressure. The residue is purified by chromatography on a column of silica, eluting with a mixture of cyclohexane and ethyl acetate (70/30 by volume) to give 0.51 g of 3-(4-tert-butylphenyl)-1-({2-[(2-chloropyridin-3-yl)amino]pyridin-4-yl}methyl)-5,5-dimethylimidazolidine-2,4-dione, the characteristics of which are as follows:

1H NMR spectrum at 400 MHz: 1.31 (s, 9H); 1.43 (s, 6H); 4.57 (s, 2H); 6.89 (dd, J=1.5 and 5.5 Hz, 1H); 7.11 (broad s, 1H); 7.39 (m, 3H); 7.52 (d, J=8.5 Hz, 2H); 8.00 (dd, J=2.0 and 5.0 Hz, 1H); 8.10 (d, J=5.5 Hz, 1H); 8.55 (m, 2H).

Mass Spectrum (ES): m/z=478 [M+H]$^+$; m/z=476 [M−H]$^−$

EXAMPLE 31L 3-(4-tert-butylphenyl)-1-({2-[(6-chloropyridin-3-yl)amino]pyridin-4-yl}methyl)-5,5-dimethylimidazolidine-2,4-dione

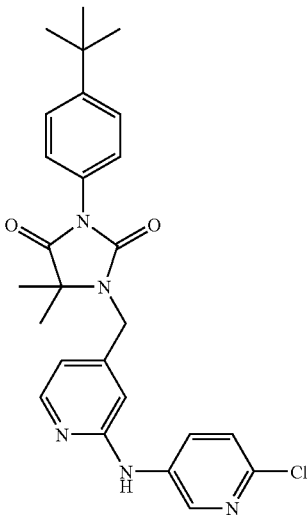

To a solution of 0.5 g of 1-[(2-aminopyridin-4-yl)methyl]-3-(4-tert-butylphenyl)-5,5-dimethylimidazolidine-2,4-dione hydrochloride obtained in stage c) of Example 7 in 35 mL of dioxane are successively added under argon 0.39 g of 2-chloro-5-iodopyridine, 1.8 g of caesium carbonate, 947 mg of (9,9-dimethyl-9H-xanthene-3,6-diyl)bis(diphenylphosphine) (xantphos) and 30 mg of palladium diacetate. The reaction mixture is heated at 90° C. for 3 hours and then filtered, and the filtrate is concentrated under reduced pressure. The residue is purified by chromatography on a column of silica, eluting with a mixture of cyclohexane and ethyl acetate (62/38 by volume) to give 0.368 g of 3-(4-tert-butylphenyl)-1-({2-[(6-chloropyridin-3-yl)amino]pyridin-4-yl}methyl)-5,5-dimethylimidazolidine-2,4-dione, the characteristics of which are as follows:

1H NMR spectrum at 400 MHz: 1.31 (s, 9H); 1.41 (s, 6H); 4.57 (s, 2H); 6.85 (m, 2H); 7.35 (d, J=8.5 Hz, 2H); 7.39 (d, J=8.5 Hz, 1H); 7.52 (d, J=8.5 Hz, 2H); 8.16 (d, J=5.5 Hz, 1H); 8.27 (dd, J=2.5 and 8.5 Hz, 1H); 8.65 (d, J=2.5 Hz, 1H); 9.40 (s, 1H)

Mass Spectrum (ES): m/z=478 [M+H]$^+$; m/z=476 [M−H]$^−$

EXAMPLE 31M 3-(4-tert-butylphenyl)-1-({2-[(6-hydroxypyridin-3-yl)amino]pyridin-4-yl}methyl)-5,5-dimethylimidazolidine-2,4-dione

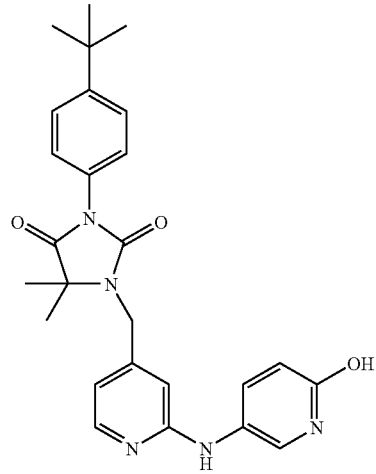

To a solution of 0.5 g of 3-(4-tert-butylphenyl)-1-[(2-chloropyridin-4-yl)methyl]-5,5-dimethylimidazolidine-2,4-dione obtained in stage a) of Example 7 in 15 mL of dioxane are successively added, under argon, 285 mg of 5-amino-2-hydroxypyridine, 1.6 g of caesium carbonate, 90 mg of (9,9-dimethyl-9H-xanthene-3,6-diyl)bis(diphenylphosphine) [xantphos] and 29 mg of palladium diacetate. The reaction mixture is heated at 100° C. for 1 hour, filtered and concentrated under reduced pressure. The residue is successively purified by chromatography on a column of silica, eluting with a mixture of dichloromethane and methanol (95/5 by volume) followed by HPLC (gradient: water/acetonitrile containing 0.1% formic acid) to give 35 mg of 3-(4-tert-butylphenyl)-1-({2-[(6-hydroxypyridin-3-yl)amino]pyridin-4-yl}methyl)-5,5-dimethylimidazolidine-2,4-dione, the characteristics of which are as follows:

1H NMR spectrum at 400 MHz: 1.32 (s, 9H); 1.42 (s, 6H); 4.58 (s, 2H); 6.41 (d, J=9.5 Hz, 1H); 6.80 (m, 2H); 7.35 (d, J=8.5 Hz, 2H); 7.48 (broad d, J=9.5 Hz, 1H); 7.52 (d, J=8.5 Hz, 2H); 7.78 (broad s, 1H); 7.98 (d, J=5.5 Hz, 1H); 9.07 (broad m, 1H).

Mass Spectrum (ES): m/z=460 [M+H]$^+$
m/z=458 [M−H]$^−$

EXAMPLE 31N

3-[4-(2-hydroxy-1,1-dimethylethyl)phenyl]-5,5-dimethyl-1-{[2-(pyridin-3-ylamino)pyridin-4-yl]methyl}-imidazolidine-2,4-dione

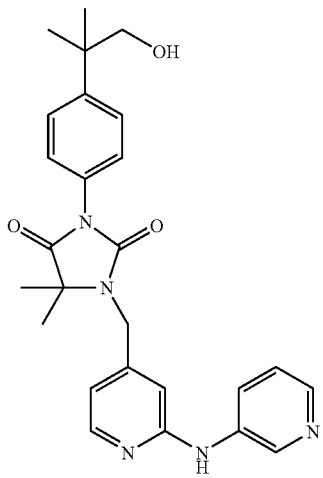

Stage g): 3-[4-(2-hydroxy-1,1-dimethylethyl)phenyl]-5,5-dimethyl-1-{[2-(pyridin-3-ylamino)pyridin-4-yl]-methyl}imidazolidine-2,4-dione To a solution of 0.29 mL of diborane-dimethyl sulphide (2M in tetrahydrofuran) in 5 mL of tetrahydrofuran, under argon, at room temperature, is added 0.11 g of 2-(4-{4,4-dimethyl-2,5-dioxo-3-[2-(pyridin-3-ylamino)pyridin-4-ylmethyl]imidazolidin-1-yl}-phenyl)-2-methylpropionic acid obtained in stage f) below. The reaction medium is stirred at this same temperature for one hour and concentrated under reduced pressure. The residue obtained is taken up in 10 mL of methanol and 2 mL of 1N hydrochloric acid. The solution is concentrated under reduced pressure. The residue obtained is purified by Preparative LC/MS (gradient: acetonitrile/water/TFA 0.07%). The product obtained is taken up in 10 mL of ethyl acetate, 2 mL of water and 1 mL of 1N sodium hydroxide. The organic phase is dried over magnesium sulphate, filtered and then concentrated under reduced pressure to give 0.048 g of 3-[4-(2-hydroxy-1,1-dimethylethyl)phenyl]-5,5-dimethyl-1-{[2-(pyridin-3-ylamino)-pyridin-4-yl]methyl}imidazolidine-2,4-dione, the characteristics of which are as follows:

1H NMR spectrum at 400 MHz: 1.25 (s, 6H); 1.42 (s, 6H); 3.45 (d, J=5.5 Hz, 2H); 4.55 (s, 2H); 4.71 (t, J=5.5 Hz, 1H); 6.82 (broad d, J=5.5 Hz, 1H); 6.84 (broad s, 1H); 7.27 (dd, J=5.0 and 8.5 Hz, 1H); 7.34 (d, J=8.5 Hz, 2H); 7.50 (d, J=8.5 Hz, 2H); 8.08 (dd, J=1.5 and 5.0 Hz, 1H); 8.12 (d, J=5.5 Hz, 1H); 8.21 (ddd, J=1.5-2.5 and 8.5 Hz, 1H); 8.79 (d, J=2.5 Hz, 1H); 9.21 (s, 1H).

Mass Spectrum (ES): m/z=460 [M+H]$^+$ base peak

Stage f): 2-[4-(4,4-dimethyl-2,5-dioxo-3-{[2-(pyridin-3-ylamino)pyridin-4-yl]methyl}imidazolidin-1-yl)phenyl]-2-methylpropanoic acid

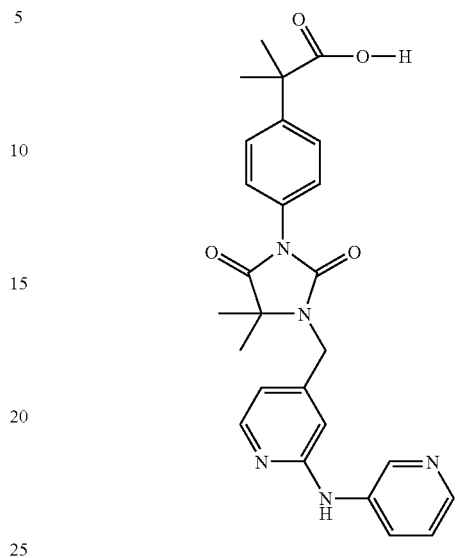

To a solution of 0.34 g of methyl 2-[4-(4,4-dimethyl-2,5-dioxo-3-{[2-(pyridin-3-ylamino)pyridin-4-yl]methyl}imidazolidin-1-yl)phenyl]-2-methylpropanoate obtained in stage e) below in 20 mL of methanol, at room temperature, are added 7 mL of 1N potassium hydroxide. The reaction medium is heated at reflux for two hours and concentrated under reduced pressure. The residue obtained is taken up in 10 mL of water and then acidified with 2N HCl to pH=5. The white solid formed is filtered off and then dried to give 0.225 g of 2-[4-(4,4-dimethyl-2,5-dioxo-3-{[2-(pyridin-3-ylamino)pyridin-4-yl]methyl}imidazolidin-1-yl)phenyl]-2-methylpropanoic acid, the characteristics of which are as follows:

1H NMR spectrum at 400 MHz: 1.41 (s, 6H); 1.50 (s, 6H); 4.55 (s, 2H); 6.83 (m, 2H); 7.27 (dd, J=5.0 and 8.5 Hz, 1H); 7.40 (d, J=8.5 Hz, 2H); 7.48 (d, J=8.5 Hz, 2H); 8.08 (broad d, J=5.0 Hz, 1H); 8.12 (d, J=5.5 Hz, 1H); 8.21 (broad d, J=8.5 Hz, 1H); 8.78 (d, J=2.5 Hz, 1H); 9.20 (s, 1H); 12.4 (broad m, 1H).

Mass Spectrum (ES): m/z=474 [M+H]$^+$ base peak

Stage e): methyl 2-[4-(4,4-dimethyl-2,5-dioxo-3-{[2-(pyridin-3-ylamino)pyridin-4-yl]methyl}imidazolidin-1-yl)phenyl]-2-methylpropanoate

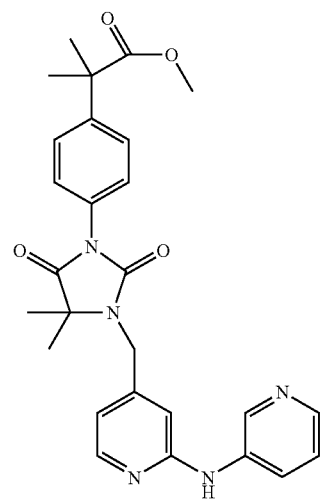

To a solution of 1.23 g of 2-{4-[3-(2-chloropyridin-4-ylmethyl)-4,4-dimethyl-2,5-dioxo-imidazolidin-1-yl]-phenyl}-2-methylpropionic acid methyl ester obtained in stage d) below in 40 mL of dioxane are successively added, under argon, 0.4 g of 3-aminopyridine, 0.16 g of (9,9-dimethyl-9H-xanthene-3,6-diyl)bis(diphenylphosphine) (Xantphos), 0.065 g of palladium acetate and 3.65 g of caesium carbonate. The reaction mixture is refluxed for 4 hours and then filtered and concentrated under reduced pressure. The residue is purified by chromatography on a column of silica, eluting with a mixture of dichloromethane and methanol (98/02 by volume) to give 0.96 g of methyl 2-[4-(4,4-dimethyl-2,5-dioxo-3-{[2-(pyridin-3-ylamino)pyridin-4-yl]methyl}imidazolidin-1-yl)phenyl]-2-methylpropanoate, the characteristics of which are as follows:

1H NMR spectrum at 400 MHz: 1.42 (s, 6H); 1.54 (s, 6H); 3.61 (s, 3H); 4.56 (s, 2H); 6.82 (broad d, J=5.5 Hz, 1H); 6.84 (broad s, 1H); 7.26 (dd, J=5.0 and 8.5 Hz, 1H); 7.41 (d, J=8.5 Hz, 2H); 7.45 (d, J=8.5 Hz, 2H); 8.08 (dd, J=1.5 and 5.0 Hz, 1H); 8.12 (d, J=5.5 Hz, 1H); 8.20 (ddd, J=1.5-2.5 and 8.5 Hz, 1H); 8.78 (d, J=2.5 Hz, 1H); 9.19 (s, 1H)

Mass Spectrum (ES): m/z=488 [M+H]$^+$ base peak

Stage d): 2-{4-[3-(2-Chloropyridin-4-ylmethyl)-4,4-dimethyl-2,5-dioxo-imidazolidin-1-yl]-phenyl}-2-methylpropionic acid methyl ester

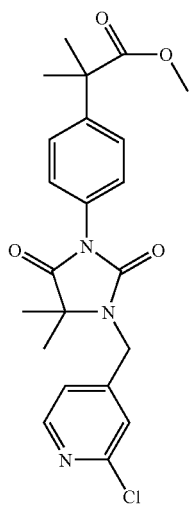

To a solution of 5 g of 2-[4-(4,4-dimethyl-2,5-dioxoimidazolidin-1-yl)phenyl]-2-methylpropionic acid methyl ester obtained in stage c) below in 30 mL of anhydrous dimethylformamide, under argon at room temperature, is added 0.19 g of 60% sodium hydride in oil. Stirring is continued at this temperature for 20 minutes, followed by addition of a solution of 0.63 g of 2-chloro-4-(chloromethyl)pyridine in 10 mL of anhydrous dimethylformamide. The reaction medium is heated at 60° C. for 5 hours and then poured onto ice and extracted with ethyl acetate. The organic phase is dried over magnesium sulphate, filtered and concentrated under vacuum. The residue is purified by chromatography on a column of silica, eluting with a mixture of dichloromethane and methanol (98/02 en volume) to give 1.23 g of 2-{4-[3-(2-Chloropyridin-4-ylmethyl)-4,4-dimethyl-2,5-dioxoimidazolidin-1-yl]phenyl}-2-methylpropionic acid methyl ester, the characteristics of which are as follows:

Mass Spectrum (ES): m/z=430 [M+H]$^+$ base peak

Stage c): methyl 2-[4-(4,4-dimethyl-2,5-dioxoimidazolidin-1-yl)phenyl]-2-methylpropanoate

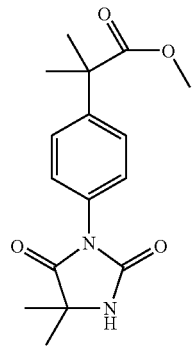

To a solution of 3.7 mL of trichloromethyl chloroformate (diphosgene) in 120 mL of toluene, under argon, is added 1 g of 3S charcoal. To this suspension cooled to −20° C. are added 4.3 g of methyl 2-(4-aminophenyl)-2-methylpropanoate obtained in stage b) below dissolved in 130 mL of toluene. The reaction mixture is gradually warmed to room temperature and then refluxed for 4 hours. After cooling to room temperature, 16.6 mL of triethylamine and 4.25 g of dimethylglycine methyl ester hydrochloride are added and the reaction mixture is refluxed for 24 hours and then concentrated under reduced pressure. The residue obtained is taken up in ethyl ether and water, the phases are separated and the organic phase is dried over magnesium sulphate, filtered and then concentrated under reduced pressure to give 1.23 g of methyl 2-[4-(4,4-dimethyl-2,5-dioxoimidazolidin-1-yl)phenyl]-2-methylpropanoate, the characteristics of which are as follows:

Mass Spectrum (ES): m/z=305 [M+H]$^+$ base peak

Stage b): methyl 2-(4-aminophenyl)-2-methylpropanoate

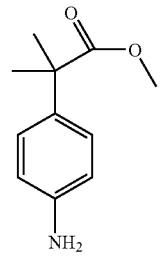

To a solution of 4.68 g of methyl 2-methyl-2-(4-nitrophenyl)-propanoate in 200 mL of ethanol, under argon, is added 0.5 g of palladium-on-charcoal (10%). The suspension is heated at 55° C. and 28 mL of hydrazine are added dropwise at this same temperature, and heating is continued for 3 hours at 55° C. After cooling, the reaction medium is filtered through Celite and the filtrate is concentrated under reduced pressure to give 4 g of 2-(4-aminophenyl)-2-methylpropionic acid methyl ester in the form of a colourless oil, the characteristics of which are as follows:

Mass Spectrum (ES): m/z=194 [M+H]$^+$ base peak

Stage a): methyl 2-methyl-2-(4-nitrophenyl)propanoate

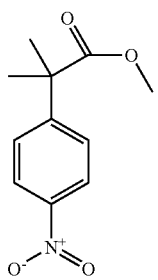

To a solution of 5 g of 2-(4-nitrophenyl)-2-methylpropionic acid in 40 mL of methanol, under argon, are added 4 mL of sulphuric acid. The reaction medium is heated at reflux for 3 hours and concentrated under reduced pressure. The residue is taken up in a mixture of ice-water and dichloromethane, the phases are separated and the organic phase is dried over magnesium sulphate and filtered. The filtrate is concentrated under reduced pressure to give 5.18 g of methyl 2-methyl-2-(4-nitrophenyl)propanoate in the form of a pale yellow solid, the characteristics of which are as follows:

Mass Spectrum (ES): m/z=224 $[M+H]^+$; m/z=194 $[M–NO+H]^+$ base peak

EXAMPLE 31O 1-(4-{[3-(4-tert-butylphenyl)-5,5-dimethyl-2,4-dioxoimidazolidin-1-yl]methyl}pyridin-2-yl)-3-pyridin-3-ylurea

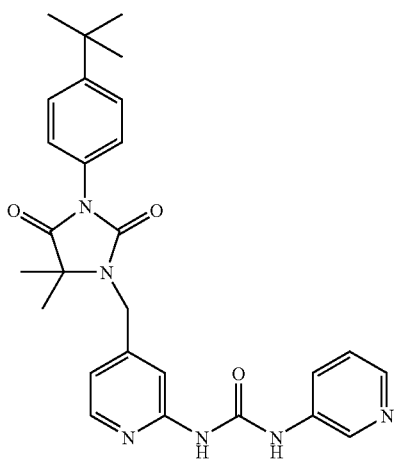

To a solution of 200 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 4 mL of dioxane are added 53 mg of 3-aminopyridine. The reaction mixture is heated by microwave at 130° C. for 20 minutes and concentrated under reduced pressure. The residue is purified by chromatography on a column of silica, eluting with a mixture of dichloromethane and methanol (98/2 by volume) to give 129 mg of 1-(4-{[3-(4-tert-butylphenyl)-5,5-dimethyl-2,4-dioxoimidazolidin-1-yl]methyl}pyridin-2-yl)-3-pyridin-3-ylurea, the characteristics of which are as follows:

1H NMR spectrum at 400 MHz: 1.31 (s, 9H); 1.41 (s, 6H); 4.61 (s, 2H); 7.03 (dd, J=1.5 and 5.5 Hz, 1H); 7.33 (partially masked m, 1H); 7.36 (d, J=8.5 Hz, 2H); 7.52 (m, 3H); 8.03 (broad d, J=8.0 Hz, 1H); from 8.21 to 8.28 (m, 2H); 8.70 (d, J=2.5 Hz, 1H); 9.70 (broad s, 1H).

Mass Spectrum (ES): m/z=487 $[M+H]^+$; m/z=485 $[M–H]^-$

EXAMPLE 31P 1-(4-{[3-(4-tert-butylphenyl)-5,5-dimethyl-2,4-dioxoimidazolidin-1-yl]methyl}pyridin-2-yl)urea

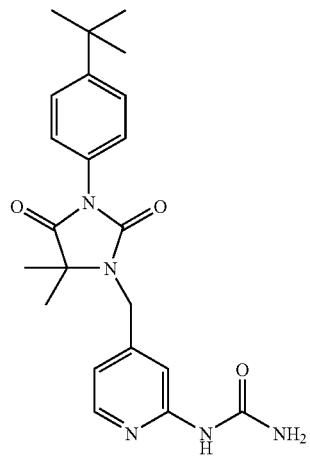

To a solution of 250 mg of 3-(4-tert-butylphenyl)-5,5-dimethyl-1-[(2-thioxo-2H-[1,2,4]oxadiazolo[2,3-a]pyridin-7-yl)methyl]imidazolidine-2,4-dione obtained in stage b) of Example 9 in 5 mL of dioxane are added 6.5 mL of a 7N solution of ammonia in methanol. The reaction mixture is heated by microwave at 130° C. for 3 hours and concentrated under reduced pressure. The residue is purified by HPLC (gradient: water/acetonitrile containing 0.1% formic acid) to give 54 mg of 1-(4-{[3-(4-tert-butylphenyl)-5,5-dimethyl-2,4-dioxo-imidazolidin-1-yl]methyl}pyridin-2-yl)urea, the characteristics of which are as follows:

1H NMR spectrum at 300 MHz: 1.31 (s, 9H); 1.41 (s, 6H); 4.61 (broad s, 2H); 7.02 (broad d, J=5.5 Hz, 1H); 7.10 (very broad m, 2H); 7.34 (m, 3H); 7.52 (d, J=8.5 Hz, 2H); 8.16 (d, J=5.5 Hz, 1H); 9.46 (broad m, 1H).

Mass Spectrum (ES): m/z=410 $[M+H]^+$; m/z=408 $[M–H]^-$

EXAMPLE 31Q methyl (4-{[3-(4-tert-butylphenyl)-5,5-dimethyl-2,4-dioxoimidazolidin-1-yl]methyl}pyridin-2-yl)carbamate

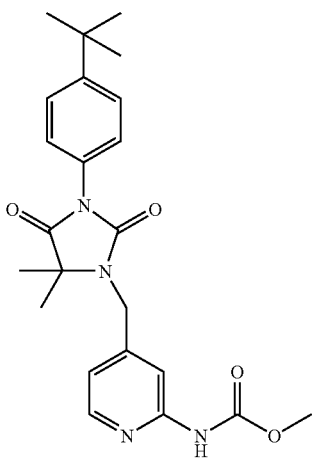

To a solution of 0.5 g of 3-(4-tert-butylphenyl)-1-[(2-chloropyridin-4-yl)methyl]-5,5-dimethylimidazolidine-2,4-dione obtained in stage a) of Example 7 in 15 mL of dioxane are successively added, under argon, 146 mg of methyl carbamate, 1.6 g of caesium carbonate, 75 mg of (9,9-dimethyl-9H-xanthene-3,6-diyl)bis(diphenylphosphine) [xantphos] and 29 mg of palladium diacetate. The reaction mixture is heated at 110° C. for 1 hour, filtered and concentrated under reduced pressure. The residue is purified by chromatography on a column of silica, eluting with a mixture of dichloromethane and ethyl acetate (80/20 by volume) to give 450 mg of methyl (4-{[3-(4-tert-butylphenyl)-5,5-dimethyl-2,4-dioxoimidazolidin-1-yl]methyl}pyridin-2-yl)carbamate, the characteristics of which are as follows:

1H NMR spectrum at 400 MHz: 1.31 (s, 9H); 1.40 (s, 6H); 3.68 (s, 3H); 4.61 (broad s, 2H); 7.07 (broad d, J=5.5 Hz, 1H); 7.33 (d, J=8.5 Hz, 2H); 7.51 (d, J=8.5 Hz, 2H); 7.87 (broad s, 1H); 8.21 (d, J=5.5 Hz, 1H); 10.15 (broad s, 1H).

Mass Spectrum (ES): m/z=425 [M+H]⁺; m/z=423 [M−H]⁻

EXAMPLE 31R 3-(4-tert-butylphenyl)-5,5-dimethyl-1-{[2-(pyridazin-4-ylamino)pyridin-4-yl]methyl}imidazolidine-2,4-dione

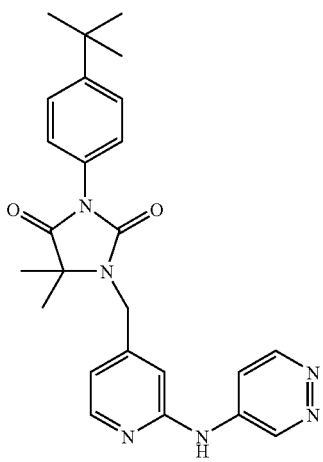

To a solution of 0.872 g of 3-(4-tert-butylphenyl)-1-[(2-chloropyridin-4-yl)methyl]-5,5-dimethylimidazolidine-2,4-dione obtained in stage a) of Example 7 in 25 mL of dioxane are successively added, under argon, 430 mg of 4-aminopyridazine, 2.8 g of caesium carbonate, 156 mg of (9,9-dimethyl-9H-xanthene-3,6-diyl)bis(diphenylphosphine) [xantphos] and 50 mg of palladium diacetate. The reaction mixture is heated at 90° C. for 6 hours, filtered and concentrated under reduced pressure. The residue is purified by chromatography on a column of silica, eluting with a mixture of dichloromethane and methanol (98/2 by volume) to give 55 mg of 3-(4-tert-butylphenyl)-5,5-dimethyl-1-{[2-(pyridazin-4-ylamino)pyridin-4-yl]-methyl}imidazolidine-2,4-dione, the characteristics of which are as follows:

1H NMR spectrum at 400 MHz: 1.32 (s, 9H); 1.42 (s, 6H); 4.60 (s, 2H); 6.98 (broad s, 1H); 7.01 (broad d, J=5.5 Hz, 1H); 7.36 (d, J=8.5 Hz, 2H); 7.53 (d, J=8.5 Hz, 2H); 8.13 (dd, J=3.0 and 6.5 Hz, 1H); 8.29 (d, J=5.5 Hz, 1H); 8.83 (d, J=6.5 Hz, 1H); 9.26 (d, J=3.0 Hz, 1H); 9.81 (s, 1H).

Mass Spectrum (ES): m/z=443 [M−H]⁻; m/z=445 [M+H]⁺

EXAMPLE 40S 3-(4-tert-butylphenyl)-5,5-dimethyl-1-[(2-{[6-(pyrrolidin-1-ylmethyl)pyridin-3-yl]amino}pyridin-4-yl)methyl]imidazolidine-2,4-dione

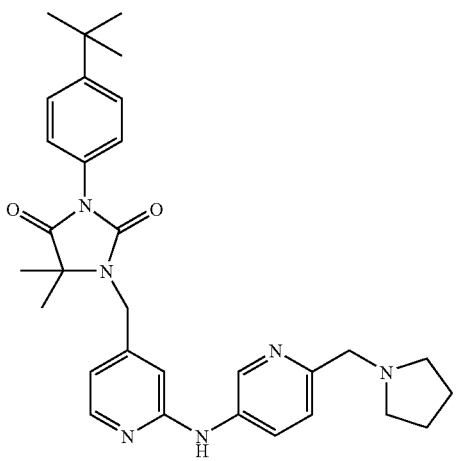

Stage b): 3-(4-tert-butylphenyl)-5,5-dimethyl-1-[(2-{[6-(pyrrolidin-1-ylmethyl)pyridin-3-yl]amino}pyridin-4-yl)-methyl]imidazolidine-2,4-dione To a solution of 0.5 g of 1-[(2-aminopyridin-4-yl)methyl]-3-(4-tert-butylphenyl)-5,5-dimethylimidazolidine-2,4-dione obtained in stage c) of Example 7 in 15 mL of dioxane are successively added, under argon, 0.32 g of 5-bromo-2-(pyrrolidin-1-ylmethyl)pyridine obtained in stage a) below, 77 mg of 9,9-dimethyl-4,5-bis(diphenylphosphino)xanthene (xantphos), 38 mg of palladium acetate and 1.75 g of caesium carbonate. The reaction mixture is refluxed for 7 hours and then filtered and concentrated under reduced pressure. The residue is purified by chromatography on a column of silica, eluting with a mixture of dichloromethane and methanol (87/13 by volume) to give 62 mg of 3-(4-tert-butylphenyl)-5,5-dimethyl-1-[(2-{[6-(pyrrolidin-1-yl-methyl)pyridin-3-yl]amino}pyridin-4-yl)methyl]imidazolidine-2,4-dione, the characteristics of which are as follows:

1H NMR spectrum at 400 MHz: 1.31 (s, 9H); 1.41 (s, 6H); 1.69 (m, 4H); 2.46 (m, 4H); 3.60 (s, 2H); 4.54 (broad s, 2H); 6.80 (broad d, J=5.5 Hz, 1H); 6.82 (broad s, 1H); 7.29 (d, J=8.5 Hz, 1H); 7.35 (d, J=8.5 Hz, 2H); 7.52 (d, J=8.5 Hz, 2H); 8.11 (d, J=5.5 Hz, 1H); 8.16 (dd, J=2.5 and 8.5 Hz, 1H); 8.65 (d, J=2.5 Hz, 1H); 9.14 (s, 1H).

Mass Spectrum (ES): m/z=527 [M+H]⁺
m/z=264 [M+2H]⁺⁺

Stage a): 5-bromo-2-(pyrrolidin-1-ylmethyl)pyridine

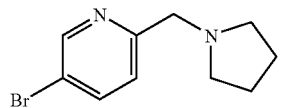

To a solution of 2 g of 5-bromo-2-formylpyridine in 20 mL of 1,2-dichloroethane are successively added, under argon, 4.55 g of sodium triacetoxyborohydride and 0.94 mL of pyrrolidine. The reaction mixture is stirred at room temperature for 1 hour and then diluted with dichloromethane and the organic phase is washed with saturated sodium hydrogen carbonate solution, with water and with saturated sodium chloride solution, dried over magnesium sulphate, filtered and concentrated under reduced pressure. The residue is purified by chromatography on a column of silica, eluting with a mixture of dichloromethane and methanol (98/2 by volume) to give 0.93 g of 5-bromo-2-pyrrolidin-1-ylmethylpyridine, the characteristics of which are as follows:

1H NMR spectrum at 400 MHz: 1.70 (m, 4H); 2.48 (m, 4H); 3.69 (s, 2H); 7.40 (d, J=8.5 Hz, 1H); 7.99 (dd, J=2.5 and 8.5 Hz, 1H); 8.59 (d, J=2.5 Hz, 1H).

Mass Spectrum LCMS: m/z=241: [M+H]+

EXAMPLE 40T 3-(4-tert-butylphenyl)-5,5-dimethyl-1-[2-(5-pyrrolidin-1-ylmethylpyridin-3-ylamino)pyridin-4-ylmethyl]-imidazolidine-2,4-dione

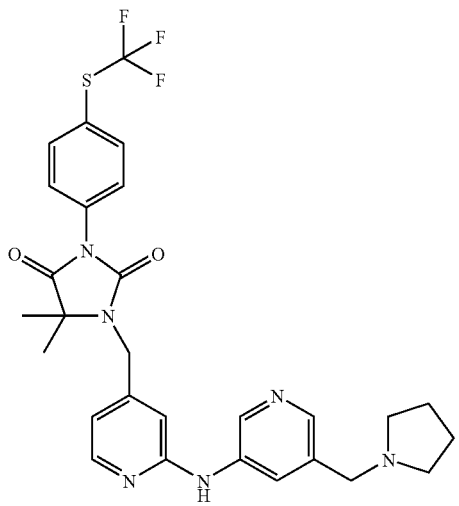

Stage b): 3-(4-tert-butylphenyl)-5,5-dimethyl-1-[2-(5-pyrrolidin-1-ylmethylpyridin-3-ylamino)pyridin-4-yl-methyl]imidazolidine-2,4-dione To a solution of 500 mg of 1-[(2-aminopyridin-4-yl)methyl]-3-(4-tert-butylphenyl)-5,5-dimethylimidazolidine-2,4-dione obtained in stage c) of Example 7 in 15 mL of dioxane are successively added, under argon, 46 mg of palladium diacetate, 95 mg of (9,9-dimethyl-9H-xanthene-3,6-diyl)bis(diphenylphosphine)(Xantphos), 1.8 g of caesium carbonate and 0.39 g of 3-Bromo-5-pyrrolidin-1-ylmethylpyridine obtained in stage a) below. The reaction mixture is refluxed for 4 hours and then filtered, and the filtrate is concentrated under reduced pressure. The residue is purified by chromatography on a column of silica, eluting with a mixture of dichloromethane and methanol (96/4 by volume) to give 90 mg of 3-(4-tert-butylphenyl)-5,5-dimethyl-1-[2-(5-pyrrolidin-1-ylmethylpyridin-3-ylamino)pyridin-4-ylmethyl]imidazolidine-2,4-dione, the characteristics of which are as follows:

1H NMR spectrum at 400 MHz: 1.31 (s, 9H); 1.42 (s, 6H); 1.70 (m, 4H); 2.43 (m, 4H); 3.54 (s, 2H); 4.54 (s, 2H); 6.81 (m, 2H); 7.35 (d, J=8.5 Hz, 2H); 7.52 (d, J=8.5 Hz, 2H); 8.00 (d, J=2.0 Hz, 1H); 8.07 (d, J=2.0 Hz, 1H); 8.14 (d, J=5.5 Hz, 1H); 8.73 (d, J=2.0 Hz, 1H); 9.18 (s, 1H).

Mass Spectrum (ES): m/z=527 [M+H]+; m/z=525 [M−H]−

Stage a): 3-Bromo-5-pyrrolidin-1-ylmethylpyridine

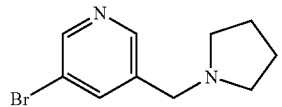

To a solution of 5-bromo-3-pyridinecarboxaldehyde in 20 mL of 1,2-dichloroethane are successively added, under argon, 4.55 g of sodium triacetoxyborohydride and 0.94 mL of pyrrolidine. The reaction mixture is stirred at room temperature for 3 hours and then washed with saturated sodium hydrogen carbonate solution, with water and with saturated sodium chloride solution, dried over magnesium sulphate, filtered and concentrated under reduced pressure. The residue is purified by chromatography on a column of silica, eluting with a mixture of ethyl acetate and cyclohexane (80/20 by volume) to give 1.4 g of 3-Bromo-5-pyrrolidin-1-ylmethylpyridine in the form of a pale yellow oil.

Mass Spectrum (ES): m/z=241 [M+H]+; m/z=161 [M+H]+−Br (base peak)

EXAMPLE 31U 3-(4-tert-butylphenyl)-5,5-dimethyl-1-[(2-{[4-(2-pyrrolidin-1-ylethyl)phenyl]amino}pyridin-4-yl)-methyl]imidazolidine-2,4-dione

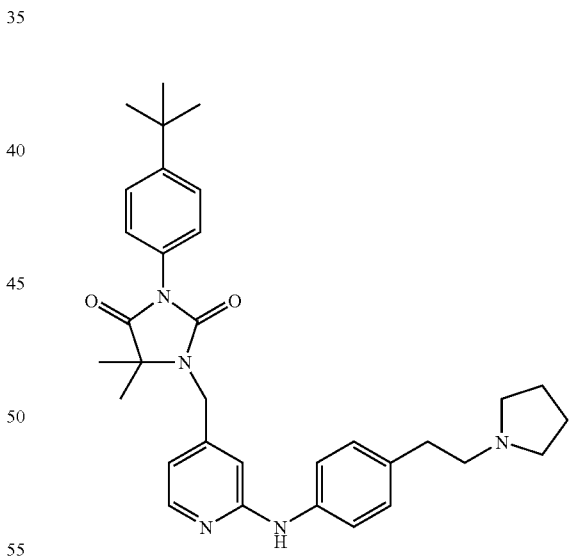

Stage d: 3-(4-tert-butylphenyl)-5,5-dimethyl-1-[(2-{[4-(2-pyrrolidin-1-ylethyl)phenyl]amino}pyridin-4-yl)methyl]-imidazolidine-2,4-dione To a solution of 1.16 g of 3-(4-tert-butylphenyl)-1-[(2-chloropyridin-4-yl)methyl]-5,5-dimethylimidazolidine-2,4-dione obtained in stage a) of Example 7 in 50 mL of dioxane are successively added, under argon, 570 mg of 43-(2-pyrrolidin-1-ylethyl)aniline obtained in stage c) below, 3.34 g of caesium carbonate, 210 mg of (9,9-dimethyl-9H-xanthene-3, 6-diyl)bis(diphenylphosphine) [xantphos] and 67 mg of palladium diacetate. The reaction mixture is heated at 90° C. for 5 hours, filtered and concentrated under reduced pressure. The residue is purified by chromatography on a column of silica, eluting with a mixture of dichloromethane and methanol (95/5 by volume) to give 99 mg of 3-(4-tert-butylphenyl)-5,5-dimethyl-1-[(2-{[4-(2-pyrrolidin-1-ylethyl)phenyl]amino}pyridin-4-yl)methyl]imidazolidine-2,4-dione, the characteristics of which are as follows:

1H NMR spectrum at 400 MHz: 1.31 (s, 9H); 1.41 (s, 6H); 1.68 (m, 4H); 2.46 (m, 4H); from 2.55 to 2.71 (m, 4H); 4.52 (s, 2H); 6.74 (d, J=5.5 Hz, 1H); 6.80 (s, 1H); 7.09 (d, J=8.5 Hz, 2H); 7.33 (d, J=8.5 Hz, 2H); 7.50 (m, 4H); 8.10 (d, J=5.5 Hz, 1H); 8.90 (s, 1H).

Mass Spectrum (ES): m/z=540 [M+H]⁺

Stage c: 4-(2-pyrrolidin-1-ylethyl)aniline

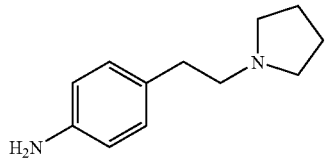

To a solution of 1.22 g of 4-(2-oxo-2-pyrrolidin-1-ylethyl)aniline obtained in stage b) below in 100 mL of tetrahydrofuran are added, under argon, 1.1 g of lithium aluminium hydride. The reaction mixture is stirred for one hour at room temperature and then cooled to 0° C. and treated successively with 1.1 mL of water, 1.1 mL of 15% (by weight) sodium hydroxide solution and 3.4 mL of water. The solid formed is filtered off and washed with ethyl acetate, and the filtrate is concentrated under reduced pressure to give 1.15 g of 4-(2-pyrrolidin-1-ylethyl)aniline, the characteristics of which are as follows:

Mass Spectrum (ES): m/z=191 [M+H]⁺

Stage b: 3-(2-oxo-2-pyrrolidin-1-ylethyl)aniline

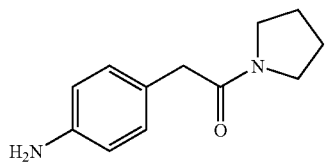

To a solution of 0.8 g of 1-[(4-nitrophenyl)acetyl]pyrrolidine obtained in stage a) below in 20 mL of methanol are added, under argon, 1.72 g of ammonium formate and 36 mg of 10% palladium-on-charcoal. The reaction mixture is stirred at room temperature for 1 hour and then filtered through Celite and concentrated under reduced pressure. The residue is taken up in water and extracted with dichloromethane. The organic phase is then washed with water and with saturated sodium chloride solution, dried over magnesium sulphate, filtered and concentrated under reduced pressure to give 0.49 g of 4-(2-oxo-2-pyrrolidin-1-ylethyl)aniline, the characteristics of which are as follows:

Mass Spectrum (ES): m/z=205 [M+H]⁺

Stage a: 1-[(4-nitrophenyl)acetyl]pyrrolidine

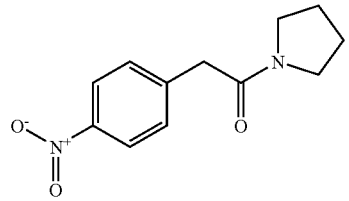

To a solution of 3 g of para-nitrobenzoic acid in 50 mL of dichloromethane are successively added under argon, at 0° C., 1.15 mL of pyrrolidine, 0.189 g of hydroxybenzotriazole, 2.3 g of 1,3-dimethylaminopropyl-3-ethylcarbodiimide and 4.98 mL of diisopropylamine. The reaction mixture is then stirred at room temperature for 15 hours and then washed with water. The organic phase is then washed with saturated sodium chloride solution, dried over magnesium sulphate, filtered and concentrated under reduced pressure. The residue is purified by chromatography on a column of silica, eluting with a mixture of ethyl acetate and cyclohexane (55/45 by volume) to give 2.98 g of 1-[(4-nitrophenyl)acetyl]pyrrolidine, the characteristics of which are as follows:

Mass Spectrum (ES): m/z=235 [M+H]⁺

In Vitro Biological Tests

A) Experimental Protocol for the Kinase IGF-1R Test:

The inhibitory activity of the compounds on IGF1R is determined by measuring the inhibition of autophosphorylation of the enzyme using a time-resolved fluorescence test (HTRF). The human cytoplasmic domain of IGF-1R was cloned by fusion with glutathione S-transferase (GST) in the baculovirus expression vector pFastBac-GST. The protein is expressed in the SF21 cells and purified to about 80% homogeneity. For the enzymatic test, the test compound at 10 mM dissolved in DMSO is diluted in 1/3 steps in a 50 mM Hepes, pH 7.5, 5 mM MnCl₂, 50 mM NaCl, 3% Glycerol, 0.025% Tween 20 buffer. To measure the inhibition, the successive dilutions of the compound are preincubated for 30 minutes and 90 minutes in the presence of 5 nM of enzyme, the final DMSO concentration not exceeding 1%. The enzymatic reaction is initiated to have a final ATP concentration of 120 μM, and is stopped after 5 minutes by addition of 100 mM Hepes, pH 7.0 buffer containing 0.4 M of potassium fluoride, 133 mM EDTA, 0.1% BSA, the XL665-labelled antibody anti-GST and the anti-phosphotyrosine antibody conjugated to europium cryptate Eu—K (Cis-Bio Int.). The characteristics of the two fluorophores, XL-665 and Eu—K, are available in G. Mathis et al., Anticancer Research, 1997, 17, pages 3011-3014. The energy transfer between the excited europium cryptate to the acceptor XL665 is proportional to the degree of autophosphorylation of IGF-1R. The specific long-lasting signal of XL-665 is measured in a GENios Pro TECAN plate counter. The inhibition of autophosphorylation of IGF-1R at time 30 minutes and 90 minutes with the test compounds of the invention is calculated relative to a 1% in DMSO control, whose activity is measured in the absence of compound. The curve representing the percentage of inhibition as a function of the log of the concentration is established to determine the concentration corresponding to 50% inhibition (IC₅₀).

B) Measurement of the Autophosphorylation of IGF-1r in MCF7 Cells after Stimulation with IGF-1

Cell Culturing and Execution of the Test:

The autophosphorylation of IGF1R in the IGF1-induced cells is evaluated by means of an ELISA technique (Enzyme Linked ImmunoSorbent Assay). The MCF-7 are seeded at 60 000 cells per well in 6-well plates and incubated at 37° C., 5% $CO_2$ in medium containing 10% serum. After one night in 10% serum, the cells are deprived of serum for 24 hours. The compounds are added to the medium one hour before stimulation with IGF1. After 10 minutes of stimulation with IGF1, the cells are lysed with a buffer (Hepes 50 mM pH 7.6, Triton X100 1%, orthovanadate 2 mM, protease inhibitor cocktail). The cell lysates are incubated on a 96-well plate precoated with an anti-IGF1R antibody, followed by incubation with an anti-phosphotyrosine antibody coupled to the enzyme peroxidase. The level of peroxidase activity (measured by OD with a luminescent substrate) reflects the phosphorylation status of the receptor.

Calculating the Results:
(i) The tests are performed in duplicate and the mean of the two tests is calculated.
(ii) The value of the signal of the maximum response is calculated from the positive control: cells stimulated with IGF1 without compound.
(iii) Value of the signal of the minimum response is calculated from the negative control: cells not stimulated with IGF1 without compound.
(iv) By using these values as maximum (100%) and minimum (0%), respectively, the data were normalized so as to give a percentage of the maximum response.
(v) A curve of dose response is plotted and the $IC_{50}$ (the concentration of which the compound induces a 50% decrease in the signal) of the compound is calculated by non-linear regression analysis.

C) Measurement of the Proliferation/Viability of MEF-IGF1R

Cell culture: the MEF-IGF1R cells (stable clone of cells transfected with the receptor hIGF-1R) are cultured at 37° C. under 5% CO2 in EMEM medium containing 10% FCS.

Test procedure: the cells are seeded at 5000 cells per well in 96-well Cytostar plates (Amersham) with 0.2 mL of EMEM culture medium at 37° C. for 18 hours. The cells are then washed twice with EMEM medium and left to culture without serum for 24 hours. The compounds are then added at various concentrations in the presence of rhIGF1 (100 ng/mL) and 0.1 µCi of Thymidine [$^{14}C$] (specific activity ~50 mCi/mmol) to give 0.2 mL of volume per well. After incubation for 72 hours in the presence of the compound, at 37° C. under 5% $CO_2$, the incorporation of Thymidine [$^{14}C$] is measured by counting the radioactivity on a Microbeta trilux counter (Perkin-Elmer). The $IC_{50}$ is determined from 10 increasing concentrations of the compound.

Calculating the Results:
(i) The tests are performed in duplicate and the mean of the two tests is calculated.
(ii) The value of the signal of the maximum response is calculated from the positive control: cells stimulated with IGF1 without compound.
(iii) Value of the signal of the minimum response is calculated from the negative control: cells not stimulated with IGF1 without compound.
(iv) By using these values as maximum (100%) and minimum (0%), respectively, the data were normalized so as to give a percentage of the maximum response.
(v) A curve of dose response is plotted and the $IC_{50}$ (the concentration of which the compound induces a 50% decrease in the signal) of the compound is calculated by non-linear regression analysis.

The table below gives the activities of certain examples of the present invention in the three tests A, B and C described above:

| Examples | Test A* 30' | Test A* 90' | Test B* | Test C* |
|---|---|---|---|---|
| Example 1 | ++ | +++ | +++ | +++ |
| Example 1 Stage f) | ++ | ++ | | + |
| Example 2 | + | + | | + |
| Example 3 | + | ++ | | ++ |
| Example 4 | ++ | ++ | | +++ |
| Example 5a | ++ | ++ | | +++ |
| Example 6a | + | ++ | | +++ |
| Example 7 | ++ | ++ | | + |
| Example 8 | ++ | +++ | +++ | +++ |
| Example 9 | ++ | ++ | | + |
| Example 10 | ++ | ++ | | + |
| Example 11 | ++ | ++ | | + |
| Example 12 | ++ | +++ | | + |
| Example 13 | ++ | ++ | ++ | ++ |
| Example 14 | ++ | ++ | ++ | ++ |
| Example 16 | + | ++ | | + |
| Example 18 | ++ | ++ | +++ | ++ |
| Example 19 | ++ | ++ | +++ | ++ |
| Example 20 | ++ | +++ | | + |
| Example 27 | ++ | ++ | | + |
| Example 28 | ++ | ++ | ++ | + |
| Example 31A | ++ | ++ | | + |
| Example 31B | + | ++ | ++ | +++ |
| Example 31C | + | + | ++ | ++ |
| Example 31D | + | ++ | ++ | ++ |
| Example 31E | + | + | ++ | ++ |
| Example 31F | ++ | +++ | ++ | +++ |
| Example 31G | ++ | +++ | ++ | +++ |
| Example 31H | ++ | +++ | +++ | +++ |
| Example 31I | + | ++ | ++ | +++ |
| Example 31J | ++ | +++ | ++ | ++ |
| Example 31K | ++ | ++ | +++ | ++ |
| Example 31L | + | ++ | ++ | ++ |
| Example 31M | ++ | ++ | ++ | ++ |
| Example 31N | + | ++ | ++ | + |
| Example 31O | + | + | ++ | ++ |
| Example 31P | ++ | +++ | ++ | +++ |
| Example 31Q | ++ | +++ | +++ | ++ |
| Example 31U | ++ | +++ | +++ | +++ |

*For tests A, B and C, the $IC_{50}$ (nM) are distributed as follows:
+ >100 nM
10 nM < ++ < 100 nM
+++ <10 nM The products of formula (Ia) as defined above, in which the radical NR4R5 has the values indicated above numbered as ex 9 to ex 31, correspond, respectively, to Examples 9 to 31 of the present in: the products of Examples 9 to 31 are prepared as indicated in the general synthetic schemes described above.

A general method for preparing ureas (such as, especially, for the preparation of the products of Examples 9 to 31) is as follows: 0.3 mmol of ethyl {4-[3-(4-tert-butylphenyl)-5,5-dimethyl-2,4-dioxo-imidazolidin-1-ylmethyl]pyridin-2-yl}carbamate and 3 mmol of the appropriate amine are mixed together and heated in 3 mL of N-methylpyrrolidinone for 2 hours by microwave at 130° C. to fast give the expected corresponding urea.

Ethyl {4-[3-(4-tert-butylphenyl)-5,5-dimethyl-2,4-dioxo-imidazolidin-1-ylmethyl]pyridin-2-yl}carbamate may be prepared from 3-(4-tert-butylphenyl)-1-(2-chloropyridin-4-ylmethyl)-5,5-dimethyl-imidazolidine-2,4-dione and ethyl carbamate by coupling with palladium as described in the General Schemes above.

3-(4-tert-Butylphenyl)-1-(2-chloropyridin-4-ylmethyl)-5,5-dimethyl-imidazolidine-2,4-dione may be prepared as indicated in the General Schemes above.

EXAMPLE 32

Pharmaceutical Composition

Tablet corresponding to the following formula were prepared:

| Products of Example 1 | 0.2 g |
|---|---|
| Excipient for a finished tablet weighing | 1 g |

(details of the excipient: lactose, talc, starch, magnesium stearate).

EXAMPLE 33

Pharmaceutical Composition

Tablets corresponding to the following formula were prepared:

| Product of Example 8 | 0.2 g |
|---|---|
| Excipient for a finished tablet weighing | 1 g |

(details of the excipient: lactose, talc, starch, magnesium stearate).

What is claimed is:

1. A compound of formula (I):

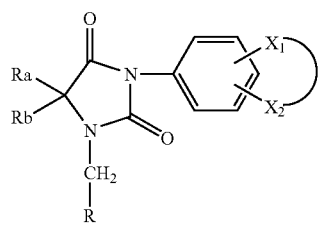

in which:
Ra and Rb represent CH3 or form, together with the carbon atom to which they are attached, a cycloalkyl radical,
X1 and X2 are such that:
either one represents hydrogen and the other represents alkyl, or one represents —OCF3 or —SCF3 and the other represents the radical NH—CO—R6,
or X1 and X2 form, with the phenyl radical to which they are attached, a dihydroindole radical optionally substituted with one or more alkyl radicals and on its nitrogen atom with a radical CO-alkyl-R3,
R represents a pyridyl or pyrimidinyl radical substituted with a radical NR1R2,
NR1R2 being such that:
one from among R1 and R2 represents a hydrogen atom or an alkyl radical, and the other from among R1 and R2 is chosen from a hydrogen atom and alkyl radicals optionally substituted with a radical chosen from hydroxyl, alkoxy, aziridyl, azetidinyl, pyrrolidinyl, piperidyl, morpholinyl, and piperazinyl, which is itself optionally substituted on its second nitrogen atom with an alkyl radical; optionally substituted cycloalkyl, heterocycloalkyl, aryl and heteroaryl radicals; and the radical CO—R3 with R3 chosen from NR4R5 and optionally substituted alkoxy, heterocycloalkyl, aryl, aryloxy and heteroaryl radicals;
R4 and R5, which may be identical to or different from R1 and R2, are such that:
either one from among R4 and R5 represents a hydrogen atom or an alkyl radical, and the other from among R4 and R5 is chosen from a hydrogen atom and alkyl radicals optionally substituted with a radical chosen from hydroxyl, alkoxy, aziridyl, azetidinyl, pyrrolidinyl, piperidyl, morpholinyl, and piperazinyl, which is itself optionally substituted on its second nitrogen atom with an alkyl radical; optionally substituted cycloalkyl, heterocycloalkyl, aryl and heteroaryl radicals;
or R4 and R5 form, with the nitrogen atom to which they are attached, a cyclic amine optionally containing another heteroatom chosen from N and O, which is optionally substituted,
all the above aryl, phenyl, aryloxy and heteroaryl radicals, and also the cyclic amine NR4R5, being optionally substituted with one to three radicals, which may be identical or different, chosen from halogen atoms and alkyl, phenyl, NH2, NHAlk, N(Alk)2, CO—NHAlk and CO—N(Alk)2 radicals;
R6 represents alkyl optionally substituted with one or more radicals, which may be identical or different, chosen from the values of R3,
or an addition salt with a mineral or organic acid or with a mineral or organic base of said compound of formula (I);
said compound being in any possible racemic, enantiomeric or diastereoisomeric isomer form.

2. A compound of formula (I) according to claim 1:

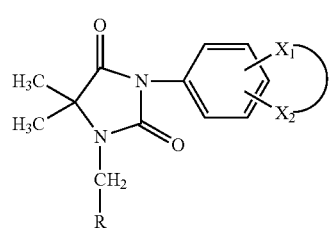

in which:
Ra and Rb represent CH3,
X1 and X2 are as defined in claim 1,
R represents a pyridyl or pyrimidinyl radical substituted with a radical NR1R2,
NR1R2 being such that:
one from among R1 and R2 represents a hydrogen atom or an alkyl radical, and the other from among R1 and R2 is chosen from a hydrogen atom and alkyl radicals optionally substituted with a radical chosen from hydroxyl, alkoxy, aziridyl, azetidinyl, pyrrolidinyl, piperidyl, morpholinyl, and piperazinyl, which is itself optionally substituted on its second nitrogen atom with an alkyl radical; optionally substituted cycloalkyl, heterocycloalkyl, phenyl, pyrimidinyl and pyridyl radicals; and the radical CO—R3 with R3 chosen from NR4R5 and optionally substituted alkoxy, piperidyl, phenyl and phenoxy radicals;
R4 and R5, which may be identical to or different from R1 and R2, are such that:
either one from among R4 and R5 represents a hydrogen atom or an alkyl radical, and the other from among R4 and R5 is chosen from a hydrogen atom and alkyl radicals optionally substituted with a radical chosen from hydroxyl, alkoxy, aziridyl, azetidinyl, pyrrolidinyl, piperidyl, morpholinyl, and piperazinyl, which is itself optionally substituted on its second nitrogen atom with an alkyl radical; optionally substituted cycloalkyl, heterocycloalkyl, phenyl, pyrimidinyl and pyridyl radicals;

or R4 and R5 form, with the nitrogen atom to which they are attached, a cyclic amine optionally containing another heteroatom chosen from N and O, which is optionally substituted, all the above phenyl, pyrimidinyl and pyridyl radicals being optionally substituted with one to three radicals, which may be identical or different, chosen from halogen atoms and alkyl, phenyl, NH2, NHAlk, N(Alk)2, CO—NHAlk and CO—N(Alk)2 radicals;

or an addition salt with a mineral or organic acid or with a mineral or organic base of said compound of formula (I);

said compound being in any possible racemic, enantiomeric or diastereoisomeric isomer form.

3. A compound of formula (I) according to claim 1 in which:

X1 and X2 are such that:

either one represents hydrogen and the other represents an alkyl radical, or one represents —OCF3 or —SCF3 and the other represents the radical NH—CO—R6, or X1 and X2 form, with the phenyl radical to which they are attached, a dihydroindole radical optionally substituted with one or more alkyl radicals and on its nitrogen atom with a radical CO—CH2-NH-cycloalkyl, R represents a pyridyl or pyrimidinyl radical substituted with a radical NR1R2, NR1R2 being such that R1 represents a hydrogen atom or an alkyl radical, and R2 is chosen from a hydrogen atom and alkyl radicals optionally substituted with a hydroxyl, aziridyl, azetidinyl, pyrrolidinyl, piperidyl, morpholinyl, or piperazinyl, which is itself optionally substituted on its second nitrogen atom with an alkyl radical; 3- to 6-membered cycloalkyl radicals; an optionally substituted phenyl radical;

a pyrimidinyl radical; a pyridyl radical optionally substituted with a halogen atom; and the radical C0-R3 with R3 chosen from NR4R5 and optionally substituted alkoxy, piperidyl and phenyl radicals;

R4 and R5, which may be identical to or different from R1 and R2, are such that:

either one from among R4 and R5 represents a hydrogen atom or an alkyl radical, and the other from among R4 and R5 is chosen from a hydrogen atom and alkyl radicals optionally substituted with a hydroxyl, aziridyl, azetidinyl, pyrrolidinyl, piperidyl, morpholinyl, or piperazinyl, which is itself optionally substituted on its second nitrogen atom with an alkyl radical; 3- to 6-membered cycloalkyl radicals; an optionally substituted phenyl radical; a pyrimidinyl radical; a pyridyl radical optionally substituted with a halogen atom;

or R4 and R5 form, with the nitrogen atom to which they are attached, an aziridyl, azetidinyl, pyrrolidinyl, piperidyl, morpholinyl, or piperazinyl, which is itself optionally substituted on its second nitrogen atom with an alkyl radical, all the phenyl radicals being optionally substituted with one to three radicals, which may be identical or different, chosen from halogen atoms, alkyl radicals and radicals CO—NHAlk and CO—N(Alk)2;

with R6 representing alkyl optionally substituted with one or more radicals, which may be identical or different, chosen from the values of R3;

or an addition salt with a mineral or organic acid or with a mineral or organic base of said compound of formula (I);

said compound being in any possible racemic, enantiomeric or diastereoisomeric isomer form.

4. A compound of formula (I) according to claim 1 in which: X1 and X2 are such that:

either one represents hydrogen and the other represents a tert-butyl radical, or one represents —OCF3 or —SCF3 and the other represents the radical —NH—CO—CH(NH2)-phenyl, or X1 and X2 form, with the phenyl radical to which they are attached, a dihydroindole radical substituted with two methyl radicals and on its nitrogen atom with a radical CO—CH2-NH-cyclopentyl, R represents a pyridyl or pyrimidinyl radical substituted with a radical NR1R2, NR1R2 being such that R1 represents a hydrogen atom or an alkyl radical containing one or two carbon atoms, and R2 is chosen from alkyl radicals containing 1 to 4 carbon atoms optionally substituted with a hydroxyl radical; an optionally substituted phenyl radical; a pyrimidinyl radical; a pyridyl radical optionally substituted with a halogen atom; and the radical CO—R3 with R3 chosen from piperidyl, optionally substituted phenyl, NH-cycloalkyl, NH2, NH(alk) and N(alk)2; all the phenyl radicals being optionally substituted with one to three radicals, which may be identical or different, chosen from halogen atoms and alkyl radicals and radicals CO—NHAlk and CO—N(Alk)2;

or an addition salt with a mineral or organic acid or with a mineral or organic base of said compound of formula (I);

said compound being in any possible racemic, enantiomeric or diastereoisomeric isomer form.

5. A compound of formula (I) according to claim 1 in which:

X1 and X2 are as defined in claim 1;

R represents a pyridyl or pyrimidinyl radical substituted with a radical NR1R2 in which R1 represents a hydrogen atom and R2 represents a pyrimidinyl or pyridyl radical; or a radical CO—N(CH3)2;

or an addition salt with a mineral or organic acid or with a mineral or organic base of said compound of formula (I);

said compound being in any possible racemic, enantiomeric or diastereoisomeric isomer form.

6. A compound of formula (I) according to claim 1 in which X1, X2, Ra, Rb and R are as defined in claim 1, and the radicals NR1R2 or NR4R5 or alternatively NR1R2 and NR4R5 are chosen from the following radicals named ex 9 to ex 31:

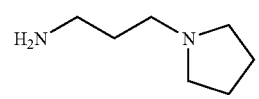

ex 9

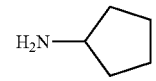

ex 10

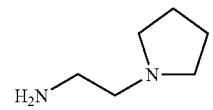

ex 11

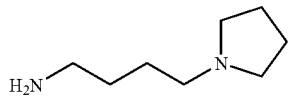

ex 12

| | |
|---|---|
| ex 13 | 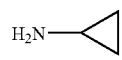 |
| ex 14 | 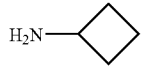 |
| ex 15 | 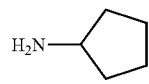 |
| ex 16 | 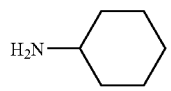 |
| ex 17 |  |
| ex 18 |  |
| ex 19 |  |
| ex 20 | 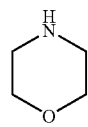 |
| ex 21 | 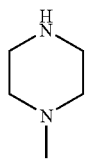 |
| ex 22 | 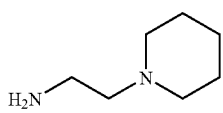 |
| ex 23 | 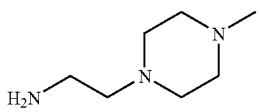 |
| ex 24 | 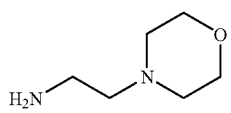 |
| ex 25 | 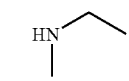 |
| ex 26 | 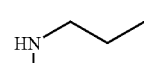 |
| ex 27 | 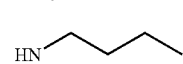 |
| ex 28 | 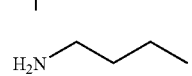 |
| ex 29 | 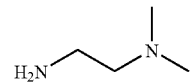 |
| ex 30 | 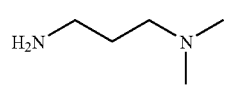 |
| ex 31 | 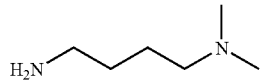 | or an addition salt with a mineral or organic acid or with a mineral or organic base of said compound of formula (I); said compound being in any possible racemic, enantiomeric or diastereoisomeric isomer form.

7. A compound according to claim 6 having the formula (Ia):

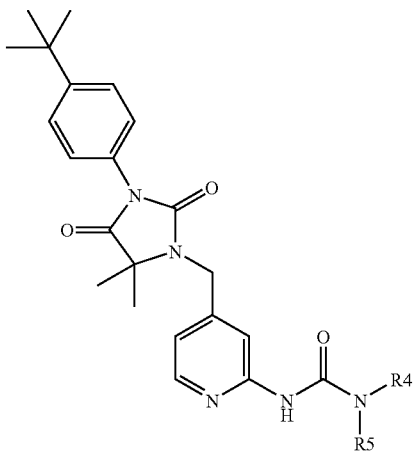

(Ia)

in which NR4R5 is as defined in claim 6, or an addition salt with a mineral or organic acid or with a mineral or organic base of said compound of formula (I); said compound being in any possible racemic, enantiomeric or diastereoisomeric isomer form.

8. A compound of formula (I) according to claim 1, selected from the group consisting of:

3-(4-tert-butylphenyl)-5,5-dimethyl-1-[2-(pyridin-3-yl-amino)pyrimidin-4-ylmethyl]imidazolidine-2,4-dione;

3-(4-{[3-(4-tert-butylphenyl)-5,5-dimethyl-2,4-dioxoimidazolidin-1-yl]methyl}pyrimidin-2-yl)-1,1-dimethylurea;

3-[4-({3-[1-(N-cyclopentylglycyl)-3,3-dimethyl-2,3-dihydro-1H-indol-6-yl]-5,5-dimethyl-2,4-dioxoimidazolidin-1-yl}methyl)pyridin-2-yl]-1,1-dimethylurea;

3-[1-(N-cyclopentylglycyl)-3,3-dimethyl-2,3-dihydro-1H-indol-6-yl]-5,5-dimethyl-1-{[2-(pyridin-3-ylamino)pyridin-4-yl]methyl}imidazolidine-2,4-dione;

(2R)-2-amino-N-[5-(4,4-dimethyl-2,5-dioxo-3-{[2-(pyridin-3-ylamino)pyrimidin-4-yl]methyl}imidazolidin-1-yl)-2-(trifluoromethoxy)phenyl]-2-phenylacetamide;

(2R)-2-amino-N-{5-(4,4-dimethyl-2,5-dioxo-3-{[2-(pyridin-3-ylamino)pyrimidin-4-yl]methyl}imidazolidin-1-yl)-2-[(trifluoromethyl)thio]phenyl}-2-phenylacetamide;

(2R)-2-amino-N-{5-[3-({2-[(dimethylcarbamoyl)amino]pyridin-4-yl}methyl)-4,4-dimethyl-2,5-dioxoimidazolidin-1-yl]-2-(trifluoromethoxy)phenyl}-2-phenylacetamide;

(2R)-2-amino-N-{5-[3-({2-[(dimethylcarbamoyl)amino]pyridin-4-yl}methyl)-4,4-dimethyl-2,5-dioxoimidazolidin-1-yl]-2-[(trifluoromethyl)thio]phenyl}-2-phenylacetamide;

3-(4-tert-butylphenyl)-5,5-dimethyl-1-{[2-(pyrimidin-5-ylamino)pyridin-4-yl]methyl}imidazolidine-2,4-dione; and 3-(4-tert-butylphenyl)-5,5-dimethyl-1-{[2-(pyrimidin-5-ylamino)pyrimidin-4-yl]methyl}imidazolidine-2,4-dione;

or an addition salt with a mineral or organic acid or with a mineral or organic base of said compound of formula (I);

said compound being in any possible racemic, enantiomeric or diastereoisomeric isomer form.

9. A pharmaceutical composition comprising a compound according to claim 1, or a pharmaceutically acceptable addition salt thereof, and one or more pharmaceutically acceptable excipients.

10. A pharmaceutical composition comprising a compound according to claim 7, or a pharmaceutically acceptable addition salt thereof, and one or more pharmaceutically acceptable excipients.

11. A pharmaceutical composition comprising a compound according to claim 8, or a pharmaceutically acceptable addition salt thereof, and one or more pharmaceutically acceptable excipients.

12. The pharmaceutical composition according to claim 9, further comprising another chemotherapy medicament for combating cancer.

* * * * *